US006846839B1

(12) United States Patent
Tang et al.

(10) Patent No.: US 6,846,839 B1
(45) Date of Patent: Jan. 25, 2005

(54) METHODS FOR TREATING DISEASES AND DISORDERS RELATED TO UNREGULATED ANGIOGENESIS AND/OR VASCULOGENESIS

(75) Inventors: Peng Cho Tang, Moraga, CA (US); Li Sun, Foster City, CA (US); Laura Kay Shawver, San Francisco, CA (US); Klaus Peter Hirth, San Francisco, CA (US); Annie Fong, Sunnyvale, CA (US)

(73) Assignee: Sugen, Inc., South San Francisco, CA (US)

( * ) Notice: Subject to any disclaimer, the term of this patent is extended or adjusted under 35 U.S.C. 154(b) by 0 days.

(21) Appl. No.: 09/333,703

(22) Filed: Jun. 16, 1999

Related U.S. Application Data

(63) Continuation-in-part of application No. 08/915,366, filed on Aug. 20, 1997, now Pat. No. 6,147,106, and a continuation-in-part of application No. 08/702,232, filed on Aug. 23, 1996, now abandoned, which is a continuation-in-part of application No. 08/655,255, filed on Jun. 5, 1996, now abandoned, and a continuation-in-part of application No. 08/655,226, filed on Jun. 5, 1996, now Pat. No. 5,886,020, and a continuation-in-part of application No. 08/655,223, filed on Jun. 5, 1996, now Pat. No. 5,792,783, and a continuation-in-part of application No. 08/655,224, filed on Jun. 5, 1996, now Pat. No. 5,883,116, and a continuation-in-part of application No. 08/659,191, filed on Jun. 5, 1996, now Pat. No. 5,883,113, which is a continuation-in-part of application No. 08/485,323, filed on Jun. 7, 1995, now Pat. No. 5,880,141.

(51) Int. Cl.$^7$ .................. A01N 43/50; A01N 43/82
(52) U.S. Cl. .................. 514/397; 514/359; 514/361; 514/362; 514/363; 514/364; 514/365; 514/372; 514/374; 514/378; 514/381; 514/383; 514/414; 514/418
(58) Field of Search .................. 514/397, 359, 514/361, 362, 363, 364, 365, 372, 374, 378, 381, 383, 414, 418

(56) References Cited

U.S. PATENT DOCUMENTS

| 5,389,661 A | * | 2/1995 | Sircar et al. | 514/381 |
| 5,610,173 A | | 3/1997 | Schwartz et al. | 514/378 |
| 5,792,783 A | * | 8/1998 | Tang et al. | 514/397 |
| 5,840,745 A | * | 11/1998 | Buzzotti et al. | 514/414 |

FOREIGN PATENT DOCUMENTS

| WO | 96/22976 | 8/1996 | |
| WO | WO-96/40116 | * 12/1996 | A61K/31/40 |
| WO | 98/38984 | 9/1998 | |

OTHER PUBLICATIONS

Abboud, "Role of platelet–derived growth factor in renal injury," *Annu. Rev. Physiol.* 57:297–309 (1995).
Abedi et al., "Singalling mechanisms in the regulation of vascular cell migration," *Cardiovasc. Res.* 30:544–556 (1995).
Abraham et al., "Human basic fibroblast growth factor: Nucleotide sequence and genomic organization," *EMBO J.* 5:2523–2528 (1986).
Adamis et al., "Increased vascular endothelial growth factor levels in the vitreous of eyes with proliferative diabetic retinopathy," *Amer. J. Ophthalmology* 118:445–450 (1994).
Adamis et al., "Inhibition of vascular endothelial growth factor prevents retinal ischemia–associated iris neovascularization in a nonhuman primate," *Arch. Ophthalmol.* 114:66–71 (1996).
Agapitos et al., "Immunohistochemical detection of platelet derived growth factor in the aortic wall of atherosclerotic rabbits," *Int. Angiol.* 15:249–251 (1996).
Aiello et al., "Suppression of retinal neovascularization in vivo by inhibition of vascular endothelial growth factor using soluble VEGF–receptor chimeric proteins," *Proc. Natl. Acad. Sci.* 92:10457–10461 (1995).
Aiello et al., "Vascular endothelial growth factor in ocular fluid of patients with diabetic retinopathy and other retinal disorders," *New England J. Med.* 331:1480–1487 (1994).
Alpers et al., "Identificationof platelet–derived growth factor A and B chains in human renal vascular rejection," *Am. J. Pathol.* 148:439–451 (1996).
Anan et al., "Vascular endothelial growth factor and platelet–derived growth factor are potential angiogenic and metastatic factors in human breast cancer," *Surgery* 119:333–339(1996).
Andrews et al. (American Veterinary Medicine Association Panel on Euthanasia), "1993 Report of the AVMA Panel on Euthanasia," *J. American Veterinary Medicine Association* 202(2):229–249 (1993).
Arbiser, "Angiogenesis and the skin: A primer," *Am. Acad. Derm.* 34:486–497 (1996).
Asano et al., "Inhibition of tumor growth and metastasis by an immunoneutralizing monoclonal antibody to human vascular endothelial growth factor/vascular permeability factor," *Cancer Res.* 55:5296–5301 (1995).
Baffour et al., "Enhanced angiogenesis and growth of collaterals by in vivo administration of recombinant basic fibroblast growth factor in a rabbit model of acute lower limb ischemia: Dose response effect of basic fibroblast growth factor," *J. Vasc. Surg.* 16:181–191 (1992).

(List continued on next page.)

*Primary Examiner*—Carla J. Myers
*Assistant Examiner*—Alexander H. Spiegler
(74) *Attorney, Agent, or Firm*—Beth A. Burrous; Foley & Lardner LLP

(57) ABSTRACT

The present invention relates to methods for treating diseases and disorders related to unregulated angiogenesis and/or vasculogenesis. More specifically, this invention relates to methods for treating diseases and disorders, such as rheumatoid arthritis, endometriosis, ocular neovascularization, solid tumor growth and metastases, and excessive scarring during wound healing, with indolinone compounds.

9 Claims, 2 Drawing Sheets

OTHER PUBLICATIONS

Barnhill et al., "Supernatants from cultured human epidermal keratinocytes stimulate angiogenesis," *Br. J. Dermatol.* 110:273–281 (1984).

Bates et al., "Biosynthesis of human fibroblast growth factor–5," *Mol. Cell. Biol.* 11:1840–1845 (1991).

Battler et al., "Intracoronary injection of basic fibroblast growth factor enhances angiogenesis in infarcted swine myocardium," *J. Am. Coll. Cardio.* 22:2001–2006 (1995).

Ben–Av et al., "Induction of vascular endothelial growth factor expression in synovial fibroblasts by prostaglandin E and interleukin–1: a potential mechanism for inflammatory angiogenesis," *FEBS Lett.* 372:83–87 (1995).

Bennet et al., "Apoptosis of human vascular smooth muscle cells derived from normal vessels and coronary atherosclerotic plaques," *J. Clin. Invest.* 95:2266–2274 (1995).

Billett et al., "Increased expression of genes for platelet–derived growth factor in circulating mononuclear cells of hypercholesterolemic patients," *Arterioscler Thromb. Vasc. Biol.* 16:399–406 (1996).

Brauchle et al., "Ultraviolet B and H2O2 are potent inducers of vascular endothelial growth factor expression in cultured keratinocytes," *J. Biol. Chem.* 271:21793–21797 (1996).

Breier et al., "Coordinate expression of vascular endothelial growth factor receptor–1 (flt–1) and its ligand suggests a paracrine regulation of murine vascular development," *Dev. Dyn.* 204:228–233 (1995).

Breier et al., "Expression of vascular endothelial growth factor during embryonic angiogenesis and endothelial cell differentiation," *Development* 114:521–532 (1992).

Brogi, et al., "Indirect angiogenic cytokines upregulate VEGF and bFGF gene expression in vascular smooth muscle cells, whereas hypoxia upregulates VEGF expression only," *Circulation* 90:649–652 (1994).

Brookes et al., "Sequence organization of the human int–2 gene and its expression in teratocarcinoma cells," *Oncogene* 4:429–436 (1989).

Brown et al., "Expression of Vascular Permeability Factor (Vascular Endothelial Growth Factor) and Its Receptors in Adenocarcinomas of the Gastrointestinal Tract," *Cancer Research* 53:4727–4735 (1993).

Brown et al., "Increased expression of vascular permeability factor (VEGF) in bullous pemphigoid, dermatitis herpetiformis, and erythema multiforme," *Invest. Dermatol.* 104:744–749 (1995).

Brown et al., "Overexpression of vascular permeability factor and its endothelial cell receptors in delayed hypersensitivity skin reactions," *J. Immunol.* 154:2801–2807 (1995).

Brown et al., "Uterine smooth muscle cells express functional receptors for vascular permeability factor/vascular endothelial growth factor," *Lab Invest* 76:245–255 (1997).

Burgess et al., "The Heparin–Binding (Fibroblast) Growth Factor Family of Proteins," *Annu. Rev. Biochem.* 58:575–606 (1989).

Byrd et al., "Expression and functional expansion of fibroblast growth factor receptor T cells in rheumatoid synovium and peripheral blood of patients with rheumatoid arthritis," *Arth & Rheumat.* 39:914–922 (1996).

Carmeliet et al., "Abnormal blood vessel development and lethality in embryos lacking a single VEGF allele," *Nature* 380:435–439 (1996).

Chabrier, "Growth factors and vascular wall," *Int. Angiol.* 15:100–103 (1996).

Cheng et al., "Synthesis and Michael reaction of 3,4–dimethylpyrrole," *J. Heterocyclic Chem.* 13:1145–1147 (1976).

Cheng, "Suppressionof glioblastoma angiogenicity and tumorigenicity by inhibition of endogenous expression of vascular endothelial growth factor," *Proc. Natl. Acad. Sci. USA* 93:8502–8507 (1996).

Chow et al., "FGF suppresses apoptosis and induces differentiation of fibre cells in the mouse lens," *Development* 121:4383–4393 (1995).

Claessen–Welsh, "PDGF Receptors: Structure and mechanism of action," *Biology of Platelet–Derived Growth Factor* (Westermark & Sorg, eds.), Cytokines. Basel, Karfger, 5:31–43 (1993).

Claffey et al., "Expression of vascular permeability factor/vascular endothelial growth factor by melanoma cells increases tumor growth, angiogenesis, and experimental metastasis," *Cancer Res.* 56:172–181 (1996).

Colville–Nash et al., "Angiogenesis and rheumatoid arthritis: Pathogenic and therapeutic implications," *Annals. Rheumatic Diseases* 51:919–925 (1992).

Connolly et al., "Human vascular permeability factor," *J. Biol. Chem.* 264:20017–20024 (1989).

Coulier et al., "Of worms and men: An evolutionary perspective on the fibroblast growth factor and FGF receptor families," *J. Mol. Evol.* 44:43–56 (1997).

Cozzolino et al., "Interferon–α and interleukin 2 synergistically enhance basic fibroblast growth factor synthesis and induce release, promoting endothelial cell growth," *J. Clin. Invest.* 91:2504–2512 (1993).

Creamer et al., "Vascular proliferation and angiogenic factors in psoriasis," *Clin. Exp. Dermatol.* 20:6–9 (1995).

D'Amato et al., "Thalidomide is an inhibitor of angiogenesis," *Proc. Natl. Acad. Sci. USA* 91:4082–4085 (1994).

D'Amore et al., "Endothelial cell mitogens derived from retina and hypothalamus: Biochemical and biological similarities," *J. Cell Biol.* 99:1545–1549 (1976).

De Vries et al., "The fms–Like Tyrosine Kinase, a Receptor for Vascular Endothelial Growth Factor," *Science* 255:989–991 (1992).

Delli–Bovi et al., "An oncogene isolated by transfection of kaposi's sarcoma DNA encodes a growth factor that is a member of the FGF family," *Cell* 50:729–737 (1987).

Deng et al., "Murine FGFR–1 is required for early postimplantation growth and axial organization," *Genes & Dev.* 8:3045–3057 (1994).

Detmar et al., "Overexpression of vascular permeability factor/vascular endothelial growth factor and its receptors in psoriasis," *J. Exp. Med.* 180:1141–1146 (1994).

Dickinson et al., "Quantification of angiogenesis as an independent predictor of prognosis in invasive bladder carcinomas," *Br. J. Urol.* 74:762–766 (1994).

Dionne et al., "Cloning and expression of two distinct high–affinity receptors cross–reacting with acidic and basic fibroblast growth factors," *EMBO J.* 9:2685–92 (1990).

Eckhardt et al., "A phase I clinical and pharmacokinetic study of angiogenesis inhibitor, tecogalan sodium," *Ann. Oncol.* 7:491–496 (1996).

Fava et al., "Vascular permeability factor/endothelial growth factor: Accumulation and expression in human synovial fluids and rheumatoid synovial tissue," *J. Exp. Med.* 180:341–346 (1994).

Feldman et al., "Role of cytokines in rheumatoid arthritis," *Ann. Rev. Immunol.* 14:397–440 (1996).

Ferrara et al., "Heterozygous embryonic lethality induced by targeted inactivation of the VEGF gene," *Nature* 380:439–442 (1996).

Ferrara, "Vascular endothelial growth factor," *Trends Cardiovasc. Med.* 3:244–250 (1993).

Finch et al., "Human KGF is FGF–related with properties of a paracrine effector of epithelial cell growth," *Science* 245:752–755 (1989).

Folkman et al., "Induction of angiogenesis during the transition from hyperplasia to neoplasia," *Nature* 339:58–61 (1989).

Folkman, "What is the Evidence that Tumors are Angiogenesis Dependent?" *Journal of the National Cancer Institute* 82:4–6 (1990).

Folkman, "Angiogenesis in psoriasis: Therapeutic implications," *J. Invest. Dermatol.* 59:40–43 (1973).

Fong et al., "Role of the Flt–1 receptor tyrosine kinase in regulating the assembly of vascular endothelium," *Nature* 376:66–70 (1995).

Giordano et al., "Intracoronary gene transfer of fibroblast growth factor–5 increases blood flow and contractile function in an ischemic region of the heart," *Nature Med.* 2:534–539 (1996).

Givol et al., "Complexity of FGF Receptors: Genetic Basis for Structural Diversity and Functional Specificity," *The FASEB Journal* 6:3362–3369 (1992).

Gospodarowicz, "Purification of a fibroblast growth factor from bovine pituitary," *J. Biol. Chem.* 250:2515–2520 (1975).

Gospodarowitz et al., "The angiogenic activity of fibroblast and epidermal growth factor," *Exp. Eye Res.* 28:501–514 (1979).

Gospodarowitz, "Humoral control of cell Proliferation: The role of firbroblast growth factor in regeneration, angiogenesis, wound healing, and neoplastic growth," *Prog. Clin. Biol. Res.* 9:1–19 (1976).

Graf et al., "Mitogen–activated protein kinase activation is involved in platelet–derived growth factor–directed migration by vascular smooth muscle cells," *Hypertension* 29:334–339 (1997).

Grant et al., "Inhibition of IGF–I and b–FGF stimulated growth of human retinal endothelial cells by somatostatin analogue, octreotide: A potential treatment for ocular neovascularization," *Reg. Peptides* 48:267–278 (1993).

Grant et al., "Insulin–like growth factors in vitreous," *Diabetes* 35:416–420 (1986).

Gray et al., "FGF–1 affixation stimulated ePTFE endothelialization without intimal hyperplasia," *J. Surg. Res.* 57:596–612 (1994).

Green et al., "Promiscuity of fibroblast growth factor receptors," *BioEssays* 18:639–646 (1996).

Hanneken et al., "Altered distribution of basic fibroblast growth factor in diabetic retinopathy," *Arch. Ophthalmol* 109:1005–1011 (1991).

Harada et al., "Vascular endothelial growth factor administration in chronic myocardial ischemia," *Am J. Physiol.* 270:1792–1802 (1996).

Hatva, et al., "Expression of endothelial cell–specific receptor tyrosine kinases and growth factors in human brain tumors," *Am. J. Pathol.* 146:368–378 (1996).

Hatva, et al., "Vascular growth factors and receptors in capillary hemangioblastomas and hemangiopericytomas," *Amer. J. Pathol.*, 148:763–775 (1996).

Haub et al., "Expression of the murine fibroblast growth factor 5 gene in the adult central nervous system," *Proc. Natl. Acad. Sci. USA* 87:8022–8026 (1990).

Herman et al., "Capillary endothelial cell migration: loss of stress fibres in response to retina–derived growth factor," *J. Muscle Res. Cell Motil* 5:697–709 (1984).

Holmgren et al., "Angiogenesis during human extraembryonic development involves the spatiotemporal control of PDGF ligand and receptor gene expression," *Dev.* 113:749–754 (1991).

Holtrich et al., "Two additional protein–tyrosine kinases expressed in human lung: Fourth member of the fibroblast growth factor receptor family and an intracellular protein–tyrosine kinase," *Proc. Natl. Acad. Sci. USA* 88:10411–10415 (1991).

Horak et al., "Angiogenesis, assessed by platelet/endothelial cell adhesion molecule antibodies, as indicator of node metastases and survival in breast cancer," *Lancet* 340:1120–1124(1992).

Hosaka et al., "Expression of basic fibroblast growth factor and angiogenin in arthritis," *Pathobiol.* 63:249–256 (1995).

Hughes, "Localisation and differential expression of the fibroblast growth factor receptor (FGFR) multigene family in normal and atherosclerotic human arteries," *Cardiovasc. Res.* 32:557–569 (1996).

Isacchi et al., "Complete sequence of a human receptor for acidic and basic fibroblast growth factors," *Nucleic Acids Research* 18:1906 (1990).

Isner et al., "Clinical evidence of angiogenesis after arterial gene transfer of phVEGF$_{165}$ in patient with ischaemic limb," *Lancet* 348:370–374 (1996).

Ito et al., "Expression of PDGF in relation to cell division in atherosclerotic intima of human carotid arteries," *Neurol. Res.* 17:345–348 (1995).

Jakeman et al., "Developmental expression of binding sites and messenger ribonucleic acid for vascular endothelial growth factor suggests a role for this protein in vasculogenesis and angiogenesis," *Endocrinology* 133:848–859 (1993).

Jaye et al., "Fibroblast growth factor receptor tyrosine kinases: Molecular analysis and signal transduction," *Biochimica et Biophysica Acta* 1135:185–199 (1992).

Jaye et al., "Human endothelial cell growth factor: Cloning, nucleotide sequence, and chromosome localization," *Science* 233: 541–545 (1986).

Johnson et al., "Structural and Functional Diversity in the FGF Receptor Multigene Family," *Advances in Cancer Research* 60:1–41 (1993).

Joukov et al., "A novel vascular endothelial growth factor, VEGF–C, is a ligand for the Flt4 (VEGFR–3) and KDR (VEGFR–2) receptor tyrosine kinases," *EMBO J.* 15:290–298 (1996).

Kaipainen et al., "Enhanced expression of the tie receptor tyrosine kinase messenger RNA in the vascular endothelium of metastatic melanomas," *Cancer Res.* 54:6571–6577 (1994).

Kaipainen et al., "The related FLT4, FLT1 and KDR receptor tyrosine kinases show distinct expression patterns in human fetal endothelial cells," *J. Exp. Med.* 178:2077–2088 (1993).

Kaminski et al., "Angiogenesis induction by CD–4 positive lymphocytes," *Proc. Soc. Exp. Biol. Med.* 188:440–443 (1988).

Keegan et al., "Isolation of an additional member of the fibroblast growth factor receptor family, FGFR–3," *Proc. Natl. Acad. Sci. USA* 88:1095–1099 (1991).

Kendall and Thomas, "Inhibition of vascular endothelial cell growth factor activity by an endogenously encoded soluble receptor," *Proc. Natl. Acad. Sci. USA* 90:10705–10709 (1993).

Keyt et al., "Identification of vascular endothelial growth factor determinants for binding KDR and FLT–1 receptors," *J. Biol. Chem.* 271:5638–5646 (1996).

Kim et al., "Inhibition of vascular endothelial growth factor–induced angiogenesis suppresses tumour growth in vivo," *Nature* 362:841–844 (1993).

Kirschner et al., "Angiogenesis factor in endometrial carcinoma: A new prognostic indicator?" *Am. J. Obstet. Gynecol.* 174:1879–1882 (1996).

Knighton et al., "Oxygen tension regulates the expression of angiogenesis factor by macrophages," *Science* 221:1283–1285 (1983).

Koch et al., "Interleukin–8 as a macrophage–derived mediator of angiogenesis," *Science* 258:1798–1801 (1992).

Koch et al., "Vascular endothelial growth factor," *J. Immunol.* 152:4149–4156 (1994).

Kornbluth et al., "Novel tyrosine kinase identified by phosphotyrosine antibody screening of cDNA libraries," *Mol. Cell. Biol.* 8:5541–5544 (1988).

Koster et al., "Enhanced migratory activity of vascular smooth muscle cells with high expression of platelet–derived growth factor A and B," *Angiology* 46:99–106 (1995).

Kukk et al., "VEGF–C receptor binding and pattern of expression with VEGFR–3 suggests a role in lymphatic vascular development," *Development* 122:3829–3837 (1996).

Kurokawa et al., "Cloning and expression of cDNA encoding human basic fibroblast growth factor," *FEBS Lett.* 213:189–194 (1987).

Lazarous et al., "Effects of chronic systemic administration of basic fibroblast growth factor on collateral development in the canine heart," *Circulation* 91:145–153 (1995).

Lee et al., "Vascular endothelial growth factor–related protein: A ligand and specific activator of the tyrosine kinase receptor Flt4," *Proc. Natl. Acad. Sci. USA* 93:1988–1992 (1996).

Leveen et al., "Mice deficient for PDGF B show renal, cardiovascular, and hematological abnormalities," *Genes Dev.* 8:1875–1887 (1994).

Li et al., "Diminished heparin binding of a basic fibroblast growth factor mutant is associated with reduced receptor binding, mitogenesis, plasminogen activator induction, and in vitro angiogenesis," *Biochem* 33:10999–11007 (1994).

Li et al., "VEGF, flk–1, and flt–1 expression in a rat myocardial infarction model of angiogenesis," *Am. J. Physiol.* 270:1803–1811 (1996).

Lindahl et al., Pericyte loss and microaneurysm formation in PDGF–B–deficient mice, *Science* 227:242–245 (1997).

Lindner & Reidy, "Expression of basic fibroblast growth factor and its receptor by smooth muscle cells and endothelium in injured rat arteries," *Circ. Res.* 73:589–595 (1993).

Lu and Ory, "Endometriosis: Current Management," *Mayo Clin. Proc.* 70:453–463 (1995).

Lu et al., "Inhibitory effect of antibody against basic fibroblast growth factor on androgen– or glucocorticoid–induced growth of shionogi carcinoma 115 cells in serum free culture," *Cancer Res.* 49:4963–4967 (1989).

Majewski et al., "Angiogenic capability of peripheral blood mononuclear cells in psoriasis," *Arch. Dermatol.* 121:1018–1021 (1985).

Majewski et al., "Serum samples from patients with active psoriasis enhance lymphocyte–induced angiogenesis and modulate endothelial cell proliferation," *Arch. Dermatol.* 123:221–225 (1987).

Malecaze et al., "Detection of vascular endothelial growth factor messenger RNA and vascular endothelial growth factor– like activity in proliferative diabetic retinopathy," *Arch. Ophthalmol.* 112:1476–1482 (1994).

Malhotra et al., "Angiogenic properties of normal and psoriatic skin associate with epidermis, not dermis," *Lab Invest.* 61:162–165 (1989).

Marics et al., "Characterization of the HST–related FGF.6 gene, a new member of the fibroblast growth factor gene family," *Oncogene* 4:335–340 (1989).

Masood et al., "Vascular endothelial growth factor/vascular permeability factor is an autocrine growth factor for AIDS–Kaposi sarcoma," *Proc. Natl. Acad. Sci. USA* 94:979–984 (1997).

McLaren et al., "Vascular endothelial growth factor is produced by peritoneal fluid macrophages in endometriosis and is regulated by ovarian steroids," *J. Clin. Invest.* 98:482–489 (1996).

McLaren et al., "Vascular endothelial growth factor (VEGF) concetrations are elevatedin peritoneal fluid of women with endometriosis," *Hum. Reprod.* 11:220–223 (1996).

Michiels et al., "Hypoxia stimulates human endothelial cells to release smooth muscle cell mitogens: Role of prostaglandins and bFGF," *Exp. Cell. Res.* 213:43–54 (1994).

Mignatti et al., "In vitro angiogenesis of the human amniotic membrane: Requirement for basic fibroblast growth factor–induced proteinases," *J. Cell. Biol.* 108:671–682 (1989).

Millauer et al., "Glioblastoma growth inhibited in vivo by a dominant–negative Flk–1 mutant," *Nature* 367:576–579 (1994).

Millauer et al., "High Affinity VEGF Binding and Developmental Expression Suggest Flk–1 as a Major Regulator of Vasculogenesis and Angiogenesis," *Cell* 72:835–846 (1993).

Millauer et al., "Dominant–negative inhibition of Flk–1 suppresses the growth of many tumor types in vivo," *Cancer Res.* 56:1615–1620 (1996).

Miller et al., "Vascular endothelial growth factor/vascular permeability factor is temporally and spatially correlated with ocular angiogenesis in a primate model," *Am. J. Pathol.* 145:574–584 (1994).

Miyamoto et al., "Molecular cloning of a novel cytokine cDNA encoding the ninth member of the fibroblast growth factor family, which has a unique secretion property," *Mol. Cell. Biol.* 13:4251–4259 (1993).

Mullins et al., "Inhibition of PDGF receptor binding and PDGF–stimulated biological activity in vitro and of intimal lesion formation in vivo by 2–bromomethyl–5–chlorobenzene sulfonylphthalimide," *Arterioscler. Thromb* 14:1047–1055 (1994).

Myoken, et al., "Vascular endothelial cell growth factor (VEGF) produced by A–431 human epidermoid carcinoma cells and identification of VEGF membrane binding sites," *Proc. Natl. Acad. Sci. USA,* 88:5819–5823 (1991).

Nabel et al., "Recombinant fibroblast growth factor–1 promotes intimal hyperplasia and angiogenesis in arteries In vivo," *Nature* 362:844–846 (1993).

Nagashima et al., "Role of vascular endothelial growth factor in angiogenesis of rheumatoid arthritis," *J. Rheumatol.* 22:1624–1630 (1995).

Nakamoto et al., "Basic fibroblast growth factor in human prostate cancer cells," *Cancer Res.* 52:571–577 (1992).

Newby et al., "Proliferation, migration, matrix turnover, and death of smooth muscle cells in native coronary and vein graft atherosclerosis," *Curr. Opin. Cardiol.* 11:574–582 (1996).

Nicosia et al., "Vascular endothelial growth factor, platelet–derived growth factor, and insulin–like growth factor–1 promote rat aortic angiogenesis in vitro," *Amer. J. Pathol.* 145:1023–1029 (1994).

Nishioka et al., "The influence of the epidermis and other tissues on blood vessel growth in the hamster cheek pouch," *J. Invest. Dermatol.* 58:33–45 (1972).

Nisolle et al., "Morphometric study of the stromal vascularization in peritoneal endometriosis," *Fertil. Steril.* 59:681–684 (1993).

O'Keefe et al., "Stimulation of growth of keratinocytes by basic fibroblast growth factor," *J. Invest. Dermatol.* 90:767–769 (1988).

O'Reilly et al., "Angiostatin: A novel angiogenesis inhibitor that mediates the suppression of metastases by a Lewis lung carcinoma," *Cell* 79:315–328 (1994).

O'Reilly et al., "Endostain: An endogenous inhibitor of angiogenesis and tumor growth," *Cell* 88:277–285 (1997).

Olofsson et al., "Genomic organization of the mouse and human genes for vascular endothelial growth factor B (VEGF–B) and characterization of a second splice isoform," *J. Biol. Chem.* 271:19310–19317 (1996).

Olofsson et al., "Vascular endothelial growth factor B, a novel growth factor for endothelial cells," *Proc. Natl. Acad. Sci. USA* 93:2576–2481 (1996).

Ornitz et al., "Receptor specificity of the fibroblast growth factor family," *J. Biol. Chem.* 271:15292–15297 (1996).

Padua et al., "Basic fibroblast growth factor is cardioprotective in ischemia–reperfusion injury," *Mol. Cell. Biochem.* 143:129–135 (1995).

Pajusola et al., "FLT4 receptor tyrosine kinase contains seven immunoglobulin–like loops and is expressed in multiple human tissues and cell lines," *Cancer Res.* 52:5738–43 (1992).

Paleolog, "Angiogenesis: A critical process in the pathogenesis of RA– a role for VEGF," *Br. J. Rheumatol.* 35:917–920 (1996).

Parlow et al., "Localization of bFGF–like proteins as punctate inclusions in the preseptation myocardium of the chicken embryo," *Dev. Biol.* 146:139–147 (1991).

Partanen et al., "FGFR–4 a novel acidic fibroblast growth factor receptor with a distinct expression pattern," *EMBO J.* 10:1347–1354 (1991).

Partanen et al., "Putative tyrosine kinases expressed in K–562 human leukemia cells," *Proc. Natl. Acad. Sci. USA* 87:8913–8917 (1990).

Pasquale and Singer, "Identification of a developmentally regulated protein–tyrosine kinase by using anti–phosphotyrosine antibodies to screen a cDNA expression library," *Proc. Natl. Acad. Sci. USA* 86:5449–5453 (1989).

Payson et al., "The human FGF–8 gene localizes on chromosome 10q24 and is subjected to induction by androgen in breast cancer cells," *Oncogene* 13:47–53 (1996).

Pe'er et al., "Hypoxia–induced expression of vascular endothelial growth factor by retinal cells is a common factor in a neovascularizing ocular diseases," *Lab Invest.* 72:638–645 (1995).

Peacock et al., "A novel angiogenesis inhibitor suppresses rat adjuvant arthritis," *Cell Immunol.* 160:178–184 (1995).

Peacock et al., "Angiogenesis inhibition suppresses collagen arthritis," *J. Exp. Med.* 175:1135–1138 (1992).

Pearlman et al., "Magnetic resonance mapping demonstrates benefits of VEGF–induced myocardial angiogenesis," *Nature Med.* 1:1085–1089 (1995).

Peters et al., "Targeted expression of a dominant negative FGF receptor blocks branching morphogenesis and epithelial differentiation of the mouse lung," *EMBO J.* 13:3296–3301 (1994).

Plate & Risau, "Angiogenesis in malignant gliomas,"*GLIA* 15:339–347 (1995).

Plate et al., "Platelet–Derived Growth Factor Receptor–$\beta$ is Induced during Tumor Development and Upregulated during Tumor Progression in Endothelial Cells in Human Gliomas," *Laboratory Investigation* 64:529–534 (1992).

Plate et al., "Vascular endothelial growth factor and glioma angiogenesis: Coordinate induction of VEGF receptors, distribution of VEGF protein and possible in vivo regulatory mechanisms," *Int. J. Cancer* 59:520–529 (1994).

Plowman et al., "Receptor Tyrosine Kinases as Targets for Drug Intervention," *DN&P* 7(6):334–339 (1994).

Poltorak et al., "$VEGF_{145}$, a secreted vascular endothelial growth factor isoform that binds to extracellular matrix," *J. Biol. Chem.* 272:7157–7158 (1997).

Pouchot et al., "Validity, reliability, and sensitivity to change of a french version of the Arthritis impact measurement scales 2 (AIMS2) in patients with rheumatoid arthritis treated with methotrexate," *J. Rheumatol.* 23:56–60 (1996).

Presta et al., "Purification from a human hepatoma cell line of a basic fibroblast growth factor–like molecule that stimulates capillary endothelial cell plasminogen activator production, DNA synthesis, and migration," *Mol. Cell. Biol.* 6:4060–4066 (1986).

Qu et al., "Mast cells are a major source of basic fibroblast growth factor in chronic inflammation and cutaneous hemangioma," *Am. J. Pathol.* 147:564–573 (1995).

Quinn et al., "Fetal liver kinase 1 is a receptor for vascular endothelial growth factor and is selectively expressed in vascular endothelium," *Proc. Natl. Acad. Sci. USA* 90:7533–7537 (1993).

Randone et al., "Growth factors and myointimal hyperplasia in experimental aortic allografts," *Eur. J. Vasc. Endovasc. Surg.* 13:66–71 (1997).

Risau, "Developing brain produces an angiogenesis factor," *Proc. Natl. Acad. Sci.* 83:3855–3859 (1986).

Robinson et al., "Expression of a truncated FGF receptor results in defective lens development in transgenic mice," *Development* 121:3959–3967 (1995).

Rockwell et al., "In vitro neutralization of vascular endothelial growth factor activation of Flk–1 by a monoclonal antibody," *Mol. Cell. Diff.* 3:91–109 (1995).

Rockwell et al., "Antitumor activity of anti–flk–1 monoclonal antibodies," *Proc. Am. Assc. Cancer Res.* 38:266 Abstract #1788 (1997).

Rockwell, et al., "Cell–surface perturbations of the epidermal growth factor and vascular endothelial growth factor receptors by phophorothioate oligodeoxynucleotides," *Proc. Natl. Acad. Sci. USA* 94:6523–6528 (1997).

Ross et al., "The biology of platelet–derived growth factor," *Cell* 46:155–169 (1986).

Ruta et al., "Receptor for acidic fibroblast growth factor is related to the tyrosine kinase encoded by the fms–like gene (FLG)," *Proc. Natl. Acad. Sci. USA* 86:8722–8726 (1989).

Saleh, et al., "Inhibition of growth of C6 glioma cells in vivo by expression of antisense vascular endothelial growth factor sequence," *Cancer Res.* 56:393–401 (1996).

Sato et al. "Autocrinological role of basic fibroblast growth factor on tube formation of vascular endothelial cells in vitro," *Biochem. Biophys. Res. Com.* 180:1098–1102 (1991).

Schweigerer et al., "Capillary endothelial cells express basic fibroblast growth factor, a mitogen that promotes their own growth," *Nature* 325:257–259 (1987).

Shalaby et al., "Failure of blood–island formation and vasculogenesis in Flk–1 deficient mice," *Nature* 376:62–66 (1995).

Shaw, "A risk benefit assessment of drugs used in the treatment of endometriosis," *Drug Safety* 11:104–113 (1994).

Shawver et al., "Receptor tyrosine kinases as targets for inhibition of angiogenesis," *DDT* 2:50–63 (1997) Reprints From Elsevier Trends Journals.

Shibuya et al., "Nucleotide sequence and expression of a novel human receptor–type tyrosine kinase gene (flt) closely realted to the fms family," *Oncogene* 5:519–524 (1990).

Shifren et al., "Ovarian steroid regulation of vascular endothelial growth factor in the human endometrium: Implications for angiogenesis during the menstrual cycle and in the pathogenesis of endometriosis," *J. Clin. Endocrinol. Metab.* 81:3112–3118 (1996).

Shweiki et al., "Vascular endothelial growth factor induced by hypoxia may mediate hypoxia–initiated angiogenesis," *Nature* 359:843–845 (1992).

Singh et al., "Cell density–dependent regulation of basic fibroblast growth factor expression in human renal cell carcinoma cells," *Cell Growth Diff.* 7:397–404 (1996).

Sivalingam et al., "Basic fibroblast growth factor levels in the vitreous of patients with proliferative diabetic retinopathy," *Arch. Ophthalmol.* 108:869–872 (1990).

Smallwood et al., "Fibroblast growth factor (FGF) homologous factors: New members of the FGF family implicated in nervous system development," *Proc. Natl. Acad. Sci. USA* 93:9850–9857 (1996).

Smith et al., "Multiple RNAs expressed from the int–2 gene in mouse embryonal carcinoma cell lines encode a protein with homology to fibroblast growth factors," *EMBO J.* 7:1013–1022 (1988).

Soriano, "Abnormal kidney development and hematological disorders in PDGF β–receptor mutant mice," *Genes Dev.* 8:1888–1896 (1994).

Stavri et al., "Hypoxia and platelet–derived growth factor–BB synergistically upregulate the expression of vascular endothelial growth factor in vascular smooth muscle cells," *FEBS Lett.* 358:311–315 (1996).

Strawn, et al., "Flk–1 as a target for tumor growth inhibition," *Cancer Res.* 56:3540–3545 (1996).

Sugi et al., "Developmental expression of fibroblast growth factor receptor–1 (cek–1, fig) during heart development," *Dev. Dyn.* 202:115–125 (1995).

Sundberg et al., "Microvascular pericytes express platelet–derived growth factor–β receptors in human healing wounds and colorectal adenocarcinoma," *Amer. J. Pathol.* 143:1377–1388 (1993).

Taira et al., "cDNA sequence of human transforming gene hst and identification of the coding sequence required for transforming activity," *Proc. Natl. Acad. Sci. USA* 84:2980–2984 (1987).

Takahashi et al., "Expression of vascular endothelial growth factor and its receptor, KDR, correlates with vascularity, metastasis, and proliferation of human colon cancer," *Cancer Res.* 55:3964–3968(1995).

Takahashi et al., "Inhibition of cell growth and tumorigenesis of human glioblastoma cells by a neutralizing antibody against human basic fibroblast growth factor," *FEBS Lett.* 288:65–71 (1991).

Takahashi, et al., "Markedly increased amounts of messenger RNAs for vascular endothelial growth and placenta growth factor in renal cell carcinoma associated with angiogenesis," *Cancer Res.* 54:4233–4237 (1994).

Takano et al., "Suramin, an anticancer and angiosuppressive agent, inhibits endothelial cell binding of basic fibroblast growth factor, migration, proliferation, and induction of urokinase–type plasminogen activator," *Cancer Res.* 54:2654–2660 (1994).

Takeshita et al., "Therapeutic Angiogenesis: A single intraarterial bolus of vascular endothelial growth factor augments revascularization in a rabbit ischemic hind limb model," *J. Clin. Invest.* 93:662–670 (1994).

Tamura et al., "Nitric oxide mediates interleukin–1–induced matrix degradation and basic fibroblast growth factor release in cultured rabbit articular chondrocytes: A possible mechanism of pathological neovascularization in arthritis," *Endocrinol.* 137:3729–3737 (1996).

Tanaka et al., "Cloning and characterization of an androgen–induced growth factor essential for the androgen–dependent growth of mouse mammary carcinoma cells," *Proc. Natl. Acad. Sci. USA* 89:8928–8932 (1992).

Terman et al., "Identification of the KDR tyrosine kinase as a receptor for vascular endothelial cell growth factor," *Biochem. Biophys. Res. Comm.* 187:1579–1586 (1992).

Thomas & Prentice, "The aetiology and pathogenesis of endometriosis," *Reprod. Med. Rev.* 1:21–36 (1992).

Thomas et al., "Brain fibroblast growth factor," *J. Biol. Chem* 255:5517–5520 (1980).

Toi, et al., "Association of vascular endothelial growth factor expression with tumor angiogenesis and with early relapse in primary breast cancer," *Jpn. J. Cancer Res.* 85:1045–1049 (1994).

Tolentino et al., "Intravitreous injections of vascular endothelial growth factor produce retinal ischemia and microangiopathy in an adult primate," *Ophthalmology* 103:1820–1828 (1996).

Tolentino et al., "Vascular endothelial growth factor is sufficient to produce iris neovascularization and neovascular glaucoma in a nonhuman primate," *Arch. Ophthalmol.* 114:964–970 (1996).

Tsai, et al., "Vascular endothelial growth factor in human glioma cell lines: induced secretion by EGF, PDGF–BB, and bFGF," *J. Neurosurg.* 82:864–873 (1995).

Van neck et al., "Expression of basic fibroblast growth factor and fibroblast growth factor receptor genes in cultured rat aortic smooth muscle cells," *Biochim. Biophys. Acta.* 1261:210–214 (1995).

Voller et al., "Ch. 45—Enzyme–Linked Immunosorbent Assay," in *Manual of Clinical Immunology*, 2$^{nd}$ edition, Rose and Friedman editors, American Society of Microbiology, Washington, D.C., pp. 359–371 (1980).

Walternberger et al., "Ischemia–induced transplant arteriosclerosis in the rat," *Arterioscler Thromb. Vasc. Biol.* 16:1516–1523 (1996).

Ware et al., "Angiogenesis in ischemic heart disease," *Nature Med.* 3:158–164 (1997).

Warren et al., "Regulation by vascular endothelial growth factor of human colon cancer tumorigenesis in a mouse model of experimental liver metastasis," *J. Clin. Invest.* 95:1789–1797 (1995).

Werner et al., "Targeted expression of a dominant–negative FGF receptor mutant in the epidermis of transgenic mice reveals a role of FGF in keratinocyte organization and differentiation," *EMBO J.* 12:2635–2643 (1993).

Wolf, "Angiogenesis in normal and psoriatic skin," *Lab Invest* 61:139–142 (1989).

Yamaguchi et al., "fgfr–1 is required for embryonic growth and mesodermal patterning during mouse gastrulation," *Genes & Dev.* 8:3032–3044 (1994).

Yamaguchi et al., "Differential expression of two fibroblast growth factor–receptor genes is associated with malignant progression in human astrocytomas," *Proc. Natl. Acad. Sci.* 91:484–488 (1994).

Yamaguchi et al., "flk–1 and flt–related receptor tyrosine kinase is an early marker for endothelial cell precursors," *Development* 118:489–98 (1993).

Yanigisawa–Miwa et al., "Salvage of infarcted myocardium by angiogenic action of basic fibroblast growth factor," *Science* 257:1401–1403 (1992).

Yoshida et al., "Genomic sequence of hst, a transforming gene encoding a protein homologous to fibroblast growth factors and the int–2–encoded protein," *Proc. Natl. Acad. Sci. USA* 84:7305–7309 (1987).

Yoshiji, et al., "Expression of vascular endothelial growth factor, its receptor, and other angiogenic factors in human breast cancer," *Cancer Res.* 56:2013–2016 (1996).

Zhan et al., "The human FGF–5 oncogene encodes a novel protein related to fibroblast growth factors," *Mol. Cell. Biol.* 8:3487–3495 (1988).

Zhao et al., "Costimulation of human CD4+ T cells by fibroblast growth factor–1 (Acidic fibroblast growth factor," *J. Immunol.* 155:3904–3911 (1995).

Zhao et al., "Induction of acidic fibroblast growth factor and full–length platelet–derived growth factor expression in human cardiac allografts," *Circulation* 90:677–685 (1994).

Zhao et al., "Modification of alternative messenger RNA splicing of fibroblast growth factor receptors in human cardiac allografts during rejection," *J. Clin. Invest.* 94:992–1003 (1994).

\* cited by examiner

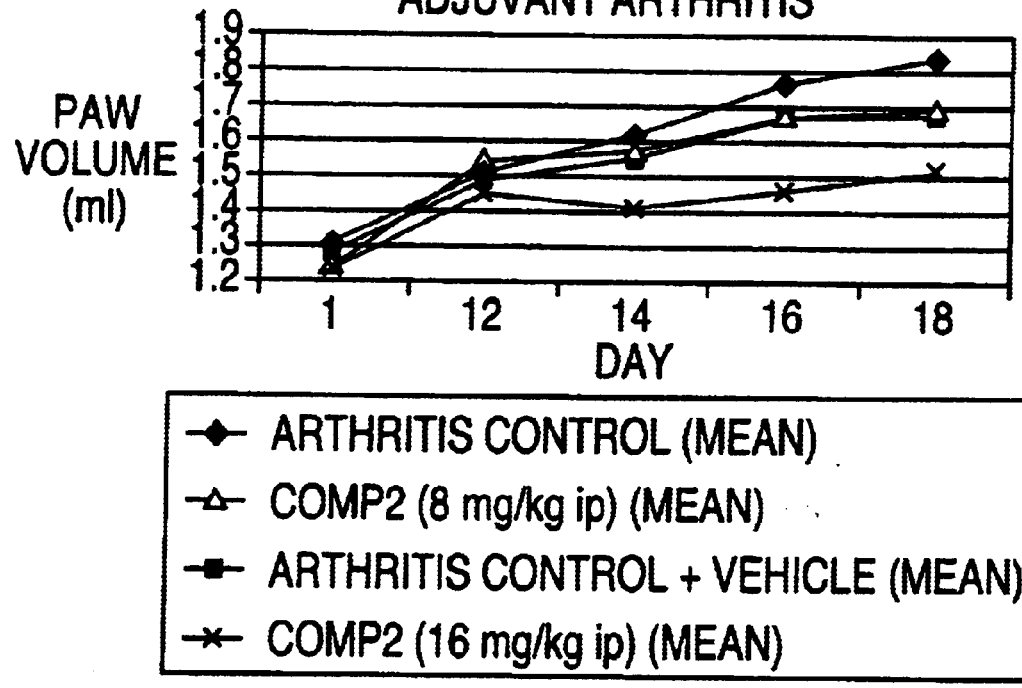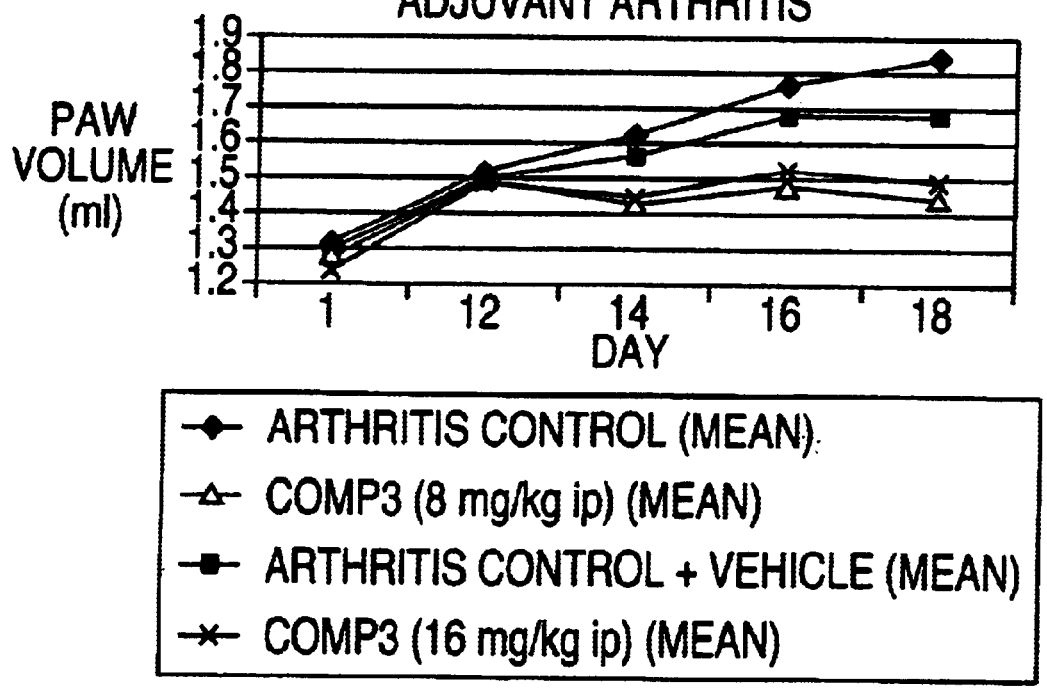

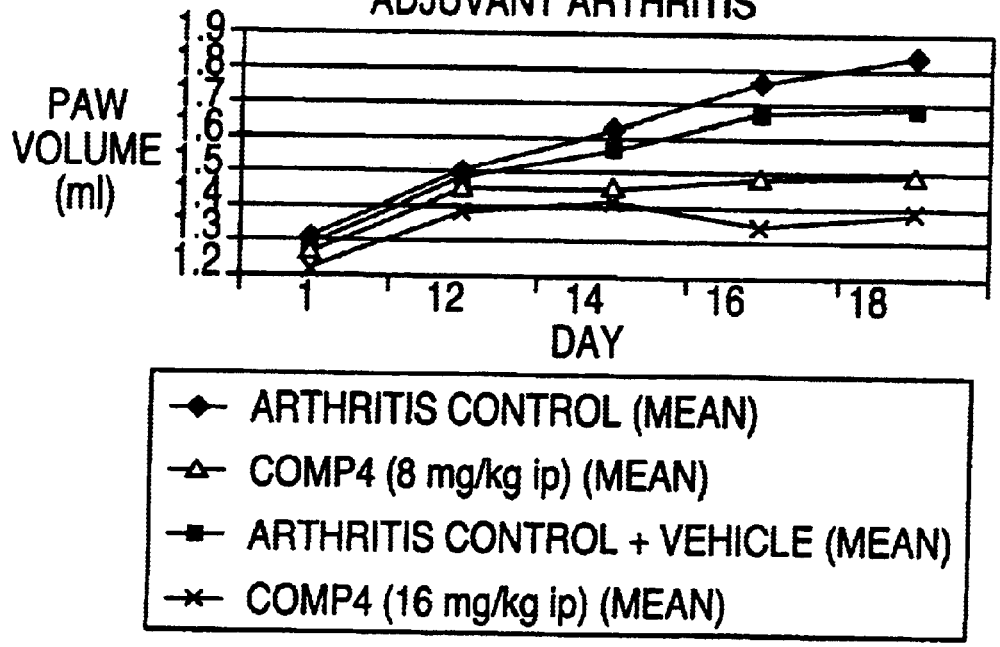
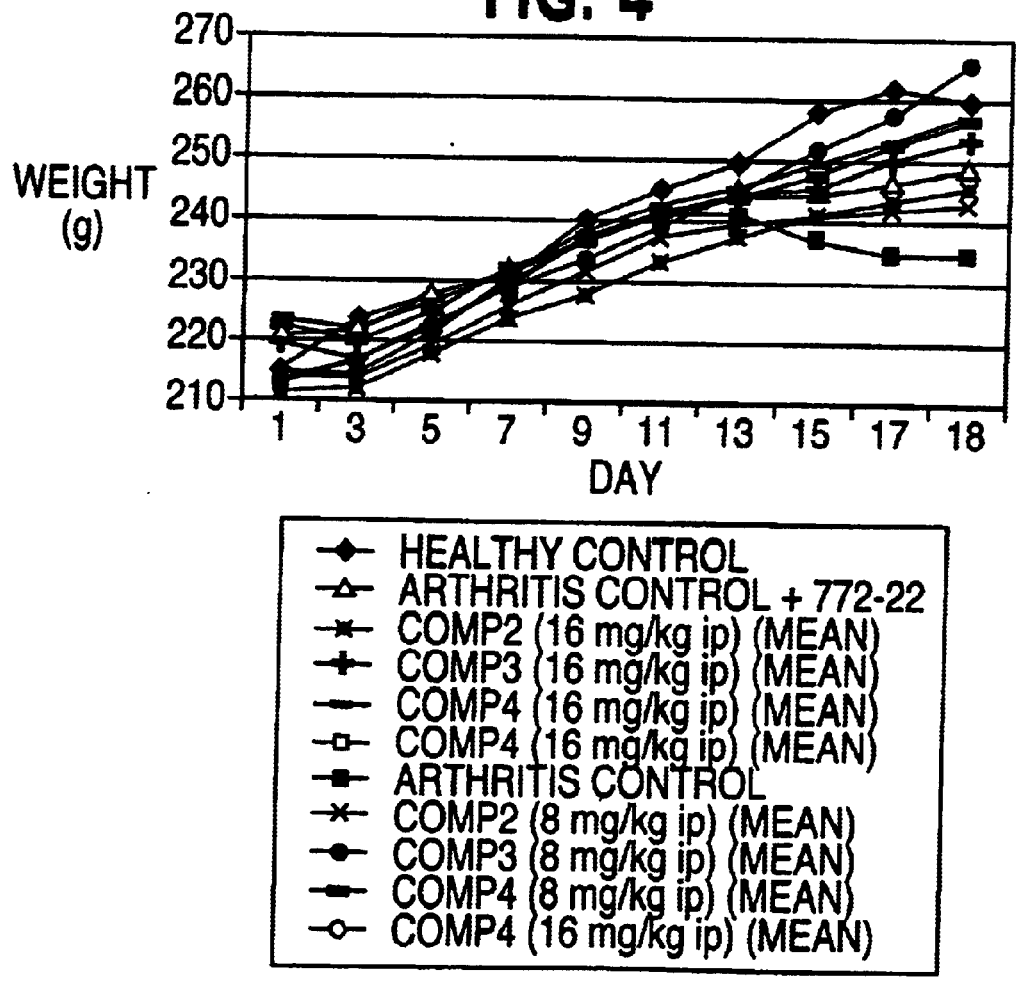

METHODS FOR TREATING DISEASES AND DISORDERS RELATED TO UNREGULATED ANGIOGENESIS AND/OR VASCULOGENESIS

This application is a continuation-in-part of U.S. patent applications Ser. No. 08/915,366 filed Aug. 20, 1997, now U.S. Pat. No. 6,147,106; and Ser. No. 08/702,232 filed Aug. 23, 1996 now abandoned, which is a continuation-in-part of U.S. patent application Ser. No. 08/655,255 field Jun. 5, 1996 now abandoned and is a continuation-in-part of Ser. No. 08/655,223 filed Jun. 5, 1996, now U.S. Pat. No. 5,792,783, and is a continuation in part of Ser. No. 08/655,224 filed Jun. 5, 1996 now U.S. Pat. No. 5,583,116 and is a continuation in part of Ser. No. 08/658,191 filed on Jun. 5, 1996 now U.S. Pat. No. 5,883,113, which is a continuation-in-part of U.S. patent application Ser. No. 08/485,323 filed Jun. 7, 1995, now U.S. Pat. No. 5,880,141, all of which are incorporated herein by reference in their entirety, including any drawings.

RELATED APPLICATIONS

This application is related to and claims priority to the U.S. Provisional Application Ser. No. 60/089,521 which was filed by Tang, et al. on Jun. 16, 1998 and entitled "METHODS FOR TREATING DISEASES AND DISORDERS RELATED TO UNREGULATED ANGIOGENESIS AND/OR VASCULOGENESIS" which is hereby incorporated by reference herein in its entirety including any drawings.

FIELD OF THE INVENTION

The present invention relates to methods of treating diseases and disorders related to unregulated angiogenesis and/or vasculogenesis. More specifically, this invention relates to methods of treatment of diseases and disorders such as rheumatoid arthritis, endometriosis, ocular diseases, cancer and metastases, psoriasis, arterial thickening and restenosis, and excessive scarring during wound healing, resulting from unregulated angiogenesis and/or vasculogenesis.

BACKGROUND OF THE INVENTION

The following description of the background of the invention is provided to aid in understanding the invention, but is not admitted to be or to describe prior art to the invention.

Cell to cell communication is imperative for physiological and pathological processes associated with multicellular organisms. This is particularly true for angiogenesis, where the blood vessel endothelial cells require signals generated from cells in the hypoxic tissue in order to initiate the process of forming new capillaries. The transduction of signals from the extracellular milieu of the endothelial cell to the nucleus is a receptor-mediated event. Some of the receptors that mediate critical events in angiogenesis are receptor tyrosine kinases (RTKs). Receptor tyrosine kinases, also known as growth factor receptors, are a family of transmembrane proteins with a large extracellular ligand binding domain, a transmembrane domain, and an intracellular domain with intrinsic tyrosine kinase activity. (See also, Plowman, et al., *DN&P* 1994, 7, 334–339).

One of the results of tyrosine kinase signal transduction is cell proliferation. Normal cell proliferation is a key physiological process in healthy organisms. However, a number of diseases and disorders are the result of dysfunctional cell proliferation. Included in the diseases resulting from abnormal cell proliferation are blood vessel proliferative disorders referred to as angiogenesis and/or vasculogenesis.

Angiogenesis refers to the process of new capillary formation into tissue or organs and occurs in a number of physiological processes, both normal and pathological. Normal angiogenesis is associated with corpus luteum formation, and fetal and embryonic development. A number of serious diseases are associated with persistent, unregulated angiogenesis. These diseases are dominated by abnormal neovascularization. Included in the diseases in which unregulated angiogenesis is present are rheumatoid arthritis and endometriosis.

Arthritis is a serious health care problem. Progressive arthritic conditions in humans cause severe pain, loss of joint mobility and disfigurement, and an overall reduction in the quality of life. In rheumatoid arthritis, the synovium hyperproliferates (aided by new blood vessels) and invades the cartilage which is destroyed. Conventional treatment for rheumatoid arthritis includes non-steroidal anti-inflammatory drugs (NSAEDs). A need exists for an effective treatment for rheumatoid arthritis that will disrupt disease progression in addition to suppression or amelioration of symptoms. Inhibition of new capillary formation could lessen the joint destruction that occurs in rheumatoid arthritis and halt disease progression.

Endometriosis, the presence of functional endometrium outside of the uterine cavity, is a common disease, causing abdominal pain, dysmenorrhea, dyspareunia and infertility in about 10% of the female population. It is believed to arise from the implantation and growth of exfoliated menstrual endometrium on the peritoneal and ovarian surfaces (Thomas & Prentice, *Reprod. Med. Rev.*, 1992, 1, 21–36). Active endometriotic explants have pronounced vascularization both within and around the tissue (Nisolle, et al., *Fertil. Steril.*, 1993, 59, 681–684), due to the development of new blood vessels through angiogenesis. Current therapeutic strategies range from observation in mild cases to a complete hysterectomy in painful or advanced cases, and includes treatment with hormones to modulate the steroidal support assumed to be needed for the maintenance of ectopic endometrium (Lu & Ory, *Mayo Clin. Proc.*, 1995, 70, 453–463). However, hormone treatments-are not ideal and are not curative (Shaw, *Drug Safety*, 1994, 11, 104–113). New treatments that are more effective and have fewer side-effects are needed.

Despite the significant progress that has been made in developing treatments for angiogenic diseases and disorders, there remains a need in the art for new methods of treatment.

SUMMARY OF THE INVENTION

A number of receptor tyrosine kinases are thought to be involved in angiogenesis, either directly or indirectly. Of particular interest are Flt-1 and Flk-1, receptors for VEGF. Flt-1 and Flk-1 are also known as VEGFR1 and VEGFR2, respectively, and the human homologue of Flk-1 is KDR. These receptors are expressed primarily on endothelial cells and play a direct role in angiogenesis. Other RTKs of potential interest in angiogenesis include the platelet-derived growth factor (PDGF) receptor and the fibroblast growth factor (FGF) receptor family. Although they have also been implicated in angiogenesis, they have broader expression patterns which encompass cell types other than endothelial cells, and a broader range of physiological functions.

The present invention is directed to methods for modulating processes mediated by protein tyrosine kinases. More particularly, the invention relates to methods of treatment which interrupt protein kinase signal transduction thereby blocking abnormal cell proliferation. Moreover, the invention is directed to methods of treating disorders and diseases related to abnormal cell proliferation by the use of specific tyrosine kinase inhibitors.

Unregulated blood vessel growth, due to angiogenesis and vascularization, which is at least in part responsible for diseases and disorders such as rheumatoid arthritis, endometriosis, ocular diseases, cancer and metastases, psoriasis, arterial thickening and restenosis, and excessive scarring during wound healing, is dependent on phosphorylation of substrate molecules by activated tyrosine kinases. The methods of the invention can minimize angiogenesis and vascularization of tissues by specifically inhibiting the activity of protein kinases, which regulate proliferation of blood vessels during angiogenesis. This inhibition can result in a blockade to tyrosine signal transduction and an interruption of abnormal cell proliferation and thus disease progression. Alternatively, as in the case of tissue ischemia, it may be useful to increase the activity of protein kinases in order to increase the proliferation of blood vessels through angiogenesis.

A first aspect of the invention features a method of modulating cell proliferation, comprising administering to a patient in need of such treatment a pharmaceutically acceptable composition comprising a therapeutically effective amount of one or more indolinone compounds of Formula I:

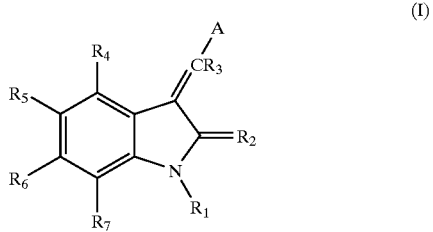

(I)

$R_1$ is H or alkyl; $R_2$ is O or S; $R_3$ is H;

$R_4$, $R_5$, $R_6$, and $R_7$ are each independently selected from the group consisting of hydrogen alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, CONRR', and $(CH_2)_nONRR'$;

A is selected from the group consisting of a 4,5,6,7-tetrahydroindole and a five-membered heteroaryl ring, where the five-membered ring is selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, where the five-membered ring and the tetrahydroindole are optionally substituted with one or more substituents selected from the group consisting of alkyl, alkoxy, aryl, aryloxy, alkaryl, alkaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, CONRR', and $(CH_2)_nONRR'$;

n is 0–3;

R is selected from the group consisting of H, alkyl, and aryl; and R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, $NO_2$, and $(CH_2)_nCO_2R$.

The term "modulate" as used herein in reference to the abnormal cell proliferation refers to the ability of a compound to increase or decrease the amount of cell proliferation presumably by altering the effect of the presence of VEGF, FGF, and/or PDGF on cells, or preferably on receptors, or more preferably on tyrosine kinases and the tyrosine kinase signal cascade. The "activity" of VEGF, FGF, and/or PDGF on cells is to "stimulate" cell proliferation, both normal and abnormal, presumably by binding to receptors and through the activity of tyrosine kinase and tyrosine kinase signal transduction.

The term "abnormal cell proliferation" or "cell proliferative disorder" as used herein refers to a disorder where an excess cell proliferation of one or more subset of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the affected cells. Hyper-proliferative cell disorders include cancer and metastases, autoimmune disorders, rheumatoid arthritis, endometriosis, ocular disease, arterial thickening and restenosis, inflammatory disorders such as psoriasis, and fibrotic disorders, such as aberrant wound healing.

In reference to the treatment of abnormal cell proliferative conditions, a therapeutic effect refers to one or more of the following: (a) a reduction in hyperproliferation; (b) inhibition of hyperproliferation; (c) inhibition (i.e., slowing or stopping) of tumor metastasis; and (d) relieving to some extent one or more of the symptoms associated with the abnormal condition.

The term "signal transduction" as used herein refers to a fundamental mechanism whereby external stimuli that regulate diverse cellular processes are relayed to the interior of cells. One of the key biochemical mechanisms of signal transduction involves the reversible phosphorylation of proteins by kinases, which enables regulation of the activity of mature proteins by altering their structure and function. The protein kinases involved in signal transduction include tyrosine kinases which phosphorylate proteins on the alcohol moiety of tyrosine residues, and serine/threonine kinases which phosphorylate on serine/threonine residues.

Further, the term "signal transduction pathway" refers to the molecules that propagate an extracellular signal through the cell membrane to become intracellular signals. These signals can then stimulate a cellular response. The polypeptide molecules involved in signal transduction processes are typically receptor and non-receptor protein kinases, receptor and non-receptor protein phosphatases, adaptor molecules, nucleotide exchange factors, and transcription factors.

The term "administering" relates to a method of incorporating a compound into cells or tissues of an organism. An abnormal condition can be prevented or treated when the cells or tissues of the organism exist within the organism or outside of the organism. Cells existing outside the organism can be maintained or grown in cell culture dishes. For cells harbored within the organism, many techniques exist in the art to administer compounds, including (but not limited to)

oral, parenteral, dermal, intramuscular, and aerosol applications. For cells outside of the organism, multiple techniques exist in the art to administer the compounds, including (but not limited to) cell microinjection techniques, carrier techniques, and passive diffusion.

The term "abnormal condition" refers to a function in the cells or tissues of a patient that deviates from their normal functions in that patient, or from their normal function in the general population. The presence of an abnormal condition can be determined by methods standard in the art. An abnormal condition can relate to cell proliferation as described herein.

The term "composition" as used herein refers to one or more indolinone compounds of the invention together with other chemical components or excipients, such as solvents, diluents or carriers. The pharmaceutical composition facilitates administration of the compound to an organism.

Formulations for indolinone compounds are described in U.S. application Ser. No. 08/702,232, filed Aug. 23, 1996 and in the corresponding International patent publication WO 96/22976. Specific examples of parenteral and oral formulations for lipophilic compounds are contained in U.S. Pat. No. 5,610,173, issued Mar. 11, 1997, entitled "Formulations for Lipophilic Compounds" by D. Schwartz, et al. and U.S. patent application Ser. No. 09/034,374, filed Mar. 4, 1998, entitled "Formulations for Hydrophobic Pharmaceutical Composition" by N. Shenoy, et al. and PCT Application No. PCT/US98/04134, filed Mar. 4, 1998, entitled "Formulations for Hydrophobic Pharmaceutical Compositions" by N. Shenoy, et al., which are hereby included herein by reference in their entirety, including any drawings, figures, and tables.

The term "solvent" as used herein refers to a chemical compound that facilitates the solubilization of compounds. Examples of solvents include, but are not limited to, pharmaceutically acceptable alcohols, such as ethanol; polyoxyhydrocarbyl compounds, such as poly(ethylene glycol); pharmaceutically acceptable surfactants such as CREMOPHOR EL®; polyglycolized lipids, such as GELUCIRE® and LABRASOL®; and pharmaceutically acceptable oils, such as miglyol 812.

The term "pharmaceutically acceptable alcohol" as used herein refers to alcohols which are liquids at about room temperature (approximately 20 C). These include propylene glycol, ethanol, 2-(2-ethoxyethoxy)ethanol (TRANSCUTOL®, Gattefosse, Westwood, N.J. 07675), and glycerol.

The term "pharmaceutically acceptable" or "pharmaceutical" as used herein refers to solutions or components of the formulation that do not prevent the therapeutic compound from exerting a therapeutic effect and do not cause unacceptable adverse side effects. Examples of pharmaceutically acceptable reagents are provided in *The United States Pharmacopeia The National Formulary*, United States Pharmacopeial Convention, Inc., Rockville, Md. 1990 (hereby incorporated by reference herein, including any drawings, figures, or tables). Unacceptable side effects vary for different diseases. Generally, the more severe the disease the more toxic the effects that will be tolerated. Unacceptable side effects for different diseases are known in the art.

The term "polyoxyhydrocarbyl compound" as used herein refers to a water soluble carbohydrate such as glucose, sucrose, maltotriose, and the like; water soluble carbohydrate derivatives such as gluconic acid and mannitol, and oligosaccharides; and water soluble polymers such as polyvinylpyrrolidone, poly(vinyl alcohol), and in particular, polyethers such as other polyoxyalkylenes including poly (ethylene glycol) or other water soluble mixed oxyalkylene polymers and the polymeric form of ethylene glycol. Although polyoxyhydrocarbyl compounds preferably contain more than one carbon, oxygen, and hydrogen atom, some molecules such as poly(ethylene imine) are also included.

A particularly preferred class of solubilizing polyoxyhydrocarbyl moieties comprises poly(ethylene glycol) (PEG) and PEG derivatives, such as PEG monomethyl ether. Other suitable PEG derivatives include PEG-silicon derived ethers. Many of these polymers are commercially available in a variety of molecular weights. Others may be conveniently prepared from commercially available materials, such as by coupling of amino-PEG moiety to a haloalkyl silyl or silane moiety.

Suitable PEGs may vary in molecular weight from about 200 g/mol to about 20,000 g/mol or more, more preferably 200 g/mol to 5,000 g/mol, even more preferably 250 g/mol to 1,000 g/mol, and most preferably 250 g/mol to 500 g/mol. The choice of a particular molecular weight may depend on the particular indolinone compound chosen and its molecular weight and degree of hydrophobicity, as well as the particular application for which the formulation is to be used.

The term "pharmaceutically acceptable surfactant" as used herein refers to a compound that can solubilize or aid in solubilization of indolinone compounds into aqueous solutions. Preferably for parenteral formulations, the surfactant is a non-ionic surfactant. Examples of pharmaceutically acceptable surfactants include POLYSORBATE 80® and other polyoxyethylene sorbitan fatty acid esters, glyceryl monooleate, polyvinyl alcohol, ethylene oxide copolymers such as PLURONIC® (a polyether) and TETRONIC® (BASF), polyol moieties, and sorbitan esters. Preferably ethoxylated castor oils, such as CREMOPHOR® EL, are used for the formulation of indolinone compounds.

The term "ethoxylated castor oil" as used herein refers to castor oil that is modified with at least one oxygen containing moiety. In particular the term refers to castor oil comprising at least one ethoxyl moiety.

Further, the term "pharmaceutically acceptable surfactant" as used herein in reference to oral formulations, includes pharmaceutically acceptable non-ionic surfactants (for example polyoxyethylenepolypropylene glycol, such as POLOXAMER® 68 (BASF Corp.) or a mono fatty acid ester of polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), polyoxyethylene (20) sorbitan monolaurate (TWEEN® 20) and the like); polyoxyethylene castor oil derivatives (for example, polyoxyethyleneglycerol-triricinoleate or polyoxyl 35 castor oil (CREMOPHOR® EL, BASF Corp.), polyoxyethyleneglycerol oxystearate (CREMOPHOR® RH 40 (polyethyleneglycol 40 hydrogenated castor oil) or CREMOPHOR® RH 60 (polyethyleneglycol 60 hydrogenated castor oil), BASF Corp.) and the like); or a pharmaceutically acceptable anionic surfactant.

The term "polyglycolized lipids" as used herein refers to mixtures of monoglycerides, diglycerides, or triglycerides and polyethyleneglycol monoesters and diesters formed by the partial alcoholysis of vegetable oil using PEG of 200 g/mol to 2,000 g/mol or by the esterification of fatty acids using PEG 200 g/mol to 2,000 g/mol and glycerols. Preferably these include GELUCIRE® 35/10, GELUCIRE® 44/14, GELUCIRE® 46/07, GELUCIRE® 50/13, GELUCIRE® 53/10, and LABRASOL®.

The term "pharmaceutically acceptable oils" as used herein refers to oils such as mineral oil or vegetable oil (including safflower oil, peanut oil, and olive oil), fractionated coconut oil, propylene glycol monolaurate, mixed triglycerides with caprylic acid and capric acid, and the like. Preferred embodiments of the invention feature mineral oil, vegetable oil, fractionated coconut oil, mixed triglycerides with caprylic acid, and capric acid. A highly preferred embodiment of the invention features Miglyol 812 (available from Huls America, USA).

The term "carrier" as used herein refers to a chemical compound that facilitates the incorporation of a compound into cells or tissues. For example dimethyl sulfoxide (DMSO) is a commonly utilized carrier as it facilitates the uptake of many organic compounds into the cells or tissues of an organism. The use of liposomes is also specifically envisioned.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffered salts can control the pH of a solution at low concentrations, a buffered diluent rarely modifies the biological activity of a compound.

The term "indolinone" is used as that term is commonly understood in the art, and includes a large subclass of substituted or unsubstituted compounds that are capable of being synthesized from an aldehyde moiety and an oxindole moiety.

The term "oxindole" refers to an oxindole compound substituted with chemical substituents. Oxindole compounds are of the general structure:

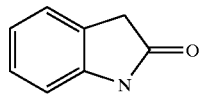

The term "substituted" refers to compounds of the invention that are derivatized with any number of chemical substituents, typically by replacing one or more of the hydrogen atoms present in the compound's general structure.

The term "compound" refers to the compound or a pharmaceutically acceptable salt, ester, amide, prodrug, isomer, or metabolite, thereof.

The term "pharmaceutically acceptable salt" refers to a formulation of a compound that does not abrogate the biological activity and properties of the compound. Pharmaceutical salts can be obtained by reacting a compound of the invention with inorganic or organic acids such as hydrochloric acid, hydrobromic acid, sulfuric acid, nitric acid, phosphoric acid, methane sulfonic acid, ethane sulfonic acid, p-toluene sulfonic acid, salicylic acid and the like. Also specifically envisioned are salts of free acids.

The term "ester" refers to a chemical moiety with formula —(R)$_n$—COOR', where R and R' are independently selected from the group consisting of saturated or unsaturated alkyl and homocyclic or heterocyclic ring moieties and where n is 0 or 1.

The term "amide" refers to a chemical substituent of formula —NHCOR, where R is selected from the group consisting of hydrogen, alkyl, hydroxyl, and homocyclic or heterocyclic ring moieties, where the ring is optionally substituted with one or more substituents independently selected from the group consisting of alkyl, halogen, trihalomethyl, carboxylate, nitro, or ester.

The term "prodrug" refers to an agent that is converted into the parent drug in vivo. Prodrugs may be easier to administer than the parent drug in some situations. For example, the prodrug may be bioavailable by oral administration but the parent is not, or the prodrug may improve solubility to allow for intravenous administration.

The term "saturated alkyl" refers to an alkyl moiety that does not contain any alkene or alkyne moieties. The alkyl moiety may be branched or non-branched.

The term "unsaturated alkyl" refers to an alkyl moiety that contains at least one alkene or alkyne moiety. The alkyl moiety may be branched or non-branched.

The term "aromatic" refers to an aromatic group which has at least one ring having a conjugated pi electron system and includes both carbocyclic aryl (e.g. phenyl) and heterocyclic aryl groups (e.g. pyridine). The term "carbocyclic" refers to a compound which contains one or more covalently closed ring structures, and in which the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "aliphatic ring" refers to a compound which contains one or more covalently closed ring structures, and in which at least one of the atoms forming the backbone is a saturated carbon atom (e.g. cyclohexane). The term "heteroaliphatic ring" refers to a ring system in which at least one of the atoms forming the backbone is a heteroatom (e.g. tetrahydropyran).

The term "amine" refers to a chemical moiety of formula NR$_1$R$_2$ where R$_1$ and R$_2$ are independently selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "halogen" refers to an atom selected from the group consisting of fluorine, chlorine, bromine, and iodine. The term "trihalomethyl" refers to the —CX$_3$ group, where X is a halogen.

The term "ketone" refers to a chemical moiety with formula —(R)$_n$—CO—R', where R and R' are selected from the group consisting of saturated or unsaturated alkyl and five-membered or six-membered aryl or heteroaryl moieties and where n is 0 or 1.

The term "carboxylic acid" refers to a chemical moiety with formula —(R)$_n$—COOH, where R is selected from the group consisting of saturated or unsaturated alkyl and five-membered or six-membered aryl or heteroaryl moieties and where n is 0 or 1.

The term "alcohol" refers to a chemical substituent of formula —ROH, where R is selected from the group consisting of hydrogen, saturated or unsaturated alkyl, and five-membered or six-membered aryl or heteroaryl ring moieties, where the ring is optionally substituted with one or more substituents independently selected from the group consisting of alkyl, halogen, trihalomethyl, carboxylate, nitro, and ester moieties.

The term "alkoxyalkyl moiety" refers to a chemical substituent of formula —(R)$_n$—OR', where R' is an optionally substituted saturated or unsaturated alkyl moiety or an optionally substituted ring and n is 0 or 1, and where R' is an optionally substituted alkyl or optionally substituted aromatic, heteroaromatic, aliphatic, or heteroaliphatic ring moieties. When n is 0, then the alkoxyalkyl moiety is called an "alkoxy moiety".

The term "aldehyde" refers to a chemical moiety with formula —$(R)_n$—CHO, where R is selected from the group consisting of saturated or unsaturated alkyl and five-membered or six-membered aryl or heteroaryl moieties and where n is 0 or 1.

The term "sulfone" refers to a chemical moiety with formula —$SO_2$—R, where R is selected from the group consisting of saturated or unsaturated alkyl and five-membered or six-membered aryl or heteroaryl moieties.

The term "thiol" refers to a chemical moiety with formula —$(R)_n$—SH, where R is selected from the group consisting of optionally substituted alkyl or optionally substituted aromatic, heteroaromatic, aliphatic, or heteroaliphatic ring moieties and where n is 0 or 1. The term "thioether" refers to a chemical moiety of the formula —$(R)_n$—SR' where both R and R' are selected from the group consisting of optionally substituted alkyl or optionally substituted aromatic, heteroaromatic, aliphatic, or heteroaliphatic ring moieties and where n is 0 or 1.

The term "acyl" refers to chemical moieties of the general formula —C(O)R. When R is hydrogen the molecule containing the acyl group is an aldehyde. When R is an alkyl, an aliphatic ring, or an aromatic ring, then the molecule containing the acyl group is a ketone.

In preferred embodiments of the methods of modulating abnormal cell proliferation, the composition consists of compounds of Formula I, where A is selected from the group consisting of pyrrole, thiophene, and 4,5,6,7-tetrahydroindole, optionally substituted with one or more substituents selected from the group consisting of alkyl, alkoxy, aryl, aryloxy, alkaryl, alkaryloxy, halogen, trihalomethyl, S(O)R, $SO_2$NRR', $SO_3$R, SR, $NO_2$, NRR', OH CN, C(O)R, OC(O)R, NHC(O)R, $(CH_2)_n CO_2 R$, CONRR', and $(CH_2)_n$ONRR; n is 0–3; R is selected from the group consisting of H, alkyl, and aryl; and R' is selected from the group consisting of H, alkyl, and aryl, wherein the alkyl is optionally substituted with a six-membered heteroaliphatic ring, and where the six-membered ring is optionally substituted at one or more positions with substituents selected from the group consisting of alkyl, alkoxy, halogen, trihalomethyl, $NO_2$, and $(CH_2)_n CO_2 R$. In particularly preferred embodiments, A is pyrrole. In other preferred embodiments, indolinone compounds of Formula I are preferably selected from the group consisting of Compound II, Compound III, Compound IV, Compound V, Compound VI, Compound VII, and Compound VIII.

By "Compound II" is meant either the E or Z isomer of the indolinone compound, 5-amino-3-(3,5-diethyl-1H-pyrrol-2-ylmethylene)-1,3-dihydro-indol-2-one.

By "Compound III" is meant either the E or Z isomer of the indolinone compound, 4-methyl-3-(3-methyl-thiophen-2-ylmethylene)-1,3-dihydro-indol-2-one.

By "Compound IV" is meant either the E or Z isomer of the indolinone compound, 5-chloro-3-(3,5-dimethyl-1H-pyrrol-2-ylmethylene)-1,3-dihydro-indol-2-one.

By "Compound V" is meant either the E or Z isomer of the indolinone compound, 3-[4-methyl-5-(2-oxo-1,2-dihydro-indol-3-ylidenemethyl)-H-pyrrol-3-yl]-propionic acid.

By "Compound VI" is meant the indolinone compound, 3-[2,4-dimethyl-5-(2-oxo-1,2-dihydro-indol-3-ylidenemethyl)-1H-pyrrol-3-yl]-propionic acid.

By "Compound VII" is meant either the E or Z isomer of the indolinone compound, N-(2-Morpholin-4-yl-ethyl)-3-[2-(2-oxo-1,2-dihydro-indol-3-ylidenemethyl)-4,5,6,7-tetrahydro-1H-indol-3-yl]-propionamide.

By "Compound VIII" is meant either the E or Z isomer of the indolinone compound, 3-[2-(2-Oxo-1,2-dihydro-indol-3-ylidenemethyl)-4,5,6,7-tetrahydro-1H-indol-3-yl]-propionic acid.

By the term "E or Z isomer" as used herein refers to the positioning of the two atoms or groups for each doubly-bonded carbon atom compared with the positioning of the two atoms or groups for the other doubly-bonded carbon. The priority of the two atoms or groups is identified for each doubly-bonded carbon atom, and then the positioning relative to each other is determined, i.e. whether the higher priority atoms or groups for each doubly-bonded carbon atom are on the same or opposite sides. By Z is meant on the same side, and by E, on the opposite side. "Priority" refers to atomic number, with the atom of higher atomic weight getting the higher priority. If two atoms are isotopes of the same element, the atom of higher mass number has the higher priority. If the relative priority of the two groups attached to the doubly-bonded carbon cannot be decided, a similar comparison is made with the atoms attached to these groups, and so on.

In other preferred embodiments of the methods of modulating abnormal cell proliferation, the composition further comprises one or more pharmaceutically acceptable excipients in a formulation, where the formulation is selected from the group consisting of, but not limited to, a parenteral, a topical and an oral formulation. The effective amount of the compound in the composition comprises 1 to 1000 mg/m$^2$/day, preferably 10 to 500 mg/m$^2$/day, and most preferably 10 to 250 mg/m$^2$/day of one or more indolinone compounds. Preferably the patient is a mammal; more preferably the mammal is a human. Alternatively, the mammal can be a rat, in which case altered activity of VEGF, FGF, and/or PDGF can be induced.

The term "mammal" as used herein preferably refers to such organisms as mice, rats, rabbits, guinea pigs, goats, sheep, horses, and cows, for example; more preferably to dogs, cats, monkeys, and apes; and most preferably to humans.

Another aspect of the invention features methods of modulating the activity of VEGF, FGF, and/or PDGF on cells in vitro, or more preferably, in vivo, comprising administering to said cells a pharmaceutically acceptable composition comprising a therapeutic amount of one or more indolinone compounds of Formula I:

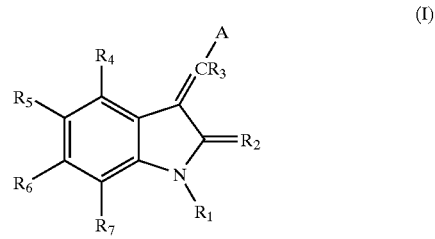

(I)

$R_1$ is H or alkyl; $R_2$ is O or S; $R_3$ is H;

$R_4$, $R_5$, $R_6$, and $R_7$ are each independently selected from the group consisting of hydrogen alkyl, alkoxy, aryl, aryloxy, alkaryl, alkaryloxy, halogen, trihalomethyl, S(O)R, $SO_2$NRR', $SO_3$R, SR, $NO_2$, NRR', OH, CN, C(O)R, OC(O)R, NHC(O)R, $(CH_2)_n CO_2 R$, CONRR', and $(CH_2)_n$ONRR';

A is selected from the group consisting of a 4,5,6,7-tetrahydroindole and a five-membered heteroaryl ring, where the five-membered ring is selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, where the five-membered ring and the tetrahydroindole are optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R.

The term "modulate" as used herein in reference to the activity of VEGF, FGF, and/or PDGF refers to the ability of a compound to alter the effect of the presence of VEGF, FGF, and/or PDGF on cells, or more preferably, on receptors, or more preferably on tyrosine kinases and the tyrosine kinase signal cascade. The "activity" of VEGF, FGF, and/or PDGF on cells is to "stimulate" cell proliferation, both normal and abnormal, presumably by binding to receptors and through the activity of tyrosine kinase and tyrosine kinase signal transduction.

The term "VEGF" as used herein refers to any member of the vascular endothelial growth factor family as well as splice variants and isoforms. The term "VEGF-R" refers to all receptors that bind VEGF or VEGF family members, splice variants or isoforms. Detailed information regarding VEGF family members, splice variants, and isoforms and VEGF receptors is provided in the Description of the Invention, herein, in Section I and Section II, respectively.

The term "FGF" as used herein refers to any member of the fibroblast growth factor family. The term "FGF-R" refers to all receptors that bind members of the FGF growth factor family. Detailed information regarding FGF family members and FGF receptors is provided in the Description of the Invention, herein, in Section I and Section II, respectively.

The term "PDGF" as used herein refers to any isoform of platelet derived growth factor. The term "PDGF-R" refers to all receptors that bind to any isoform of PDGF. Detailed information regarding PDGF isoforms and receptors is provided in the Description of the Invention, herein, in Section I and Section II, respectively.

In preferred embodiments of the methods of modulating the activity of VEGF, FGF, or PDGF on cells, the composition consists of compounds of Formula I, where A is selected from the group consisting of thiophene, pyrrole, and 4,5,6,7-tetrahydroindole, optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH CN, C(O)R, OC(O)R, NHC(O)R, (CH$_2$)$_n$CO$_2$R, CONRR', and (CH$_2$)$_n$ONRR'; n is 0–3; R is selected from the group consisting of H, alkyl, and aryl; and R' is selected from the group consisting of H, alkyl, and aryl, wherein the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R. In other embodiments indolinone compounds of Formula I are preferably selected from the group consisting of Compound II, Compound III, Compound IV, Compound V, Compound VI, Compound VII, and Compound VIII.

In other preferred embodiments of the methods of modulating the activity of VEGF, FGF, or PDGF on cells, the composition further comprises one or more pharmaceutically acceptable excipients in the formulation. Preferably, the formulation is selected from the group consisting of a parenteral, an oral, and a topical formulation and the effective amount of the compound in the composition comprises 1 to 1000 mg/m$^2$/day, preferably 10 to 500 mg/m$^2$/day, and most preferably 10 to 250 mg/m$^2$/day of one or more indolinone compounds. Preferably the patient is a mammal; more preferably the mammal is a human. Alternatively, the mammal can be a rat, in which case altered activity of VEGF, FGF, and/or PDGF can be induced.

The invention also features in another aspect, methods of modulating tyrosine kinase signal transduction, comprising administering to a patient in need of such treatment a pharmaceutically acceptable composition comprising a therapeutically effective amount of one or more indolinone of Formula I:

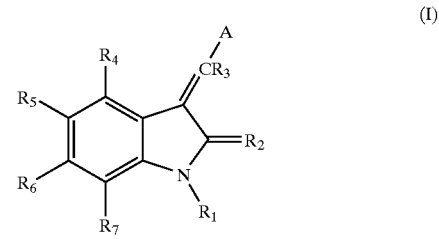

(I)

R$_1$ is H or alkyl; R$_2$ is O or S; R$_3$ is H;

R$_4$, R$_5$, R$_6$, and R$_7$ are each independently selected from the group consisting of hydrogen alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_3$)$_n$ONRR';

A is selected from the group consisting of a 4,5,6,7-tetrahydroindole and a five-membered heteroaryl ring, where the five-membered ring is selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadaizole, 1,2,3,4-thiatriazole, 1,2,3,5-thiatriazole, and tetrazole, where the five-membered ring and the tetrahydroindole are optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, $NO_2$, and $(CH_2)_nCO_2R$.

The term "modulate" as used herein in reference to tyrosine kinase signal transduction refers to the ability of a compound to alter the function of tyrosine kinase in vitro and/or in vivo. A modulator preferably activates or inhibits the activity of tyrosine kinase depending on the concentration of the compound exposed to tyrosine kinase.

The term "activates" as used herein in reference to tyrosine kinase activity refers to increasing the cellular activity of tyrosine kinase. The term "inhibit" refers to decreasing the cellular activity of tyrosine kinase. Tyrosine kinase activity is preferably in signal transduction.

The term "modulates" also refers to altering the function of tyrosine kinase by increasing or decreasing the probability that signal transduction occurs. A modulator preferably increases the probability that signal transduction occurs, or decreases the probability that signal transduction occurs.

In preferred embodiments of the methods of modulating tyrosine kinase signal transduction, the composition consists of compounds of Formula I, where A is selected from the group consisting of thiophene, pyrrole, and 4,5,6,7-tetrahydroindole, optionally substituted with one or more substituents selected from the group consisting of alkyl, alkoxy, aryl, aryloxy, alkaryl, alkaryloxy, halogen, trihalomethyl, S(O)R, $SO_2NRR'$, $SO_3R$, SR, $NO_2$, NRR', OH CN, C(O)R, OC(O)R, NHC(O)R, $(CH_2)_nCO_2R$, CONRR', and $(CH_2)_nONRR$; n is 0–3; R is selected from the group consisting of H, alkyl, and aryl; and R' is selected from the group consisting of H, alkyl, and aryl, wherein the alkyl is optionally substituted with a six-membered heteroaliphatic ring, and where the six-membered ring is optionally substituted at one or more positions with substituents selected from the group consisting of alkyl, alkoxy, halogen, trihalomethyl, $NO_2$, and $(CH_2)_nCO_2R$. In other embodiments indolinone compounds of Formula I are preferably selected from the group consisting of Compound II, Compound III, Compound IV, Compound V, Compound VI, Compound VII, and Compound VIII.

In other preferred embodiments of the methods of modulating tyrosine kinase signal transduction, the composition further comprises one or more pharmaceutically acceptable excipients in the formulation. Preferably, the formulation is selected from the group consisting of a parenteral, an oral, and a topical formulation and the effective amount of the compound in the composition comprises 1 to 1000 mg/m²/day, preferably 10 to 500 mg/m²/day, and most preferably 10 to 250 mg/m²/day of one or more indolinone compounds selected from the group consisting of Compound II, Compound III, and Compound IV. Preferably the patient is a mammal; more preferably the mammal is a human. Alternatively, the mammal can be a rat, in which case altered activity of VEGF, FGF, and/or PDGF can be induced.

Another aspect of the invention features methods of identifying one or more indolinone compounds that inhibit growth factor-stimulated cell proliferation comprising the following steps; (a) contacting cells with one or more indolinone compounds of Formula I; (b) contacting the cells with one or more growth factors selected from the group consisting of VEGF, PDGF, and FGF; and (c) monitoring an effect upon the cells. Preferably, the growth factor is VEGF and the cells are endothelial cells, or PDGF and the cells are smooth muscle cells, or FGF and the cells are endothelial cells. Preferably, the effect is monitored calorimetrically, for example using a change in absorbance.

The term "contacting" as used herein refers to mixing a solution comprising one or more indolinone compounds or other compounds such as VEGF, FGF, or PDGF with a liquid medium bathing the cells of the methods. The solution comprising the compound may also comprise other components, such as dimethyl sulfoxide (DMSO), which facilitates the uptake of indolinone compounds into the cells of the methods. The solution comprising the compounds may be added to the medium bathing the cells by utilizing a delivery apparatus, such as a pipet-based device or a syringe-based device.

The indolinone compounds of the invention preferably modulate the activity of the protein tyrosine kinase in vitro. These compounds preferably show positive results in one or more in vitro assays for an activity corresponding to treatment of the disease or disorder in question (such as the assays described in the Examples below).

The term "monitoring" refers to observing the affect of adding the compound to the cells of the method. The effect can be manifested in a change in cell phenotype, cell proliferation, protein kinase catalytic activity, or in the interaction between a protein kinase and a natural binding partner. The term "effect" describes a change or an absence of a change in cell phenotype or cell proliferation; a change or an absence of a change in the catalytic activity of the protein kinase; or a change or an absence of a change in an interaction between the protein kinase and a natural binding partner. In preferred embodiments, the effect can be monitored calorimetrically, for example, using change in absorbance. These methods are standard in the art and typically involve the addition of a colorimetric reagent followed by spectrophotometric monitoring of a change in the protein.

The invention also features methods of identifying one or more indolinone compounds that inhibit platelet-derived growth factor-stimulated cell proliferation comprising the following steps: (a) contacting cells with one or more indolinone compounds of Formula I; (b) contacting the cells with platelet-derived growth factor; and (c) monitoring an effect upon the cells. Preferably, the cells are smooth muscle cells and the effect is monitored calorimetrically, for example, using change in absorbance.

The invention also features methods of identifying one or more indolinone compounds that are active in an adjuvant arthritis model in rats comprising the following steps: (a) administration of one or more indolinone compounds of Formula I to the rats; and (b) monitoring an effect upon the rats. Preferably, the compounds are administered at a concentration of 1 to 1000 mg/m²/day, preferably 10 to 500 mg/m²/day, and most preferably 10 to 250 mg/m²/day of one or more indolinone compounds and the effect on the rats' disease is selected from the group consisting of ear nodulation, tail nodulation, nose swelling, paw swelling, and balanitis.

The term "adjuvant arthritis model" is used herein to refer to rats, preferably Wistar-Lewis or other rat strains commonly known to those skilled in the art, in which disease was induced by injecting 0.1 mL Freund's adjuvant into the base of the tail. This adjuvant arthritis model is only one example of an animal model that can be used to test the compounds of the invention. For a review of the three most common animal models, see Oliver & Brahn (1996) J. Rheumatol. 23:56–60, hereby enclosed herein by reference in its entirety, including any drawings, figures, or tables.

The term "monitoring" is further used herein in reference to an effect on rats in the adjuvant arthritis model to include general disease symptoms including ear nodulation, tail nodulation, nose swelling, paw swelling, and balanitis. An arthritis index can be calculated from these measurements as defined in the Examples section.

An additional aspect of the invention features methods of modulating abnormal cell proliferation, the activity of VEGF, FGF, or PDGF on cells in vivo or in vitro, or tyrosine kinase signal transduction, comprising administering to a patient in need of such treatment a pharmaceutically acceptable composition comprising a therapeutically effective amount of one or more indolinone compounds of Formula I identified by their ability to inhibit VEGF-, FGF-, or PDGF-stimulated cell proliferation, or inhibit one or more of the effects of adjuvant arthritis in rats. Preferably, the compounds are administered in a composition that further comprises one or more pharmaceutically acceptable excipients in a formulation that can be, but is not limited to being, administered orally, parenterally, or topically. The compounds may be administered at a concentration comprising 1 to 1000 mg/m$^2$/day, preferably 10 to 500 mg/m$^2$/day, and most preferably 10 to 250 mg/m$^2$/day of one or more indolinone compounds, preferably to a mammal, and more preferably to a human.

A final aspect of the invention features methods of treating or preventing an abnormal condition by administering to a patient in need of such treatment a pharmaceutically acceptable composition comprising a therapeutically effective amount of one or more indolinone compounds of Formula I:

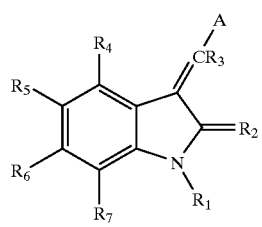

(I)

$R_1$ is H or alkyl; $R_2$ is O or S; $R_3$ is H;

$R_4$, $R_5$, $R_6$, and $R_7$ are each independently selected from the group consisting of hydrogen alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

A is selected from the group consisting of a 4,5,6,7-tetrahydroindole and a five-membered heteroaryl ring, where the five-membered ring is selected from the group consisting of thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadaizole, 1,2,3,4-thiatriazole, 1,2,3,5-thiatriazole, and tetrazole, where the five-membered ring and the tetrahydroindole are optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R, where the abnormal condition is selected from the group consisting of arthritis, endometriosis, ocular neovascularization, solid tumor growth and metastases, and excessive scarring during wound healing.

In preferred embodiments of methods of treating or preventing an abnormal condition, the composition consists of compounds of Formula I, where A is selected from the group consisting of thiophene, pyrrole, and 4,5,6,7-tetrahydroindole, optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH CN, C(O)R, OC(O)R, NHC(O)R, (CH$_2$)$_n$CO$_2$R, CONRR', and (CH$_2$)$_n$ONRR; n is 0–3; R is selected from the group consisting of H, alkyl, and aryl; and if R' is selected from the group consisting of H, alkyl, and aryl, wherein the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R. In other embodiments indolinone compounds of Formula I are preferably selected from the group consisting of Compound II, Compound III, Compound IV, Compound V, Compound VI, Compound VII, and Compound VIII.

Additional methods of treating or preventing an abnormal condition include, administering to a patient in need of such treatment a pharmaceutically acceptable composition comprising a therapeutically effective amount of one or more compounds identified by previously described methods for identifying compounds that modulate VEGF-, FGF-, or PDGF-activity, or that are active in an adjuvant arthritis model in rats, where the abnormal condition is selected from the group consisting of rheumatoid arthritis, endometriosis, ocular diseases, cancer and metastases, psoriasis, arterial thickening and restenosis, tissue ischemia, and excessive scarring during wound healing. The disease is preferably endometriosis or rheumatoid arthritis, and the composition further comprises one or more pharmaceutically acceptable excipients in a formulation that is selected from the group consisting of an intramuscular, a depot, a parenteral, an oral, and a topical formulation. Preferably, the compounds inhibit tyrosine kinase activity in vitro, and the patient is a mammal, or preferably a human. Alternatively, the mammal can be a rat, in which case the stated diseases or disorders can be induced.

The term "preventing" as used herein refers to administering a composition to a patient before an abnormal condition manifests itself in that patient, and at least partially stopping or reducing the abnormal condition that would otherwise result.

The term "treating" as used herein refers to the method of the invention having a therapeutic effect and at least partially alleviating or abrogating an abnormal condition in the organism.

The term "therapeutic effect" as used herein refers to the inhibition of cell growth causing or contributing to an abnormal condition. The term "therapeutic effect" also refers to the inhibition of factors causing or contributing to the abnormal condition. A therapeutic effect also refers to relieving to some extent one or more of the symptoms of the abnormal condition.

The term "rheumatoid arthritis" as used herein refers to a chronic systemic disease primarily of the joints, usually polyarticular, marked by inflammatory changes in the synovial membranes and articular structures and by muscle atrophy and rarefaction of the bones. Forms of rheumatoid arthritis include, but are not limited to, juvenile, chronic villous, cricoarytenoid, deformans, degenerative, mutilans, and proliferative.

The term "endometriosis" as used herein refers to a condition in which tissue containing typical endometrial granular and stromal elements occurs aberrantly in various locations in the pelvic cavity or some other area of the body (most commonly the peritoneal cavity).

The term "ocular disease" as used herein refers to diseases of, pertaining to, or affecting the eye, specifically those where new capillaries in the retina invade the vitreous, bleed, and can cause blindness. Examples include, but are not limited to, senile macular degeneration and diabetic retinopathy.

The term "cancer and metastases" as used herein refers to a new growth of tissue in which the multiplication of cells is uncontrolled and progressive and a growth of abnormal cells distant from the site primarily involved by the morbid process.

The term "psoriasis" as used herein refers to a common chronic, squamous dermatosis with polygenic inheritance and a fluctuating course. Methods of diagnosis are well-known to those in the art. It is a chronic skin disorder characterized by hyperproliferation of the epidermis, inflammation and angiogenesis.

The term "arterial thickening" as used herein refers to thickening of the arterial wall as part of the atherosclerotic process or the result of treatments for coronary occlusions, for example. Atherosclerosis refers to an extremely common form of arteriosclerosis in which deposits of yellowish plaques are formed in arteries.

The term "restenosis" as used herein refers to recurrent stenosis, especially of a valve of the heart, after surgical correction of the primary condition. Stenosis refers to narrowing or stricture of a duct or canal.

The term "tissue ischemia" as used herein refers to a deficiency of blood in tissue, usually due to a functional constriction or actual obstruction of a blood vessel.

The term "excessive scarring during wound healing" as used herein refers to the result of uncontrolled angiogenesis leading to neovascularization during wound healing. An example is keloid formation. A keloid is a sharply elevated, irregularly-shaped, progressively enlarging scar.

The summary of the invention described above is not limiting and other features and advantages of the invention will be apparent from the following detailed description of the invention, and from the claims.

BRIEF DESCRIPTION OF THE DRAWINGS

FIG. 1 shows the effect of Compound II on paw volume of adjuvant arthritis rats.

FIG. 2 shows the effect of Compound III on paw volume of adjuvant arthritis rats.

FIG. 3 shows the effect of Compound IV on paw volume of adjuvant arthritis rats.

FIG. 4 shows the effect of test compounds on body weight of adjuvant arthritis rats.

DETAILED DESCRIPTION OF THE INVENTION

The present invention is directed to methods for modulating, suppressing, or inhibiting VEGF, FGF, and/or PDGF stimulation of tyrosine kinase signal transduction. The methods of the invention modulate cellular responses by preventing the phosphorylation of substrate molecules by tyrosine kinases. Interruption of phosphorylation subsequently blocks signal transduction, and thus cell proliferation. The invention further provides methods of treatment of patients having disorders or diseases caused by abnormal cell proliferation such as rheumatoid arthritis, endometriosis, ocular diseases, cancer and metastases, psoriasis, arterial thickening and restenosis, tissue ischemia, and excessive scarring during wound healing.

Indolinone compounds of the invention (e.g. Compound II, Compound III, and Compound IV) inhibit VEGF stimulation of endothelial cells and PDGF stimulation of smooth muscle cells. In addition, these indolinone compounds have activity in vivo in animal models for rheumatoid arthritis.

I. VEGF, FGF, and PDGF Receptor Tyrosine Kinase Families

VEGF Receptor Family

Vascular endothelial growth factor (VEGF) stimulates growth of endothelial cells during the process of angiogenesis (Ferrara, *Trends Cardiovasc. Med.* 1993, 3, 244–250), and also acts as a vascular permeability factor (VPF; Connolly, et al., *J. Biol. Chem.* 1989, 264, 20017–20024) that contributes to the hyperpermeability of tumor vasculature.

VEGF can be found as four different splice variants known as $VEGF_{121}$, $VEGF_{165}$, $VEGF_{189}$ and $VEGF_{206}$ (the number refers to the number of amino acids in the polypeptide). All four isoforms exist as disulfide-linked homodimers, with some structural similarities to the PDGFs. The secretion patterns of the isoforms are different in various cell types, although $VEGF_{165}$ is the most common isoform observed. A fifth variant, $VEGF_{145}$, was recently found in three human carcinoma cell lines that originated from the female reproductive tract (Poltorak, et al., *J. Biol. Chem* 1997 272, 7157–7158). The five isoforms bind with high affinity to two receptors, Flt-1 and Flk-1/KDR, but they differ in their binding affinity for heparin and extracellular matrix.

Recently, two new members of the VEGF family have been identified, VEGF-B and VEGF-C. Two splice variants of VEGF-B have been found (Olofsson, et al., *J. Biol. Chem.* 1996, 271, 19310–19317; Olofsson, et al, *Proc. Natl. Acad. Sci. USA* 1996, 93, 2576–2581) that stimulate the growth of endothelial cells.

VEGF-C, also known as vascular endothelial growth factor-related protein, is a ligand for Flt-4, which is primarily expressed on lymphatic endothelial cells (Joukov, et al. *EMBO J.* 1996, 15, 290–298; Lee, et al., W.I. *Proc. Natl. Acad. Sci. USA* 1996 93, 1988–1992). The distribution of VEGF-C in mouse embryos suggests that it is involved in angiogenesis of lymphatic vasculature (Kukk, et al., *Development* 1996, 122, 3829–3837). VEGF-C also binds to Flk-1/KDR, and its in vitro mitogenic (Lee, 1996, supra) and migratory (Joukov, 1996, supra) effects on vascular endothelial cells may be mediated through this receptor. There is some evidence that co-expression of two VEGF family members in the same cell type leads to the formation of heterodimers.

The VEGF receptor family of tyrosine kinases is characterized by seven immunoglobin-like sequences in the extracellular domain and a split tyrosine kinase domain. VEGFR's include: Flt-1 (fms-like tyrosine kinase), which is also known as VEGFR1 (Shibuya, et al., *Oncogene* 1990, 5, 519–524; De Vries, et al., *Science* 1992, 255, 989–991);

Flk-1 (fetal liver kinase), the mouse RTK (Quinn, et al., *Proc. Natl. Acad. Sci. USA* 1993, 90, 7533–7537; Millauer, et al., *Cell* 1993, 72, 835–846) and its human homolog, KDR (kinase insert domain-containing receptor; Terman, et al., *Biochem. Biophys. Res. Comm.* 1992, 187, 1579–1586); and Flt-4, which is expressed on lymphatic endothelium, but not vascular endothelium (Pajusola, et al., *Cancer Res.* 1992, 52, 5738–43).

Expression of the RTKs, Flk-1 and Flt-1, and their ligand, VEGF, in angiogenic tissues correlates with angiogenesis. During development, transcripts for flk-1 and flt-1 have been detected initially in the endothelial cell precursors and later in the endothelial cells of vessels throughout the embryos of mice, humans, and rats (Millauer, 1993, supra; Yamaguchi, et al., *Development* 1993, 118, 489–98; Breier, et al., *Dev. Dyn.* 1995, 204, 228–3; Kaipainen, et al., *J. Exp. Med.* 1993, 178, 2077–2088). VEGF receptors and VEGF mRNA have also been identified in mouse and rat embryos (Jakeman, et al., *Endocrinology* 1993, 133, 848–859; Breier, et al., *Development* 1992, 114, 521–532). The temporal and spatial patterns of expression of VEGF and its receptors indicate that they are involved in angiogenesis during development.

A number of techniques have been utilized to investigate the roles of Flk-1, Flt-1 and VEGF in angiogenesis. Measurement of mitogenesis in VEGF-stimulated endothelial cells is commonly used as an in vitro model. In such a system, addition of a neutralizing antibody against Flk-1 inhibited mitogenesis (Rockwell, et al., *Mol. Cell. Diff.* 1995, 3, 91–109), as did addition of a truncated soluble form of Flt-1 (Kendall, et al., *Proc. Natl. Acad. Sci. USA* 1993, 90, 10705–10709). Similarly, ribozymes that cleave flk-1 or flt-1 mRNAs reduced the growth of human microvascular endothelial cells, presumably by decreasing the amount of receptors on the cells (Cushman, et al., Abstract from Angiogenesis Inhibitors and Other Novel Therapeutic Strategies for Ocular Diseases of Neovascularization, 1996). However, mutant VEGFs that had reduced binding to Flt-1, but normal binding to Flk-1, stimulated endothelial cells similar to wild-type VEGF (Keyt, et al., *J. Biol. Chem.* 1996, 271, 5638–5646). These studies suggested that Flk-1, and not Flt-1, may be involved in the growth of endothelial cells.

In vivo models have also indicated that VEGF and its receptors are involved in angiogenesis. The genes for all three proteins have been disrupted through targeted mutagenesis in mice. Embryos that were homozygous for mutant forms of flk-1, flt-1 or VEGF were resorbed by days 10 to 12 of development. In the case of the flk-1 disruption, only markers of immature endothelial cells were found and no vessels formed in the embryo or yoke sac (Shalaby, et al., *Nature* 1995, 376, 62–66). This indicated that Flk-1 was required for development of mature endothelial cells. In contrast, embryos lacking Flt-1 had mature endothelial cells, but the vessels were large and disorganized (Fong, et al., *Nature* 1995, 376, 66–70). This suggested that Flt-1 was probably involved in the adhesion process between endothelial cells or between endothelial cells and matrix that is required for normal vessel assembly.

In two studies following disruption of the VEGF gene, heterozygous as well as homozygous embryos were resorbed (Carmeliet, et al., *Nature* 1996, 380, 435–439; Ferrara, et al., *Nature* 1996, 380, 439–442), strongly suggesting that the amount of VEGF expressed during embryonic development is critical. Also, mature endothelial cells were detected, but the vessels in the embryos and yolks were abnormal, as in the case of the flt-1-deficient embryos. It has been suggested that the newly identified ligand for Flt-4, VEGF-C (Joukov, 1996, supra) or VRP (Lee, 1996, supra), may substitute for VEGF, allowing maturation of endothelial cells in the embryos with the disrupted VEGF genes.

FGF Receptor Family

FGF was isolated as a soluble factor that promoted fibroblast proliferation in vitro and has since been found to belong to a large family of proteins (Burgess & Maciag, *Ann. Rev. Biochem.* 1989, 58, 575–606; Jaye, et al., *Biochim. Biophys. Acta.* 1992, 1135, 185–99). At the present time, there appear to be 16 members of the FGF family, including: FGF1/aFGF (Thomas, et al., *J. Biol. Chem.* 1980, 255, 5517–5520; Jaye, et al., *Science* 1986, 233, 541–5); FGF2/bFGF (Gospodarowicz, *J. Biol. Chem.* 1975, 250, 2515–2520; Abraham, et al., *EMBO J.* 1986, 5, 2523–2528; Kurokawa, et al., *FEBS Lett.* 1987, 213, 189–194); FGF3/int2 (Smith, et al., *EMBO J.* 1988, 7, 1013–1022; Brookes, et al., *Oncogene* 1989, 4, 429–436), FGF4/hst/kFGF (Delli-Bovi, et al., *Cell* 1987, 50, 729–737; Taira, et al., *Proc. Natl. Acad. Sci. USA* 1987, 84, 2980–2984; Yoshida, et al., *Proc. Natl. Acad. Sci. USA* 1987, 84, 7305–7309), and FGF5 (Zhan, et al., *Mol. Cell. Biol.* 1988, 8, 3487–3495; Haub, et al., *Proc. Natl. Acad. Sci. USA* 1990, 87, 8022–8026; Bates, et al., *Mot. Cell. Biol.* 1991, 11, 1840–1845) were identified as oncogene products; FGF6 (Marics, et al., *Oncogene* 1989, 4, 335–340); FGF7/KGF, which stimulates keratinocyte proliferation (Finch, et al., *Science* 1989, 245, 752–755); human FGF8 (Payson, et al., *Oncogene* 1996, 13, 47–53) and the mouse homolog, which was originally identified and cloned as an androgen-induced autocrine growth factor for a mouse mammary carcinoma cell (Tanaka, et al., *Proc. Natl. Acad. Sci. USA* 1992, 89, 8928–8932); FGF9/GAF was identified in the supernatant of a human glioma cell line as a novel factor that stimulated the growth of glial cells (Miyamoto, et al., *Mol. Cell. Biol.* 1993, 13, 4251–4259); FGF10, which corresponds to myocyte activating factor (GenBank accession no. U76381); FGF11 and FGF12 (Coulier, et al., *J. Mol. Evol.* 1997, 44, 43–56); and four FGF-homologous factors, designated FHF1-FHF4, which have been implicated in nervous system development (Smallwood, et al., *Proc. Natl. Acad. Sci. USA* 1996, 93, 9850–9857). The receptor binding characteristics of the first nine members of the family have been characterized (Ornitz, et al., *J. Biol. Chem.* 1996, 271, 15292–15297). FGF1 binds to all known splice isoforms for each of the signaling FGF receptors, while the other family members bind to more limited subsets of receptors and their splice variants (Ornitz, 1996, supra).

Currently, there are four related genes encoding human FGF receptors containing cytoplasmic tyrosine kinase domains (Isacchi, et al., *Nucleic Acids Res.* 1990, 18, 1906; Dionne, et al., *EMBO J.* 1990, 9, 2685–92; Keegan, et al., *Proc. Natl. Acad. Sci. USA* 1991, 88, 1095–1099; Partanen, et al., *Proc. Natl. Acad. Sci. USA* 1990, 87, 8913–8917; Partanen, et al., *EMBO J.* 1991, 10, 1347–1354): FGF-R1/flg (fins-like gene), which is a receptor for FGF1 (Ruta, et al., *Proc. Natl. Acad. Sci. USA* 1989, 86, 8722–8726); FGF-R2/bek (bacterially expressed kinase; Kombluth, et al., *Mol. Cell. Biol.* 1988, 8, 5541–5544) and human FGF-R2 (Dionne, 1990, supra); FGF-R3/cek2 (chicken embryo kinase 2; Pasquale & Singer, *Proc. Natl. Acad. Sci. USA* 1989, 86, 5449–5453) and human FGF-R3 (Partanen, 1991, supra; Keegan, 1991, supra); and FGF-R4 (Partanen, 1990, supra; Partanen, 1991, supra; Holtrich, et al., *Proc. Natl. Acad. Sci. USA* 1991, 88, 10411–10415). The four human FGF receptors have a variety of alternative splice variants, including some that are not membrane localized or that do not contain kinase domains (for reviews, see Givol & Yayon, *FASEB J.* 1992, 6, 3362–3369; Johnson & Williams, *Adv.*

Cancer Res. 1993, 60, 1–41; Green, et al., *BioEssays* 1996, 18, 639–646; Jaye, 1992, supra). Splice variant receptor forms have been shown to bind a restricted set of FGFs and transduce mitogenic signaling with different efficacies (Ornitz, 1996, supra).

In vitro studies have linked FGF with angiogenesis. Blocking of FGF-2 (bFGF) interactions with its receptor by antibodies to FGF-2 (Mignatti, et al., *J. Cell Biol.* 1989, 108, 671–682; Sato, et al., *Biochem. Biophys. Res. Com.* 1991, 180, 1098–1102), addition of platelet factor 4 (Sato, 1991, supra), or mutations in FGF-2 in the heparin binding site (Li, et al., *Biochem.* 1994, 33, 10999–11007), resulted in inhibition of various steps involved in in vitro angiogenesis. These included induction of endothelial cell protease expression (Mignatti, 1989, supra; Li, 1994, supra), cellular invasion (Mignatti, 1989, supra), and formation of capillary-like tubes (Sato, 1991, supra; Li, 1994, supra).

There are also correlative observations relating the expression of FGF-2 and FGF-R1 to cardiac development (Parlow, et al., *Dev. Biol.* 1991, 146, 139–147; Sugi, et al., *Dev. Dyn.* 1995, 202, 115–125) and endothelium re-establishment after vessel injury (Lindner & Reidy, *Circ. Res.* 1993, 73, 589–595). Dominant-negative FGF receptors have been targeted to the eye lens (Robinson, et al., *Development* 1995, 121, 3959–3967; Chow, et al., *Development* 1995, 121, 4383–4393), epidermis (Werner, et al., *EMBO J.* 1993, 12, 2635–2643), and lung (Peters, et al., *EMBO J.* 1994, 13, 3296–3301), but not endothelium.

In vivo studies have also linked FGF and angiogenesis. A secreted form of FGF-1 (aFGF) was found to induce neointimal hyperplasia and angiogenesis (Nabel, et al., *Nature* 1993, 362, 844–846), and significant enhancement of endothelialization was induced by FGF-1 coating of ePTFE vascular grafts (Gray, et al., *J. Surg. Res.* 1994, 57, 596–612). Mouse embryos homozygous for deletion of the FGF-R1 gene died early in development (prior to E10.5) and exhibited gross abnormalities in mesodermal patterning (Yamaguchi, et al., *Genes Dev.* 1994, 8, 3032–3044; Deng, et al., *Genes Dev.* 1994, 8, 3045–3057).

PDGF Receptors

Many studies have shown unequivocally that PDGF is made by a number of cell types under normal or pathological conditions including atherosclerosis, fibrotic disease, and cancer. PDGF consists of two related polypeptide chains (A and B) which are assembled as biologically active hetero- and homo-dimers. The three isoforms of PDGF (AA, AB, and BB) have molecular weights of approximately 28 kDa and bind with different affinities to the two different receptor types, and (for review see Ross, et al., *Cell* 1986, 46, 155–169). PDGF A chain binds to the -receptor, whereas the B chain binds both -and -receptors. (for review of PDGF receptors see Claessen-Welsh, in *Biology of Platelet-Derived Growth Factor* (Westermark & Sorg, eds.), Cytokines. Basel, Karfger, 1993, 5, 31–43).

Spatial and temporal expression of PDGF-BB and the PDGF -receptors suggests that they may play a role in angiogenesis. Both are expressed in vessels in human placenta (Holmgren, et al., *Dev.* 1991, 113, 749–754), healing wounds, adenocarcinoma (Sundberg, et al., *Amer. J. Pathol.* 1993, 143, 1377–1388) and glioblastoma (Plate, et al., *Lab Invest.* 1992, 67, 529–534). PDGF has been suggested to play an indirect role by inducing VEGF (Brogi, et al., *Circulation* 1994, 90, 649–652; Tsai, et al., *J. Neurosurg.* 1995, 82, 864–873). In addition, it may also exert growth stimulatory effects on pericytes (Sundberg, 1993, supra) and fibroblast-like cells (Sato, 1991, supra; Nicosia, et al., *Amer. J. Pathol.* 1994, 145, 1023–1029) which surround the endothelial cells. Mouse embryos deficient in PDGF-B have been shown to lack microvascular pericytes which normally form part of the capillary wall and contribute to its stability (Lindahl, et al., *Science* 1997, 227, 242–245). The PDGF-B deficient mice developed numerous capillary microaneurysms that ruptured at late gestation.

II. Target Diseases to be Treated by Methods of the Invention

Protein kinases are essential regulatory molecules that control a variety of cellular functions. For this reason, any alteration in the function of a protein kinase can cause an abnormal condition in an organism. One of the many functions controlled by protein kinases is cell proliferation.

Alterations in the function of a protein kinase that normally regulates cell proliferation can lead to enhanced or decreased cell proliferative conditions evident in certain diseases. Aberrant cell proliferative conditions include angiogenic and vasculogenic disorders including rheumatoid arthritis, endometriosis, ocular diseases, cancer and metastases, psoriasis, arterial thickening and restenosis, tissue ischemia, and excessive scarring during wound healing.

Cancer and Metastasis

The link between angiogenesis and cancer is well established. Neovascularization is an important step in the transition from hyperplasia to neoplasia and it must occur for tumors to grow beyond 1 to 2 mm$^3$ (Folkman, *J. Natl. Cancer Inst.* 1990, 82, 4–6; Folkman, et al., *Nature* 1989, 339, 58–61). A correlation between microvessel density and severity of disease has been observed in a number of different tumor types including malignant glioma (Plate & Risau, *GLIA* 1995, 15, 339–347), and breast (Horak, et al., *Lancet* 1992, 340, 1120–124), bladder (Dickinson, et al., *Br. J. Urol.* 1994, 74, 762–766), colon (Takahashi, et al., *Cancer Res.* 1995, 55, 3964–3968), and endometrial cancer (Kirschner, et al., *Am. J. Obstet. Gynecol.* 1996, 174, 1879–1882).

Many activators of tumor angiogenesis are growth factors which stimulate proliferation of endothelial cells. The roles of VEGF and its cognate receptor Flk-1/KDR are well established. VEGF is secreted by a number of human tumor cell lines in culture, including glioma (Tsai, et al., *J. Neurosurg* 1995, 82, 864–867), melanoma (Claffey, et al., *Cancer Res.* 1996, 56, 172–181.) Kaposi sarcoma, and epidermoid carcinoma cells (Myoken, et al., *Proc. Natl. Acad. Sci. USA* 1991, 88, 5819–5823). More importantly, VEGF transcripts or protein has been identified by in situ hybridization or immunohistochemistry in primary gliomas (Plate, et al., *Lab Invest.* 1992, 67, 529–534; Plate, et al., *Int. J. Cancer* 1994, 59, 520–529), hemangioblastomas (Hatva, et al., *Amer. J. Pathol.* 1996, 148, 763–775) and breast (Toi, et al., *Jpn. J. Cancer Res.* 1994, 85, 1045–1049; Anan, et al., *Surgery* 1996, 119, 333–339; Yoshiji, et al., *Cancer Res.* 1996, 56, 2013–2016), colon (Brown, et al., *Cancer Res.* 1993, 53, 4727–4735; Takahashi, et al., *Cancer Res.* 1995, 55, 3964–3968) and renal cell tumors (Takahashi, et al., *Cancer Res.* 1994, 54, 4233–4237). In glioblastoma, the message for VEGF is found in cells adjacent to necrotic regions which is consistent with upregulation by hypoxia (Shweiki, et al., *Nature* 1992, 359, 843–845; Plate, et al, *Lab Invest.* 1992, 67, 529–534). Furthermore, patients with cancer have significantly higher serum VEGF levels than normal volunteers. The highest VEGF concentrations were observed in patients with untreated metastatic cancers.

A number of animal models have been developed to investigate the function of VEGF in tumor angiogenesis. Rat C6 glioma and human U87MG glioblastoma cells secrete VEGF and grow subcutaneously in athymic mice (Saleh, et al., *Cancer Res.* 1996, 56, 393–401; Cheng, et al., *Proc. Natl. Acad. Sci. USA* 1996, 93, 8502–8507). The introduction of antisense constructs to VEGF mRNA into these cell lines reduces their in vivo growth, as well as the degree of neovascularization. Monoclonal antibodies against VEGF inhibit the subcutaneous growth of human rhabdomyosarcoma, glioblastoma, leiomyosarcoma (Kim, et al., *Nature* 1993, 362, 841–844) and fibrosarcoma (Asano, et al., *Cancer Res.* 1995, 55, 5296–5301) in athymic mice. Metastasis of fibrosarcoma (Asano, et al., *Cancer Res.* 1995, 55, 5296–5301) and colon cancer tumors (Warren, et al., *J. Clin. Invest.* 1995, 95, 1789–1797) was also blocked by anti-VEGF antibodies. The presence of VEGF in primary tumors and tumor cell lines, as well as the inhibitory activity of antisense and neutralizing antibodies to VEGF, indicate that VEGF is a significant player in tumor angiogenesis.

The contribution of the VEGF receptors, Flk-1/KDR and Flt-1, to tumor growth has also been studied extensively. Like VEGF, their mRNA has been detected in tumors such as gliomas (Plate, et al., *Lab Invest.* 1992, 67, 529–534), Plate, et al., *Int. J. Cancer* 1994, 59, 520–529), hemangioblastomas (Hatva, et al., *Am. J. Pathol.* 1996, 146, 368–378), colon cancer (Takahashi, et al., *Cancer Res.* 1995, 55, 3964–3968) and adenocarcinomas (Brown, et al., *Cancer Res.* 1993, 53, 4727–4735). In these cases, the receptors were detected on the endothelial cells of the vessels and not the tumor cells. This supports a paracrine mechanism in which VEGF secreted from tumor cells stimulates proliferation of endothelial cells. In contrast, Kaposi Sarcoma (KS) cell lines and primary tissue express Flt-1 and KDR as well as VEGF (Masood, et al., *Proc. Natl. Acad. Sci. USA* 1997, 94, 979–984). This finding, coupled with the observation that growth of KS cell lines is inhibited by VEGF antisense oligonucleotides, suggests that an autocrine loop may be present in Kaposi Sarcoma leading to enhanced cell growth and vasculature.

The capacity of Flk-1 to act as a modulator of tumor growth has also been studied in animal tumor models. Athymic mice were co-implanted with tumor cells and virus-producing cells that produced viral DNA encoding a truncated flk-1 gene (Millauer, et al., *Nature* 1994, 367, 576–579; Millauer, *Cancer Res.* 1996, 56, 1615–1620). The co-implantation allowed the introduction of mutant receptor into endothelial cells where it acted in a dominant-negative fashion to block activation of Flk-1 and effect the growth of the tumor. By this method, the subcutaneous growth of a variety of human, rat and mouse tumor cells was shown to be inhibited. In addition, the microvessel density was shown to be reduced in the small tumors that did form, confirming the connection between Flk-1, angiogenesis, and tumor growth.

Flk-1/KDR is an excellent target for the development of novel anticancer agents. Specific inhibitors of Flk-1 KDR would be expected to have fewer side effects than cytotoxic chemotherapy drugs, since angiogenesis is thought to rarely occur in healthy adults (with the exception of angiogenesis that occurs following wound injury or during cyclical changes in the endometrium and ovary). Monoclonal antibodies specific for VEGF (Kim, et al., *Nature* 1993, 362, 841–844) and Flk-1 (Rockwell, et al., *Proc. Am. Assc. Cancer Res.* 1997, 38, 266) have been shown to inhibit tumor growth in animals by disrupting binding of VEGF to the receptor. Also, synthetic small molecule inhibitors of Flk-1 tyrosine kinase activity have been shown to block the effects of VEGF in several in vitro and in vivo systems (Strawn, et al., *Cancer Res.* 1996, 56, 3540–3545).

Acidic and basic fibroblast growth factors (FGF1/aFGF and FGF2/bFGF) and their receptors, FGFR-1 and FGFR-2, have been identified in a variety of tumor types. A human renal cell carcinoma cell line has been shown to secrete FGF2/fbFGF (Singh, et al., *Cell Growth Diff.* 1996, 7, 397–404) and two human prostate tumor cell lines were found to make and respond to FGF2/bFGF (Nakamoto, et al., *Cancer Res.* 1992, 52, 571–577). Analysis of mRNA from various grades of astrocytomas revealed that the expression of different FGF receptors changes as the tumors progress to higher grades of malignancy (Yamaguchi, et al., *Proc. Natl. Acad. Sci. USA* 1994, 91, 484–488). Surgically excised skin from melanoma patients was found to have high FGFR-1 expression in the invading melanoma cells and stroma, but not in the endothelial cells (Kaipainen, et al., *Cancer Res.* 1994, 54, 6571–6577). The distribution pattern of FGFs and their receptors implicate FGFs in tumor growth.

Neutralizing antibodies specific for FGF2/bFGF have been used to investigate the role of FGF2/bFGF in cancer. FGF-induced mitogenesis of SC115 mouse mammary carcinoma cells in response to bFGF was shown to be inhibited by anti-FGF antibodies (Lu, et al., *Cancer Res.* 1989, 49, 4963–4967). Similarly, an anti-FGF2/bFGF monoclonal antibody blocked the growth of U-87MG and T98G human glioblastoma cells in culture and as xenografts in nude mice (Takahashi, et al., *FEBS Lett.* 1991, 288, 65–71).

Compounds that inhibit FGF signaling are currently under development as anticancer agents. Tecogalan sodium, an inhibitor of FGF2/bFGF binding to its receptor, is currently in clinical trials for the treatment of solid tumors and Kaposi's sarcoma (Eckhardt, et al., *Ann. Oncol.* 1996, 7, 491–496). The polyanionic compound, suramin, is also under investigation as an FGF inhibitor (Takano, et al., *Cancer Res.* 1994, 54, 2654–2660), although it blocks the binding of a number of growth factors to their receptors. The synthetic compound, thalidomide (D'Amato, et al., *Proc. Natl. Acad. Sci. USA* 1994, 91, 4082–4085), and the protein-based angiogenesis inhibitors, angiostatin and endostatin (O'Reilly, et al., *Cell* 1994, 79, 315–328; O'Reilly, et al., *Cell* 1997, 88, 277–285), block FGF2/bFGF-induced angiogenesis, but it is not known whether they work directly on signaling through the FGF receptor.

Other growth factors and their receptors that play a supporting role in angiogenesis are probably also involved in tumor growth. PDGF receptors have also been identified in various tumors and tumor cell lines and contribute to the transformation of cells. As with the FGF receptors, they may contribute to the growth of tumors by promoting angiogenesis and tumor cell proliferation and survival.

The PDGF and PDGF-receptor family should be considered an important player in angiogenic studies particularly in light of the recent knock-out mice showing a role for PDGF-B chain in pericytes. PDGF is the most potent mitogen for cells of mesenchymal origin. Kidney glomerular mesangial cells were the targets of disrupted PDGF-B or PDGF-β receptor (Leveen, P., et al., *Genes Dev.* 1994, 8, 1875–1887; Soriano, P., *Genes Dev.* 1994, 8, 1888–1896) genes in mice and were found to lead to the development of lethal hemorrhage and edema in late embryogenesis. Mesangial cells are related to microvascular pericytes, another target of the disrupted PDGF-B gene. Pericytes encircle the microvessels in many different tissues. They are contractile cells and therefore may contribute to the mechanical stability of the capillary wall. Pericytes express PDGF receptors and respond to PDGF in vitro. Pericytes may also regulate endothelial cell function. Thus, PDGF and its receptors may function to support vascular integrity.

Rheumatoid Arthritis

Rheumatoid arthritis (RA) is an inflammatory joint disease that is characterized by cellular infiltration of synovial fluid by neutrophils, and of the synovial membrane by T lymphocytes and macrophages, hyperproliferation of cells of the synovial membrane which results in formation of a pannus, and destruction of cartilage and bone (Feldman, et al., *Ann. Rev. Immunol.* 1996, 14, 397–440; Paleolog, *Br. J. Rheumatol.* 1996, 35, 917–920). Angiogenesis is thought to have an important role in the pathogenesis of RA (Colville-Nash & Scott, *Annals. Rheumatic Diseases* 1992, 51, 919–925, and references therein); inhibition of angiogenesis with the fumagillin analog, AGM-1470, suppresses RA in experimental models of RA (Peacock, et al., *J. Exp. Med.* 1992, 175, 1135–1138; Peacock, et al., *Cell. Immunol.* 1995, 160, 178–184).

Many growth factors and cytokines have been implicated as having a role in RA (see Feldman, et al., *Ann. Rev. Immunol.* 1996, 14, 397–440 for a review), some of which have also been implicated as angiogenic factors (see Colville-Nash & Scott, *Ann. Rheumatic Dis.* 1992, 51, 919–925; Shawver, et al., *Drug Disc. Today* 1997, 2, 50–63 for reviews). Putative angiogenic factors that have been reported to be expressed in RA synovial fluid or tissue include VEGF (Fava, et al., *J. Exp. Med.* 1994, 180, 341–346; Koch, et al. *J. Immunol.* 1994, 152, 4149–4156; Nagashima, et al., *J. Rheumatol.* 1995, 22, 1624–1630; Ben-Av, et al., *FEBS Lett.* 1995, 372, 83–87), FGF2/FGF2/bFGF (Cozzolino, et al., *J. Clin. Invest.* 1993, 91, 2504–2512; Tamura, et al., *Endocrinol* 1996, 137, 3729–3737), and FGF1/aFGF (Byrd, et al., *Arth. & Rheumat.* 1996, 39, 914–922). The strongest evidence for a role as a direct angiogenic factor exists for VEGF.

VEGF expression is significantly higher in synovial fluid and tissue from RA patients than from patients with other types of arthritis (Fava, et al., *J. Exp. Med.* 1994, 180, 341–346; Koch, et al. *J. Immunol.* 1994, 152, 4149–4156). The source of this VEGF appears to be elevated expression in synovial lining cells, subsynovial macrophages, fibroblasts surrounding microvessels, and vascular smooth muscle cells (Fava, et al., *J. Exp. Med.* 1994, 180, 341–346; Koch, et al. *J. Immunol.* 1994, 152, 4149–4156; Nagashima, et al., *J. Rheumatol.* 1995, 22, 1624–1630). Indirect induction of VEGF by other factors may occur as well.

Synovial lining cells, macrophages, endothelial cells, and vascular smooth muscle cells of rheumatoid joints (Hosaka, et al., *Pathobiol.* 1995, 63, 249–56), as well as mast cells in rheumatoid synovium (Qu, et al., *Am. J. Pathol.* 1995, 147, 564–573), have been reported to express FGF2/bFGF, but it does not appear to be elevated in RA synovial fluid (Hosaka, 1995, supra). FGF1/aFGF is abundantly expressed in synovial tissues from RA patients (Byrd, et al., *Arthritis & Rheumatism* 1996, 39, 914–922), and expression of FGF-R1, the receptor for FGF1 and FGF2 (Ornitz, et al., *J. Biol. Chem.* 1996, 271, 15292–15297), is enhanced on CD4$^+$ T cells (Byrd, 1996, supra).

Psoriasis

Psoriasis is a chronic skin disorder that is characterized by hyperproliferation of the epidermis, inflammation, and angiogenesis. Angiogenesis appears to be crucial in the pathogenesis of psoriasis, and microvascular changes are one of the earliest detectable events in developing psoriatic lesions (for a review see Creamer & Barker, *Clin. Exp. Dermatol.* 1995, 20, 6–9). Several reports have implicated the epidermis as the origin of angiogenic factors (Nishioka & Ryan, *J. Invest. Dermatol.* 1972, 58, 33–45; Wolf & Harrison, *J. Invest. Dermatol.* 1973, 59, 40–43; Barnhill et al., *Br. J. Dermatol* 1984, 110, 273–281; Malhotra, et al., *Lab. Invest.* 1989, 61, 162–165). However, it has long been recognized that the inflammatory component of the disease complicates dissection of the angiogenic factors involved in the disease (Wolf, *Lab. Invest.* 1989, 61, 139–142), since cytokines secreted by lymphocytes, macrophages, mast cells and neutrophils can also contribute to angiogenesis (Majewski, et al., *Arch. Dermatol.* 1985, 121, 1018–1021; Majewski, et al., *Arch. Dermatol.* 1987, 123, 221–225; Koch, et al., *Science* 1992, 258, 1798–1801; Qu, et al., *Am. J. Pathol.* 1995, 147, 564–573).

Of the many angiogenic factors identified in skin (Arbiser, Am. Acad. Derm. 1996, 34, 486–497), VEGF has been the best characterized as a direct inducer of angiogenesis. VEGF is overexpressed in keratinocytes of psoriatic skin, but only minimally expressed in normal epidermis (Detmar, et al., *J. Exp. Med.* 1994, 180, 1141–1146). VEGF is also overexpressed in other skin diseases such as bullous pemphigoid, dermatitis herpetiformis, and erythema multiforme (Brown, et al., *Invest. Dermatol.* 1995, 104, 744–749), in delayed skin hypersensitivity reactions (Brown, et al., *J. Immunol.* 1995, 154, 2801–2807), and probably after sun exposure, as suggested by the induction of VEGF expression in cultured keratinocytes following exposure to ultraviolet light (Brauchle, et al., *J. Biol. Chem.* 1996, 271, 21793–21797).

FGF2/bFGF is expressed in keratinocytes and endothelial cells and stimulates the proliferation of both through autocrine and paracrine mechanisms (Schweigerer, et al., *Nature* 1987, 325, 257–259; O'Keefe, et al., *J. Invest. Dermatol.* 1988, 90, 767–769). Mast cells have also been reported to be a major source of FGF2/bFGF in chronic inflammatory diseases (Qu, et al., *Am. J. Pathol.* 1995, 147, 564–573), which may contribute to the link between inflammation and angiogenesis.

Ocular Diseases

The release of angiogenic factors from the ischemic retina has been hypothesized to be the central stimulus for retinal neovascularization. Glaucoma, vitreous hemorrhage and retinal detachment, secondary to intraocular neovascularization, accounts for the resultant vision loss in several ocular disorders such as retinopathy of prematurity, age-related macular degeneration, and diabetic retinopathy. The release of angiogenic factors by the ischemic retina to induce new blood vessel growth and increase the oxygen supply to the area turns out to be harmful as the new vessels do not grow with normal architecture. Edema, hemorrhage, vessel tortuosity, and pathological neovascularization subsequently result in retinal detachment and lead to blindness.

Some angiogenic factors such as IGF-1, FGF and VEGF have elevated expression in vitreous and neovascular membranes from patients with retinal disorders (Grant, et al., *Diabetes* 1986, 35, 416–20; Sivalingam, et al., *Arch Ophthalmol.* 1990, 108, 869–72; Aiello, et al., *New Engl. J. Med.* 1994, 331, 1480–1487; Malecaze, et al., *Arch. Ophthalmol.* 1994, 112, 1476–82; Adamis, et al., *Amer. J. Ophthalmology* 1994, 118, 445–50). Therefore, these growth factors are candidates for the angiogenic factors which modulate or initiate intraocular neovascularization in retinal disorders.

VEGF is constitutively expressed in the vascularized tissues of the normal eye (Adamis, et al., *Arch. Ophthalmol.* 1996, 114, 66–71). Intraocular VEGF gene expression is increased in disease states like diabetic retinopathy (Adamis, et al., *Amer. J. Ophthalmology* 1994, 118, 445–450; Malecaze, et al., *Arch. Ophthalmology* 1994, 112, 1476–1482; Aiello, 1994, supra; Pe'er, et al., *Lab Invest.* 1995, 72, 638–645). Using a neutralizing antibody specific for VEGF and soluble VEGF-receptor chimeric proteins, it has been shown that VEGF is sufficient to induce neovascularization (Aiello, 1994, supra; Adamis, 1994, supra; Tolentino, et al., *Ophthalmology* 1996, 103, 1820–1828; Tolentino, et al., *Arch. Ophthalmol.* 1996, 114, 964–970). In animal models, intraocular injections of VEGF into normal eyes caused retinal edema, microaneurysms, hemorrhage and intraretinal neovascularization (Pierce, et al., *Arch. Ophthalmol.* 1995, 114, 964–970; Miller, et al., *Am. J. Pathol.* 1994, 145, 574–584; Tolentino, 1996, supra). Decreased levels of VEGF paralleled the regression of proliferative retinopathy. Stimuli associated with oxygen deprivation such as hypoxia (Pierce, 1995, supra; Miller, 1994, supra; Shweiki, et al., *Nature* 1992, 359, 843–845; Plate, et al., *Lab Invest.* 1992, 67, 529–34), generation of oxygen intermediates (Kuroki, et al., *Angiogenesis Novel Therapeutic Development Conference* 1996, unpublished communication), and accumulation of advanced glycation endproducts (Adamis, Angiogenesis Novel Therapeutic Development Conference, 1997) in diabetics, increased endogenous VEGF expression in vivo. Inhibitors of VEGF signaling including antisense VEGF reagents (Smith, *IBC Conference on Angiogenesis Inhibitors and Other Novel Therapeutic Strategies for Ocular Diseases of Neovascularization* 1996) and soluble VEGF receptor chimeric proteins (Aiello, et al., *Proc. Natl. Acad. Sci. USA* 1995, 92, 10457–10461), ribozymes targeting VEGF receptor subtype mRNAs (Cushman, et al., *Abstract from Angiogenesis Inhibitors and Other Novel Therapeutic Strategies for Ocular Diseases of Neovascularization* 1996; Pavco, *IBC Conference on Novel Anti-angiogenic Therapy for Diabetic Retinopathy, Macular Degeneration and Other Ocular Diseases of Neovascularization* 1997) and selective PKC inhibitors (Aiello, 1995, supra) resulted in significant inhibition of corneal and retinal neovascularization, VEGF-stimulated cell growth in vitro and VEGF-induced retinal permeability in vivo. All of these data provide strong support for a direct role of VEGF in ocular angiogenesis.

FGF2/bFGF appears to play a role in diabetic retinopathy (Sivalingam, et al., *Arch Ophthalmol* 1990, 108, 869–872; Hanneken, et al., *Arch. Ophthalmol* 1991, 109, 1005–1011). In addition to being present in vitrectomy samples from retinal disorders (Sivalingam, 1990, supra), FGF2/bFGF induces endothelial cell proliferation (Gospodarowitz, *Prog. Clin. Biol. Res.* 1976, 9, 1–19; D'Armore & Klagsbrun, *J. Cell Biol.* 1976, 99, 1545–9), migration (Herman & D'Armore, *J. Muscle Res. Cell Motil* 1984, 5, 697–709) and the release of collagenase and plasminogen activators (Presta, et al., *Mol. Cell. Biol.* 1986, 6, 4060–6). In vivo, FGF2/bFGF induces corneal neovascularization (Gospodarowitz, et al., *Exp. Eye Res.* 1979, 28, 501–14; Risau, *Proc. Natl. Acad Sci. USA* 1986, 83, 3855–3859) as well as retinal fibrovascular proliferation with an enhanced fibrotic component compared to IGF-1 when injected into the vitreous cavity (Grant, et al., *Reg. Peptides* 1993, 48, 267–278). The development of retinal capillary basement membrane thickening and subsequent retinal traction and detachment is similar to those occurring in humans and animals with diabetes.

Arterial Thickening and Restenosis

Arterial injury as part of the atherosclerotic process or as a consequence of balloon-mediated injury to treat coronary occlusions is known to be accompanied by thickening of the arterial wall. This response is also observed in cases of organ rejection where chronic vascular injury is associated with thickening of the arteries at the site of the organ transplant. RTKs have been implicated as important players within the disease process associated with the injury response. As in the case of atherosclerosis (herein), both PDGF and FGFs are associated with the hyperproliferation of the arterial smooth muscle cell. When these cell layers become ischemic, they require new blood vessel formation in order to support their hyperproliferation. In the case of smooth muscle cell migration, the activation of mitogen-activated protein kinase has been shown to be associated with PDGF-dependent cell movement (Graf, et al., *Hypertension* 1997, 29, 334–339).

A synthetic compound that blocks binding of PDGF to its receptor has been shown to inhibit chemotaxis of smooth muscle cells and inhibit neo-intimal formation in restenotic lesions following balloon-injury of carotid arteries in rats (Mullins, et al., *Arterioscler Thromb* 1994, 14, 1047–1055). In addition, PDGF mRNA levels have been shown to be increased in human cardiac allografts (Zhao, et al., *J. Clin. Invest.* 1994, 94, 992–1003). In animal models, PDGF and FGF have been shown to be expressed in the injury response following cardiac (Zhao, 1994, supra; Zhao, et al., *Circulation* 1994, 90, 677–685) and renal (Alpers, et al., *Am. J. Pathol.* 1996, 148, 439–451; Abboud, *Annu. Rev. Physiol.* 1995, 57, 297–309) transplantation.

Atherosclerosis

Atherosclerosis is a disease associated with the formation of arterial lesions or atheromas consisting of endothelium-covered fibro-fatty plaques. Beneath the endothelial layer exists smooth muscle cells and extracellular matrix components containing variable amounts of serum proteins. This overlies an area characterized by collections of lipid-laden macrophages. Significant numbers of lymphocytes, particularly T cells, are also present and may contribute to lymphocyte-mediated angiogenesis (Kaminski, M. & Auerbach, R., *Proc. Soc. Exp. Biol. Med.* 1988, 188, 440–443). Both macrophages and lymphocytes traverse the endothelium in order to enter the atheroma lesion. The lesion is characterized by a flux of blood cells including platelets that enter or exit the endothelium. Similar to the restenotic lesion, the build up of smooth muscle cells is supported by angiogenesis and is likely to be stimulated by factors released from the smooth muscle cells when they become hypoxic. In contrast to atheromas, thrombi of arteries and veins are characterized by structures containing a fibrin mesh in which blood cells are entrapped.

The presence of platelets and other cells in the lesion have led to a number of studies that implicate growth factors and their cognate receptor tyrosine kinases as players in the disease (Chabrier, *Int. Angiol.* 1996, 15, 100–103). The most prominent player in this regard is PDGF. PDGF has been detected in atherosclerotic lesions of rat (Waltenbeger, et al., *Arterioscler Thromb. Vasc. Biol* 1996, 16, 1516–1523), rabbit (Agapitos, et al., *Int. Angiol*. 1996, 15, 249–251), and human (Billett, et al., *Arterioscler Thromb. Vasc. Biol.* 1996, 16, 399–406; Ito, et al., *Neurol. Res.* 1995, 17, 345–348) origin. The release of PDGF from platelets and other lymphocytes is thought to elicit a pleiotrophy of paracrine effects on blood cells and smooth muscle cells in the vicinity of the lesion. The chemoattractant, cell survival, migratory and mitogenic properties of PDGF receptor function in cells may contribute directly or indirectly to different activities on different cell types.

PDGF RNA expression has been shown to be associated with the presence of circulating mononuclear cells in hypercholesterolemic patients (Billett, 1996, supra). The presence of mononuclear and other blood cells in the atherosclerotic lesion has been shown to also elaborate the expression of VEGF and FGF growth factors. In smooth muscle cells, PDGF has been shown to exert a number of effects that may directly or indirectly effect the angiogenic process (Newby, A. C. & George, S. J., *Curr. Opin. Cardiol.* 1996, 11, 574–582). For instance, it has been suggested that PDGF signaling may upregulate the expression of VEGF in smooth muscle cells (Stavri, et al., *FEBS Lett.* 1995, 358, 311–315). In addition, it is clear that PDGF is a player in myointimal proliferation associated with formation of atherosclerotic plaques. The proliferative (Randone, et al., *Eur. J. Vasc. Endovasc. Surg.* 1997, 13, 66–71), migratory (Graf, 1997, supra; Abedi, H. & Zachary, I., *Cardiovasc. Res.* 1995, 30, 544–56; Koster, et al.,*Angiology* 1995, 46, 99–106), and cell survival (Bennet, et al., *J. Clin. Invest.* 1995, 95, 2266–2274) aspects of PDGF function in smooth muscle cells may be a major determinant of the formation of the atherosclerotic lesion.

In addition, increased expression of PDGF (Waltenberger, 1996, supra; Stavri, 1995, supra; Michiels, et al., *Exp. Cell. Res.* 1994, 213, 43–54), VEGF (Stavri, 1995, supra; Knighton, et al., *Science* 1983, 221, 1283–1285; Li, et al., *Am. J. Physiol.* 1996, 270, 1803–1811), and FGF (Michiels, 1994, supra) has been shown to occur in smooth muscle cells under conditions of hypoxia. It has been well established that endothelial cell growth and angiogenesis is triggered by conditions of low oxygen tension. The inducibility of these factors is consistent with previous association of these factors and Flk-1/KDR, Flt-1, PDGF receptors, and FGF receptors as participants in this process. In the case of a fibrotic thrombus, the fibrin gel itself is viewed as a provisional matrix into which vascularized connective tissue invades, similar to wound healing. FGF has been considered to be an important player in hyperproliferative and angiogenic aspects of this lesion. FGF1/aFGF and FGF2/bFGF or receptor expression has been shown to be increased in rat aortic smooth muscle cells (van Neck, et al., *Biochim. Biophys. Acta.* 1995, 1261, 210–214), human cardiac allografis (Zhao, 1994, supra; Zhao, 1994, supra), CD4$^+$ T cells (Zhao, et al., *J. Immunol.* 1995, 155, 3904–3911), and atherosclerotic human arteries (Hughes, *Cardiovasc. Res.* 1996, 32, 557–569).

Since PDGF, VEGF and FGF play a role in the formation of atheromas and fibrotic lesions, RTK-mediated signaling events may be important in the development and maintenance of the lesion. Interruption of these signaling systems inhibit the formation or disrupt the remodeling or integrity of the lesion. In the fibrotic thrombus, targeting of these receptors may be advantageous to reduce the number of connective tissues cells involved in fibrin deposition and development of the clot.

Tissue Ischemia

The formation of new blood vessels is tightly regulated by receptor tyrosine kinases and their cognate ligands. This has been best substantiated for the VEGF, FGF and PDGF receptor systems where these receptors effect the growth and survival of endothelial cells, pericytes, and arterial smooth muscle cells. In the case of tissue ischemia, the induction of new blood vessel growth may be advantageous for the treatment of specific human diseases where oxygen and nutrient limitation is linked to the disease pathology. Since PDGF (Alpers, 1996, supra; Waltenbeger, 1996, supra; Michiels, 1994, supra), VEGF (Stavri, 1995, supra; Knighton, 1983, supra; Li, 1996, supra), and FGF (Michiels, 1994, supra) have been shown to be expressed in cells under hypoxic conditions, growth factor therapy leading to the induction of new blood vessels has been suggested as a mechanism to overcome myocardial ischemia (Ware & Simons, *Nature Med* 1997, 3, 158–164). This rationale suggests that treatment for diseased hearts may relieve symptoms by restoration of myocardial oxygen or restoration of blood flow and thereby prevent disease progression or improve treatments using angioplasty or following coronary bypass surgery.

Animal experiments support the rationale for treatments based on these factors. Acute ischemia models in dogs (Yanigisawa-Miwa, et al., *Science* 1992, 257, 1401–1403) and pigs (Battler, et al., *J. Am. Coll. Cardio.* 1995, 22, 2001–2006; Padua, et al., *Mol. Cell. Biochem.* 1995, 143, 129–135) have suggested that intracoronary injection of FGF may be beneficial. Chronic administration of FGF2/bFGF to dogs with chronic coronary occlusion showed a fast improvement in function and increased number of vessels (Giordano, et al., *Nature Med.* 1996, 2, 534–539; Lazarous, et al., *Circulation* 1995, 91, 145–153). Moreover, chronic intracoronary infusion of VEGF resulted in substantial improvement of coronary flow of the diseased heart (Pearlman, et al., *Nature Med.* 1995, 1, 1085–1089; Harada, et al., *Am. J. Physiol.* 1996, 270, 1792–1802). Peripheral ischemia has been shown to have improved collateral circulation upon injection of FGF2/bFGF (Baffour, et al., *J. Vasc. Surg.* 1992, 16, 181–191) and VEGF (Takeshita, et al., *J. Clin. Invest* 1994, 93, 662–670). More recently, VEGF gene therapy trials have been initiated to measure improved vascular function (Isner, *Lancet* 1996, 348, 370–374).

Endometriosis

Endometriosis also requires angiogenesis and neovascularization to permit the establishment and growth of endometriotic cells outside the uterus. Endometriosis is the most prevalent cause of female infertility, and affects approximately 6 million women in the U.S. The disease is most commonly characterized by the growth of endometrium in the peritoneal cavity where it proliferates, invades, secretes, desquamates, and accumulates with each ovarian cycle. Abdominal pain, fibrosis, rare ascites formation, and adhesions of intra-abdominal structures, result.

Endometriosis has been linked to increased levels of angiogenic factors and specifically to elevated VEGF levels (L. Brown et al., *Lab. Invest.*, 1997, 76, 245–255; J. Shifren et al., *J. Clin. Endocrinol. Metab.*, 1996, 81, 3112–3118; J. McLaren et al., *Hum. Reprod.*, 1996, 11, 220–223). During the menstrual cycle, expression of Flt is constant but that of kinase insert domain containing receptor (FLK-1/KDR) is increased in the luteal phase, at which time the cells migrate in response to VEGF. FLK-1/KDR expression and the migratory response are significantly higher in patients with endometriosis (J. McLaren, et al., *J. Clin. Invest.* 1996, 98, 482). Thus it is likely that the methods of the invention will be able to prevent or inhibit the growth of endometriotic cells outside the uterus.

III. Biological Activity of Indolinone Compounds

Indolinone compounds of the invention can be tested for their ability to activate or inhibit protein kinases in biological assays. The methods used to measure indolinone modulation of protein kinase function are described in U.S. application Ser. No. 08/702,232, filed Aug. 23, 1996, entitled "Indolinone Combinatorial Libraries and Related Products and Methods for the Treatment of Disease" by Tang et al., incorporated herein by reference in its entirety, including any drawings. Indolinone compounds of the invention were tested for their ability to inhibit the FLK protein kinase. Further activities and methods are described in U.S. patent application Ser. No. 60/045,566, filed May 5, 1997, entitled "FLK Specific Indolinone Compounds and Related Products and Methods for the Treatment of Disease" by McMahon et al., and U.S. patent application Ser. No.

08/915,366, filed Aug. 20, 1997, entitled "Indolinone Combinatorial Libraries and Related Products and Methods for the Treatment of Disease" by Tang et al., both of which are hereby included herein by reference in their entirety including any figures and drawings.

Assays to determine the biological activity of Indolinone compounds for protein tyrosine kinases include Enzyme linked immunosorbent assays (ELISA), cell growth assays, soft agar assays, sulforhodamine B (SRB) growth assays, and BrdU incorporation assays. Standard assays are well-known in the art and can be easily modified to apply to the protein tyrosine kinases and indolinone compounds of the invention.

An ELISA may be used to detect and measure the presence of tyrosine kinase activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. Of Microbiology, Washington, D.C.

Cell growth assays, soft agar assays, SRB assays, and BrdU incorporation assays may be conducted to measure the effect of the claimed compounds upon cell growth as a result of the compound's interaction with one or more protein tyrosine kinases. These assays may be generally applied to measure the activity of a compound against any particular kinase.

IV. Administration of Pharmaceutical Agent Formulations

Methods of determining the dosages of compounds to be administered to a patient and modes of administering compounds to an organism are disclosed in U.S. application Ser. No. 08/702,232, filed Aug. 23, 1996 and International patent publication number WO 96/22976, published Aug. 1, 1996, both of which are incorporated herein by reference in their entirety, including any drawings. Those skilled in the art will appreciate that such descriptions are applicable to the present invention and can be easily adapted to it.

The proper dosage depends on various factors such as the type of disease being treated, the particular composition being used, and the size and physiological condition of the patient. More specifically, the administered amount is the amount of compound required to effectively prevent development or alleviate symptoms of the disease or disorder in the subject being treated. Such a determination can be made by those of ordinary skill in the art in determining therapeutic dosages and is within the scope of routinely determined tasks.

Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans. However, the final dose will be determined in clinical trials based on clinical endpoints well-known in the art.

Plasma half-life and biodistribution of the drug and metabolites in the plasma, tumors, and major organs can also be determined to facilitate the selection of drugs most appropriate to inhibit a disorder. For example, HPLC analysis can be performed on the plasma of animals treated with the drug and the location of radio-labeled compounds can be determined using detection methods such as X-ray, CAT scan, autoradiography, and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out in a suitable animal test (e.g., mice in the example below) as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polynorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cell proliferative disorders the expected daily dose of an indolinone compound of the invention is 1 to 1000 $mg/m^2/day$, preferably 10 to 500 $mg/m^2/day$, and most preferably 10 to 250 $mg/m^2/day$. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

Routes of administration of the compounds or pharmaceutical compositions containing compounds of the present invention may include, but are not limited to, oral, rectal, transmucosal or intestinal administration; intramuscular, subcutaneous, intramedullary injections, as well as intrathecal, direct intraventricular, intravenous, intraperitoneal, intranasal, or intraocular injections; transdermal, topical, vaginal and the like. Dosage forms include, but are not limited to, tablets, troches, dispersions, suspensions, suppositories, solutions, patches, capsules, creams, minipumps, etc. The compounds of this invention may also be administered locally via an injection or in a targeted drug delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in a form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration or other governmental agencies for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of arthritis, endometriosis, ocular neovascularization, solid tumor growth and metastases, and excessive scarring during wound healing.

V. Indolinone Compound Formulations

The methods of the invention include the administration of indolinone compounds to patients in formulations. Formulations for indolinone compounds are described in U.S. application Ser. No. 08/702,232, filed Aug. 23, 1996 and in International patent publication No. WO 96/22976. Some indolinone compounds are insoluble in aqueous environments, so they require the addition of compounds that can be solubilize them before administration of the pharmaceutical agents to a patient. Specific formulations, methods of making and methods of use for hydrophobic indolinone compounds are described in U.S. Pat. No. 5,610,173 entitled "Formulations for Lipophilic Compounds" by D. Schwartz et al., U.S. patent application Ser. No. 09/034,374, entitled "Formulations for Hydrophobic Pharmaceutical Agents," filed Mar. 4, 1998, and the PCT application PCT/US98/04134, of the same title, also filed Mar. 4, 1998, all hereby incorporated by reference herein in their entirety including any drawings, figures, or tables. The components of the formulations bind to the hydrophobic regions of the pharmaceutical agents exposing the polar regions of the solubilizing components to the solvent environment. This encapsulation of the pharmaceutical agents renders them soluble in aqueous environments.

Formulations may comprise carriers, diluents, fillers, binders, and other excipient(s) at the dosage level required to treat or ameliorate the disease and/or disorder. The compounds of this invention and/or compositions thereof may be enclosed or encapsulated in an ingestible carrier in the form of a capsule, sachet, cachet, paper or other container or by a disposable container such as an ampule. A carrier or diluent may be semi-solid, solid or liquid, which serves as a vehicle, excipient, or medium for the active therapeutic substance. Diluents and carriers suitable for pharmaceutical compositions of the present invention are known to one of ordinary skill in the art.

EXAMPLES

The examples below are non-limiting and are merely representative of various aspects and features of the present invention. The examples describe methods for synthesizing compounds of the invention and methods for measuring an effect of a compound on the function of protein tyrosine kinases.

The cells used in the methods are commercially available. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Example 1

Synthesis of Indolinone Compounds

Descriptions of methods for the general synthesis of indolinone compounds are provided in U.S. application Ser. No. 08/702,282, which is incorporated herein by reference in its entirety, including any drawings and figures.

Indolinone compounds of the present invention may be synthesized according to known techniques. The following represent preferred methods for synthesizing the compounds of the invention.

1. General Syntheses of 3-Substituted-2-Indolinone Analogs

The following general methodologies were used to synthesize 3-substituted-2-indolinone compounds of the invention.

i. Method A

A reaction mixture of the proper oxindole (2-indolinone) (1 equiv.), the appropriate aldehyde (1.2 equiv.), and piperidine (0.1 equiv.) in ethanol (1–2 mL/1 mmol oxindole) was stirred at 90° C. for 3–5 h. After cooling, the precipitate was filtered, washed with cold ethanol, and dried to yield the target compound.

ii. Method B

Preparation of The Proper Aldehydes via Vilsmeier Reaction.

To a solution of N,N-dimethylformamide (1.2 equiv.) in 1,2-dichloroethane (2.0 ml/1.0 mmole of starting material) was added dropwise phosphorus oxychloride (1.2 equiv.) at 0° C. The ice-bath was removed and the reaction mixture was further stirred for 30 min. The proper starting material (1.0 equiv.) was added to the above solution portionwise and the reaction mixture was stirred at 50–70° C. for 5 h–2 days. The reaction mixture was poured into ice-cold 1 N sodium hydroxide solution (pH=9 after mixing) and the resulting mixture was stirred at room temperature for 1 h. The organic layer was separated and the aqueous layer was extracted with ethyl acetate. The combined organic layer was washed with brine until pH=7, dried over anhydrous sodium sulfate and evaporated. The residue was chromatographed on a silica gel column eluting with a solvent mixture of ethyl acetate and hexane to afford the title compound.

Synthesis for 3-Substituted-2-Indolinone Analogs.

A reaction mixture of the proper oxindole (2-indolinone) (1 equiv.), the appropriate aldehyde (1.2 equiv.), and piperidine (0.1 equiv.) in ethanol (1–2 ml/1 mmol oxindole) was stirred at 90° C. for 3–5 h. After cooling, the precipitate was filtered, washed with cold ethanol and dried to yield the target compound.

2. 5-Amino-3-(3,5-diethyl-1H-pyrrol-2-ylmethylene)-1,3-dihydro-indol-2-one

2-Oxindole (6.5 g) was dissolved in 25 mL of concentrated sulfuric acid and the mixture maintained at −10–15° C. while 2.1 mL of fuming nitric acid was added dropwise. After the addition of the nitric acid, the reaction mixture was stirred at 0° C. for 0.5 hr and poured into ice-water. The precipitate was collected by filtration, washed with water and crystallized from 50% acetic acid. The final crystalline product was then filtered, washed with water and dried under vacuum to give 6.3 g (70%) of 5-nitro-1,3-dihydro-indol-2-one.

5-Nitro-1,3-dihydro-indol-2-one (6.3 g) was hydrogenated in methanol over 10% palladium on carbon to give 3.0 g (60% yield) of 5-amino-1,3-dihydro-indol-2-one as a white solid.

5-Amino-1,3-dihydro-indol-2-one (1.8 g) was refluxed in 20 mL of dibutyl dicarbonate for 1 hr. The reaction mixture was cooled to room temperature and poured into ice water. The white precipitate was filtered, washed with water, and dried in a vacuum oven overnight to give 2.75 g (91.7%) of (2-oxo-2,3-dihydro-1H-indol-5-yl)-carbamic acid tert-butyl ester as a white solid.

Condensation of (2-oxo-2,3-dihydro-1H-indol-5-yl)-carbamic acid tert-butyl ester with 3,5-diethyl-H-pyrrole-2-carbaldehyde using Method A gave [3-(3,5-diethyl-1H-pyrrol-2-ylmethylene)-2-oxo-2,3-dihydro-1H-indol-5-yl]-carbamic acid tert-butyl ester.

[3-(3,5-diethyl-1H-pyrrol-2-ylmethylene)-2-oxo-2,3-dihydro-1H-indol-5-yl]-carbamic acid tert-butyl ester in 50% trifluoroacetic acid in dichloromethane was stirred at room temperature for 2 hrs and concentrated. The red residue was suspended in saturated sodium bicarbonate solution. The precipitate was filtered, washed with water until pH 6 and dried overnight to give 5-amino-3-(3,5-diethyl-1H-pyrrol-2-ylmethylene)-1,3-dihydro-indol-2-one.

3. Synthesis of 4-Methyl-3-(3-methyl-thiophen-2-ylmethylene)-1,3-dihydro-indol-2-one Diethyl oxalate (30 mL) in 20 mL of dry ether was added with stirring to 19 g of potassium ethoxide suspended in 50 mL of dry ether. The mixture was cooled in an ice bath and 20 mL of 3-nitro-o-xylene in 20 mL of dry ether was slowly added. The thick dark red mixture was heated to reflux for 0.5 hr, concentrated to a dark red solid, and treated with 10% sodium hydroxide until almost all of the solid dissolved. The dark red mixture was treated with 30% hydrogen peroxide until the red color changed to yellow. The mixture was treated alternately with 10% sodium hydroxide and 30% hydrogen peroxide until the dark red color was no longer present. The solid was filtered off and the filtrate acidified with 6 N hydrochloric acid. The resulting precipitate was collected by vacuum filtration, washed with water, and dried under vacuum to give 9.8 g (45% yield) of 1-methyl-6-nitrophenylacetic acid as an off-white solid. The solid was hydrogenated in methanol over 10% palladium on carbon to give 9.04 g of 4-methyl-1,3-dihydro-indol-2-one as a white solid.

4-Methyl-1,3-dihydro-indol-2-one (189 mg), 147 mg of 6-methoxy-2-oxindole, and 1 drop of piperidine in 2 mL of ethanol were heated to 100° C. for 4 hrs. The reaction mixture was cooled and the precipitate was filtered, washed with cold ethanol and dried in a vacuum oven to give 221 mg of 4-methyl-3-(3-methyl-thiophen-2-ylmethylene)-1,3-dihydro-indol-2-one (Compound III) (87%) as a brown solid.

$^1$HNMR (360 MHz, DMSO-d6) δ 10.53 (s, br, 1H, NH-1), 7.87 (s, 1H, H-vinyl), 7.75 (d, J=5.25 Hz, 1H, H-5'), 7.09–7.11 (m, 2H, H-6, 4'), 6.81 (d, J=7.66 Hz, 1H, H-5), 6.73 (d, J=7.77 (d, J=7.77 Hz, 1H, H-7), 2.60 (s, 3H, $CH_3$-4), and 2.46 (s, 3H, $CH_3$-3').

4. Synthesis of 3-[4-Methyl-5-(2-oxo-1,2-dihydro-indol-3-ylidenemethyl)-1H-pyrrol-3-yl]-propionic acid Sodium metal (1.5 g) was placed in a 3 L 3-neck round bottom flask equipped with a thermometer, a reflux condenser, and mechanical stirring, and placed in an oil bath. Absolute ethanol (1 L) was added with stirring. When the sodium had dissolved, 350 g of pentan-2,4-dione was added all at once, and then 310 g of ethyl acrylate was added over 30 min. The mixture was refluxed for 2.5 hrs and then allowed to cool to room temperature overnight. Glacial acetic acid (3 mL) was added and the solvent removed by rotary evaporation. The residue was filtered through a pad of diatomaceous earth and distilled through a wiped film still at 0.1 mm. The distillate was redistilled through a 10 inch vacuum jacketed Vigreux column to give 518 g of ethyl 5-acetyl-4-oxohexanoate, BP 84–92° C. at 0.2–0.7 mm.

To a 5 L three-neck flask, equipped with a thermometer and a mechanical stirrer and heated on a steam bath, was added 350 g of ethyl 5-acetyl-4-oxohexanoate, 329 g of diethyl aminomalonate hydrochloride, 133 g of sodium acetate, and 1.2 L of acetic acid. The mixture was heated to 99° C. over 37 minutes. By 62° C., carbon dioxide evolution was already rapid. After a total of 35 minutes at 99° C., gas evolution had greatly slowed. After another hour, the mixture was cooled, the sodium chloride removed by vacuum filtration, and the solvent evaporated. The residue was mixed with 1 L of cold water. The precipitate was collected by vacuum filtration, washed with 400 mL of water, and dissolved in 1 L of hot 95% ethanol. The solution was treated with 20 g of Darco G-60, hot-filtered, and cooled to room temperature. The crystalline solid was collected by vacuum filtration, washed twice on the filter with 200 mL of 50% ethanol each time, and dried under vacuum at 70° C. to give 285 g (64% yield) of 2-ethoxycarbonyl-4-(2-ethoxycarbonylethyl)-3,5-dimethylpyrrole. The filtrate was refrigerated overnight to give another 53.1 g (11.9% yield) of product, for a total yield of 75.9%.

2-Ethoxycarbonyl-4-(2-ethoxycarbonylethyl)-3,5-dimethylpyrrole (285 g) and 3500 mL of ethyl ether were placed in a 5 L, 3 neck flask equipped with a mechanical stirrer, a reflux condenser, and an addition funnel, and cooled in an ice bath. Sulfuryl chloride (435 g) was added dropwise over 145 min. As the addition proceeded, the mixture turned cloudy and green, then cleared. At the end of the addition, the mixture was clear and faintly yellow. The mixture was stirred for 1 additional hr, and then heated to reflux for 1 hr. The mixture was cooled and rotary evaporated, diluted with 1500 mL of ether, and rotary evaporated again. The dilution and evaporation was repeated again. The residue was added to 8 L of water containing 802 g of acetic acid and 535 g of sodium hydroxide. The mixture was briefly heated to 85° C. and then allowed to cool overnight with stirring. The aqueous layer, which contained solids, was separated and extracted with 800 mL of ether. The solids and the ether layer were added to 2.5 L of water, containing 300 g of sodium carbonate, stirred for 1 hr, and filtered to remove a small amount (~7 g) of solid. Sulfurous acid (137 g) was added to the mixture, and the resulting precipitate washed twice with 250 mL of water, and dried under vacuum to give 56.4 g of product. Sulfurous acid (92 g) was again added to the filtrate, and the resulting precipitate washed twice with 0.5 L of water, and dried under vacuum to give 220 g of product, for a total of 276.4 g (86.8% yield) of 2-carboxy-5-ethoxycarbonyl-3-(2-ethoxycarbonylethyl)-4-methylpyrrole.

2-Carboxy-5-ethoxycarbonyl-3-(2-ethoxycarbonylethyl)-4-methylpyrrole (50.5 g) and 400 mL of 10% sodium hydroxide solution was heated to 180° C. in a Parr autoclave for 90 min. This process was repeated 4 more times on a total of 252.5 g of 2-carboxy-5-ethoxycarbonyl-3-(2-ethoxycarbonylethyl)-4-methylpyrrole. The five solutions were combined and rotary evaporated to a volume of about 1.8 L of thick black residue. The mixture was cooled to 10° C. in a water bath, and 50% sulfuric acid was slowly added until the pH was 2, keeping the temperature <20° C. Ethyl ether (1400 mL) was added and the mixture filtered, saving the precipitate. The precipitate was extracted in a Soxhlet apparatus with 500 mL of ether. The combined ether layers were washed with 250 mL, and then 150 mL, of water, and the water layers back extracted with 150 mL of ether. All the ether layers were rotary evaporated and the residue dried to give 123.5 g of 3-(2-carboxyethyl)-4-methylpyrrole.

3-(2-Carboxyethyl)-4-methylpyrrole (123 g) was mixed with 1500 mL of ethyl ether and 250 mL of methanol in a magnetically stirred receiver flask. A separate 3 L, 3 neck round bottom flask was equipped with magnetic stirring, a distillation head and condenser leading to the inlet of the receiver flask, and heated in a water bath. Into the 3 L flask was placed 240 g of Diazald, dissolved in 1800 mL of ethyl ether, and a solution of 73 g of potassium hydroxide, dissolved in 360 mL of 95% ethanol and 112 mL of water. The 3 L flask was stirred and heated to 65–75° C. in a water bath, and the diazomethane-ether mixture was distilled into the stirred receiver flask over about 2.5 hrs. Ethyl ether (200 mL) was added to the 3 L flask, and the distillation continued until complete. The receiver flask was stirred for another 30 minutes, and then 10 mL of acetic acid was added. The mixture was extracted twice with 500 mL of water each time, and then twice with 200 mL of saturated sodium bicarbonate each time. The ether layer was dried over anhydrous sodium sulfate, and distilled to leave a dark fluid residue. The residue was distilled twice through a 4 inch Vigreux column and once through a 10 inch vacuum-jacketed Vigreux column to give 108 g (80.6% yield) of 3-(2-methoxycarbonylethyl)-4-methylpyrrole. BP 108–113 C at 0.5 mm.

Dimethylformamide was charged to a 500 mL, 3 neck round bottom flask equipped with mechanical stirring, a thermometer, and a dropping funnel, and maintained under a nitrogen atmosphere. The flask was cooled to 0° C., and 58.4 mL of phosphorus oxychloride was added dropwise over 80 min. Dichloroethane (280 mL) was added, and the mixture was allowed to warm to room temperature, and then was cooled to −10° C. 3-(2-Methoxycarbonylethyl)-4-methylpyrrole (55.7 g) dissolved in 80 mL of dichloroethane was added dropwise over 1 hr, and the mixture stirred for another 35 min. The mixture was rotary evaporated at <30° C. The fluid residue was poured into 2700 mL of ice-cold 2 N sodium hydroxide solution. The resulting solution was heated to 88° C. over 20 minutes and then was maintained at this temperature for an additional 30 minutes. The solution was cooled to ambient temperature and was extracted with 200 mL of ethyl ether. The aqueous solution was cooled to 0° C. and was acidified to pH 3.5 by slowly adding about 1350 mL of 5 N hydrochloric acid. The yellow precipitate was collected by vacuum filtration, was washed four times with 100 mL of water each time, and was dried in a vacuum oven at ambient temperature to give 54.4 g (90.2% yield) of crude 4-(2-carboxyethyl)-2-formyl-3-methylpyrrole.

The crude material was refluxed in a mixture of 425 mL of ethanol and 700 mL of ethyl ether, and was hot filtered to remove the insoluble residue, which was retained. The filtrate was put in the freezer and the resulting precipitate was collected by vacuum filtration and was washed with 50 mL of ether. The filtrate was used to again extract the insoluble residue, was hot filtered, and was put in the freezer. The resulting precipitate and the first precipitate were combined to give 26.1 g of 4-(2-carboxyethyl)-2-formyl-3-methylpyrrole as a brown powder, MP 149.0–150.3° C. The filtrate was combined with the filtrate from a previous preparation and concentrated to give 43 g of a brown solid. The solid was refluxed in a mixture of 500 mL of ether and 100 mL of ethanol, was filtered, the filtrate treated with Norit at reflux, and was hot filtered again. The filtrate was put in the freezer to give 3 additional crops of 4-(2-carboxyethyl)-2-formyl-3-methylpyrrole, 7.7 g, MP 148–151° C., 3.2 g MP 128–134° C. and 4.1 g, MP 148.2–150.0° C.

4-(2-Carboxyethyl)-2-formyl-3-methylpyrrole (9.0 g) and 6.0 g of 2-oxindole in 50 mL of ethanol were heated to 70° C. in a 250 mL, 3-neck round bottom flask equipped with a thermometer, a reflux condenser, and magnetic stirring. When most of the solids had dissolved, 4.5 g of piperidine was slowly added, and the mixture was refluxed for 4 hrs. Acetic acid (12 mL) was slowly added, resulting in a copious precipitate. The mixture was refluxed for 5 min, was cooled to room temperature, and the precipitate was collected by vacuum filtration and was washed with 30 mL of ethanol. The precipitate was slurry-washed at reflux in 30 mL of ethanol, was cooled to room temperature, was collected by vacuum filtration, was washed with 20 mL of ethanol, and was dried under vacuum to give 11.9 g (80% yield) of 3-[4-methyl-5-(2-oxo-1,2-dihydro-indol-3-ylidenemethyl)-1Hpyrrol-3-yl]-propionic acid (Compound V), as an orange solid.

$^1$HNMR (360 MHz, DMSO-d6) δ 13.29 (s, br, 1H, NH-1'), 12.05 (s, br, 1H, COOH), 10.78 (s, br, 1H, NH-1), 7.73 (d, J=7.43 Hz, 1H, H-4), 7.61 (s, 1H, H-vinyl), 7.13 (d, J=2.75 Hz, 1H, H-2'), 7.10 (t, J=7.43 Hz, 1H, H-6), 6.97 (t, J=7.43 Hz, 1H, H-5), 6.85 (d, J=7.43 Hz, 1H, H-7), 2.64 (t, J=7.38 Hz, 2H, $CH_2CH_2COOH$), 2.46 (t, J=7.38 Hz, 2H, $CH_2CH_2COOH$), 2.25 (s, 3H, $CH_3$). MS m/z (relative intensity, %) 297 ([M+1]$^+$, 100).

5. Synthesis of 3-[2,4-Dimethyl-5-(2-oxo-1,2-dihydro-indol-3-ylidenemethyl)-1H-pyrrol-3-yl]-propionic acid Methyl 4-acetyl-5-oxo-hexanoate (500 g) and 597 g of diethyl aminomalonate hydrochloride were added to 500 mL of acetic acid mechanically stirring at 40–50° C. in a 3 L, three-neck, round bottom flask equipped with a reflux condenser and heated in an oil bath. Sodium acetate (241 g) was added, and the funnel was washed with 180 mL of acetic acid. The reaction was heated to an internal temperature of 101° C. over 2 hrs at which time heating was reduced. Gas evolution began at a temperature of 74° C. and had greatly slowed after 2 hrs. After an additional 1 hr, the internal temperature was 97° C., gas evolution had stopped, and the mixture which contained solid sodium chloride was light pink in color. The oil bath was removed and was replaced with a cold water bath. 1.4 L of water was slowly added at a temperature of 50° C., and the mixture was stirred until the temperature reached 10° C. The solids were collected by vacuum filtration, were washed three times with 300 mL of water each time, and were dried at 40–50° C. under vacuum for two days to give 614.3 g (90.5% yield) of 2,4-dimethyl-5-ethoxycarbonyl-3-(2-metboxycarbonylethyl)pyrrole as an off-white solid.

2,4-Dimethyl-5-ethoxycarbonyl-3-(2-methoxycarbonylethyl)pyrrole (228 g) and 720 mL of 5 N sodium hydroxide were magnetically stirred in a 3 L, three-neck, round bottom flask equipped with a reflux condenser and heated in an oil bath. Reflux occurred at a bath temperature of 130° C., at which time the heating rate was decreased. After one hr of reflux, the bath temperature was 110° C., all solids were dissolved, and thin layer chromatography showed the hydrolysis to be complete. 10 N hydrochloric acid (390 mL) was slowly added to give a pH of 2–3. After about 50% of the acid was added at a bath temperature of 100° C., gas evolution began. As more acid was added, gas evolution increased. After 360 mL of acid was added, the pH of the clear pale yellow mixture was about 4 and an oil started to form. As the remaining acid was added, the oil solidified as a dirty yellow solid on top of the aqueous layer. The pH was 2–3. The mixture was stirred and was allowed to cool at ambient temperature to 38° C. (inside temperature), and was then cooled to 4° C. in an ice bath. The reddish solids were collected by vacuum filtration, washed thoroughly with water and dried for 2 days in a vacuum oven at 40° C. to give 65.7 g (49% yield, corrected for the removal of 10% of the reaction mixture) of 3-(2-carboxyethyl)-2,4-dimethylpyrrole.

Dimethylformamide (28.5 g) in 250 mL of dichloromethane in a 1 L, three-neck, round bottom flask equipped with magnetic stirring, a thermometer, and a dropping funnel, was cooled in an ice-salt bath to −1° C. Phosphorus oxychloride (59.3 g) was slowly added, and the funnel was washed with 25 mL of dichloromethane. The maximum temperature reached by the mixture was 5° C. The mixture was stirred for 15 min at which time the temperature was −3° C. Solid 3-(2-Carboxyethyl)-2,4-dimethylpyrrole (32.6 g) was added in portions over 15 min. The maximum temperature reached by the mixture was 7° C. The reddish-black mixture was stirred for 30 min more, and then was heated to reflux for 1 hr. The mixture was cooled to 15° C. and 300 mL of water was added, leading to a vigorous reaction and temperature increase. The mixture was stirred and was cooled to 22° C., and the layers were separated and were saved. The organic layer was extracted with an additional 100 mL of water, and the aqueous layers combined and washed with 50 mL of dichloromethane. The organic layers were discarded. The aqueous layer was adjusted to pH 11 with ~180 mL of 10 N sodium hydroxide. The temperature increased to 40° C. The mixture was stirred for 30 min, at which time the temperature was 27° C. The mixture was acidified to pH 2 with ~120 mL of 10 N hydrochloric acid, which increased the temperature to 30° C. Ethyl acetate (150 mL) was added and the mixture was stirred to extract the product. During stirring, a considerable amount of black solid appeared on top of the water layer. The ethyl acetate layer was separated, and the aqueous layer and solid were extracted twice with 100 mL of ethyl acetate each time. The solid still present was collected by vacuum filtration, was washed thoroughly with water, and was dried under vacuum at 40° C. to give 12 g (31% yield) of 3-(2-carboxyethyl)-2,4-dimethyl-5-formylpyrrole as a brownish-black solid. Thin layer chromatography (dichloromethane:acetic acid, 95:5, silica gel) Rf 0.7, colored spot at origin. The ethyl acetate layers were combined, were dried over anhydrous sodium sulfate, and were evaporated to a brownish-black solid which was dried under vacuum at 40° C. to give 21 g (55% yield, total yield 86%) of 3-(2-carboxyethyl)-2,4-dimethyl-5-formylpyrrole, identical in appearance to the previous solid by thin layer chromatography.

3-(2-Carboxyethyl)-2,4-dimethyl-5-formylpyrrole (18.2 g) and 11.7 g of 2-oxindole were dissolved in 100 mL of ethanol by heating in an oil bath in a 250 mL round bottom flask equipped with magnetic stirring and a reflux condenser. Pyrrolidine (7.0 g) was added, and the reaction mixture was refluxed for 2 hrs at which time a large quantity of brown-black solid was present. Thin layer chromatography (ethyl acetate:ethanol:acetic acid 96:2:2, silica gel) showed the absence of oxindole starting material. Eight mL of acetic acid was added and the mixture was refluxed for 15 min. The thick mixture was diluted with 50 mL of ethanol and was cooled to 10° C. The solid was collected by vacuum filtration and was washed with 50 mL of ethanol. The solid was stirred in 125 mL of ethanol at reflux for 10 min, was cooled to 10° C., was collected by vacuum filtration, and was washed with 50 mL of ethanol. The product was dried overnight at 45° C. under vacuum to give 25.5 g (88% yield) of 3-[2,4-dimethyl-5-(2-oxo-1,2-dihydro-indol-3-ylidenemethyl)-1H-pyrrol-3-yl]-propionic acid (Compound VI), as an orange solid.

¹HNMR (360 MHz, DMSO-d6) δ 13.38 (s, br, 1H, NH-1'), 12.05 (s, br, 1H, COOH), 10.70 (s, br, 1H, NH-1), 7.69 (d, J=7.39 Hz, 1H, H-4), 7.53 (s, 1H, H-vinyl), 7.06 (t, J=7.39 Hz, 1H, H-6), 6.95 (t, J=7.39 Hz, 1H, H-5), 6.85 (d, J=7.39 Hz, 1H, H-7), 2.63 (t, J=7.45 Hz, 2H, $CH_2CH_2COOH$), 2.34 (t, J=7.45 Hz, 2H, $CH_2CH_2COOH$), 2.28 (s, 3H, $CH_3$), and 2.24 (s, 3H, $CH_3$). MS m/z (relative intensity, %) 311 ([M+1]$^{+*}$, 100).

6. Synthesis of N-(2-Morpholin-4-yl-ethyl)-3-[2-(2-oxo-1,2-dihydro-indol-3-ylidenemethyl)-4,5,6,7-tetrahydro-1H-indol-3-yl]-propionamide 3-[2-(2-Oxo-1,2-dihydro-indol-3-ylidenemethyl)-4,5,6,7-tetrahydro-1H-indol-3-yl]-propionic acid (Compound VI) (1 g), 630 L of 2-morpholin-4-yl-ethylamine, and 530 mg of di-imidazol-1-yl-methanone, in 10 mL of N,N-dimethylformamide, were stirred at room temperature for 1 hr. The reaction mixture was poured into water. The precipitate was filtered and was suspended in hot ethanol. After the suspension was cooled to room temperature, the precipitate was filtered, was washed with ethanol, and was dried in an oven overnight to give N-(2-morpholin-4-yl-ethyl)-3-[2-(2-oxo-1,2-dihydro-indol-3-ylidenemethyl)-4,5,6,7-tetrahydro-1H-indol-3-yl]-propionamide (Compound VII).

¹HNMR (360 MHz, DMSO-d6) δ 13.22 (s, br, 1H, NH-1'), 10.70 (s, br, 1H, NH-1), 7.69 (s, br, 1H, NH), 7.61 (d, J=7.39 Hz, 1H, H-4), 7.55 (s, 1H, H-vinyl), 7.06 (t, J=7.39 Hz, 1H, H-6), 6.98 (t, J=7.39 Hz, 1H, H-S), 6.84 (d, J=7.39 Hz, 1H, H-7), 3.44 (t, J=4.63 Hz, 4H), 3.05–3.07 (m, 2H), 2.85–2.89 (m, 2H), 2.64–2.68 (m, 2H), 2.42–2.46 (m, 2H), 2.15–2.19 (m, 4H), and 1.70–1.77 (m, 4H). MS m/z (relative intensity, %) 449 ([M+1]$^{+*}$, 100).

7. 3-[2-(2-Oxo-1,2-dihydro-indol-3-ylidenemethyl)-4,5,6,7-tetrahydro-1H-indol-3-yl]-propionic acid 1-(Morpholin-4-yl)cyclohexene (20.1 g), 14.4 g of triethylamine, and 100 mL of dichloromethane, were charged to a 1 L, 3-neck round bottom flask equipped with a reflux condenser, mechanical stirring, a thermometer, and a dropping funnel. The mixture was refluxed for 15 min, and was cooled in a water bath to 15–20° C. With vigorous stirring, 18 g of ethyl succinyl chloride, dissolved in 40 mL of dichloromethane, was added over 5 min via the dropping funnel. At the end of the addition, the mixture contained a large amount of precipitate and was refluxing. Refluxing was continued for 30 min, and the mixture was cooled to ambient temperature in a water bath. The mixture was extracted twice, with 100 mL of water each time, and twice with 30 mL of brine each time, was dried over 5 g of anhydrous sodium sulfate, and was evaporated to give crude 1-(ethylsuccinyl)-2-(morpholin-4-yl)cyclohexene as an oil.

Crude 1-(ethylsuccinyl)-2-(morpholin-4-yl)cyclohexene (30 g), 26.7 g of diethyl aminomalonate hydrochloride, 10.8 g of sodium acetate, and 28 mL of glacial acetic acid were charged to a 1 L, 3-neck round bottom flask equipped with mechanical stirring, a reflux condenser, and heated in an oil bath. The mixture was heated to 108° C. over 30 min accompanied by the evolution of carbon dioxide and the formation of a precipitate of sodium chloride. The mixture was held at 100–108° C. for 2 hrs and was cooled to about 50 C in a water bath. Water (160 mL) and 160 mL of ethyl acetate were added. The precipitate dissolved. The ethyl acetate layer was separated and was washed twice with 100 mL of water each time, once with 70 mL of saturated sodium bicarbonate solution, and once with 50 mL of brine, and was dried over 10 g of anhydrous sodium sulfate and was rotary evaporated to give 30 g (85% yield) of crude 2-ethoxycarbonyl-3-(2-ethoxycarbonylethyl)-4,5,6,7-tetrahydroindole as an oil.

Crude 2-ethoxycarbonyl-3-(2-ethoxycarbonylethyl)-4,5,6,7-tetrahydroindole (30 g) and 80 mL of 5 N sodium hydroxide were refluxed for 80 min in a round bottom flask heated in an oil bath and equipped with magnetic stirring. The heater was turned off, but the flask was left in the hot bath, and about 44 mL of 10 N hydrochloric acid was cautiously added via a dropping funnel through the reflux condenser with vigorous stirring. When approximately 80% of the acid had been added, a large amount of carbon dioxide was evolved. The addition was continued until the pH was 2–3. The mixture was cooled in a water bath, and 200 mL of ethyl acetate was added to dissolve the oil that was present. The ethyl acetate layer was isolated and was washed 3 times with 50 mL of water each time, twice with 30 mL of brine each time, and was dried over 5 g of anhydrous sodium sulfate and was evaporated to give 15.5 g (80%) yield of crude 3-(2-carboxyethyl)-4,5,6,7-tetrahydroindole as a very dark sticky syrup.

Dimethylformamide (11.7 g) and 240 mL of dichloromethane in a 1 L, 3-neck round bottom flask equipped with magnetic stirring, a reflux condenser, and a dropping funnel, was cooled to –4° C. in an ice-salt bath maintained at –10° C. Phosphorus oxychloride (24.5 g) was rapidly added via the dropping funnel. The temperature increased to –3° C., and then, with further stirring, decreased to –7° C. Crude 3-(2-carboxyethyl)-4,5,6,7-tetrahydroindole dissolved in 160 mL of dichloromethane was added via the dropping funnel over 15 min keeping the temperature below 1° C. The mixture was refluxed for 10 min, cooled to 5° C., and diluted with 300 mL of water. The aqueous layer was evaporated and was saved, and the organic layer was extracted with another 30 mL of water. The aqueous layers were combined, were washed with 30 mL of dichloromethane and were cooled to 5° C. The aqueous layer was adjusted to pH 10 with about 48 mL of 10 N sodium hydroxide, accompanied by a temperature increase to 15° C. The mixture was then cooled to 10° C. and adjusted to pH 2–3 with about 48 ml of 10 N hydrochloric acid. The oil which formed solidified, and was collected by vacuum filtration, was washed three times with 20 mL of water each time, and was dried under high vacuum to give 5.5 g (31% yield) of 3-(2-carboxyethyl)-2-formyl-4,5,6,7-tetrahydroindole as a brown solid.

3-(2-Carboxyethyl)-2-formyl-4,5,6,7-tetrahydroindole (5.4 g), 3.57 g of 2-oxindole, and 25 mL of ethanol were heated to near reflux in a 250 mL, three-neck round bottom flask equipped with a reflux condenser and mechanical stirring. Piperidine (2.7 g) was slowly added, and the mixture was refluxed for 4 hrs. Thin layer chromatography (silica gel, ethyl acetate) showed only a trace of oxindole remaining. Acetic acid (8 mL) was slowly added, causing a voluminous precipitate. The mixture was refluxed for 5 min and was cooled to ambient temperature. The precipitate was collected by vacuum filtration and was washed with 20 mL of ethanol. The solids were slurry-washed by refluxing in 30 mL of ethanol, were cooled, were collected by vacuum filtration, were washed with 30 mL of ethanol, and were dried under high vacuum to give 5.5 g (68% yield) of 3-[2-(2-oxo-1,2-dihydro-indol-3-ylidenemethyl)-4,5,6,7-tetrahydro-1H-indol-3-yl]-propionic acid (Compound VIII), as an orange solid.

8. Synthesis of 3-[(4-Methylthien-2-yl)methylene]-2-indolinone

A reaction mixture of 133.0 mg of oxindole, 151.2 mg of the 4-methylthiophene-2-carboxaldehyde, and 3 drops of piperidine in 3 mL of ethanol was stirred at 90° C. for 3 h. After cooling, the precipitate was filtered, washed with cold ethanol, and dried to yield 147.3 mg (61%) of the title compound as a yellow solid.

9. Synthesis of 3-[(3-Methylpyrrol-2-yl)methylene]-2-indolinone

A reaction mixture of 133.0 mg of oxindole, 130.9 mg of the 3-methylpyrrole-2-carboxaldehyde, and 3 drops of piperidine in 2 mL of ethanol was stirred at 90° C. for 3 h. After cooling, the precipitate was filtered, washed with cold ethanol, and dried to yield 150.9 mg (67%) of the title compound as a yellow solid.

10. Synthesis of 3-[(3,4-Dimethylpyrrol-2-yl)methylene]-2-indolinone

3-[(3,4-Dimethylpyrrol-2-yl)methylene]-2-indolinone was synthesized as described in *J. Heterocyclic Chem.* 13:1145–1147 (1976).

Ethyl 4-methylpyrrol-3-carboxylate.

A solution of 11.86 g (0.1 moles) of ethyl crotonate and 19.50 g (0.1 moles) of p-toluenesulfonylmethylisocyanide in 500 mL of a 2:1 ether/dimethylsulfoxide was added dropwise into a suspension of 6.8 g of sodium hydride (60% mineral oil dispension, 0.17 moles) in ether at room temperature. Upon completion of addition the reaction mixture was stirred for 30 min and dilute with 400 mL of water. The aqueous layer was extracted with 3×100 mL of ether. The combined ether extracts were passed through a column of alumina eluting with dichloromethane. The organic solvent was evaporated and the resulting residue was solidified on standing. The solid was washed with hexane and dried at 40° C. in vacuum oven overnight to yield 12.38 g (80%) of the title compound.

Preparation of 3,4-Dimethylpyrrole.

To a solution of 23 g (80 mmoles) of sodium dihydrobis (2-methoxyehtoxy aluminate) was added dropwise of a solution of 5 g (34 mmoles) of ethyl 4-methylpyrrol-3-carboxylate in 50 mL of benzene at room temperature under nitrogen atmosphere. The reaction mixture was stirred for 18 h. Water (100 mL) was added to the reaction mixture. The organic layer was separated, washed with brine and dried over anhydrous sodium sulfate. The solvent was removed and the residue was distilled giving 1.2 g (44%) of the title compound.

Preparation of 3,4-Dimethylpyrrole-2-carboxaldehyde.

To a solution of 0.92 mL (12 mmoles) of N,N-dimethylformamide in 10 mL of 1,2-dichloroethane was added dropwise 1.0 mL (12 mmoles) of phosphorus oxychloride at 0° C. The ice-bath was removed and the reaction mixture was further stirred for 30 min. 3,4-Dimethylpyrrole (960.0 mg, 10 mmoles) was added to the above solution portionwise and the reaction mixture was stirred at 50° C. for 5 h. The reaction mixture was poured into ice-cold 1 N sodium hydroxide solution (pH=9 after mixing) and the resulting mixture was stirred at room temperature for 1 h. The organic layer was separated and the aqueous layer was extracted with ethyl acetate. The combined organic layer was washed with brine until pH=7, dried over anhydrous sodium sulfate and evaporated. The residue was chromatographed on a silica gel column eluting with a solvent mixture of ethyl acetate and hexane to afford 610 mg (50%) of the title compound.

3-[(3,4-Dimethylpyrrol-2-yl)methylene]-2-indolinone.

A reaction mixture of 67.0 mg (0.5 mmoles) of oxindole, 73.0 mg (0.6 mmoles) of the 3,4-dimethylpyrrole-2- carboxaldehyde, and 2 drops of piperidine in 2 mL of ethanol was stirred at 90° C. for 3 h. After cooling, the precipitate was filtered, washed with cold ethanol, and dried to yield 87.7 mg (37%) of the title compound as a yellow solid.

11. Synthesis of 3-[(2,4-Dimethyl-3-ethoxycarbonylpyrrol-5-yl)methylene]-2-indolinone A reaction mixture of 134.0 mg of oxindole, 234.3 mg of the 4-ethoxycarbonyl-3,5-dimethylpyrrole-2-carboxaldehyde, and 3 drops of piperidine in 3 mL of ethanol was stirred at 90° C. for 3 h. After cooling, the precipitate was filtered, washed with cold ethanol, and dried to yield 244.6 mg (79%) of the title compound as a yellow solid.

12. Synthesis of 3-[(2,4-Dimethylpyrrol-5-yl)methylene]-2-indolinone

A reaction mixture of 134.0 mg of oxindole, 147.8 mg of the 3,5-dimethylpyrrole-2-carboxaldehyde, and 3 drops of piperidine in 2 mL of ethanol was stirred at 90° C. for 3 h. After cooling, the precipitate was filtered, washed with cold ethanol, and dried to yield 136.7 mg (57%) of the title compound as a yellow solid.

13. Synthesis of 3-[(2-Methylmercaptothien-5-yl)methylene]-2-indolinone

A reaction mixture of 134.0 mg of oxindole, 189.9 mg of the 5-methylmercaptothiophene-2-carboxaldehyde, and 3 drops of piperidine in 2 mL of ethanol was stirred at 90° C. for 3 h. After cooling, the precipitate was filtered, washed with cold ethanol, and dried to yield 246.6 mg (90%) of the title compound as a orange solid.

14. Synthesis of 3-[(2-Methylthien-5-yl)methylene]-2-indolinone

A reaction mixture of 134.0 mg of oxindole, 151.42 mg of the 5-methylthiophene-2-carboxaldehyde, and 3 drops of piperidine in 2 mL of ethanol was stirred at 90° C. for 3 h. After cooling, the precipitate was filtered, washed with cold ethanol, and dried to yield 237.8 mg (99%) of the title compound as a yellow solid.

15. Synthesis of 3-[(3-Methylthien-2-yl)methylene]-2-indolinone

A reaction mixture of 134.0 mg of oxindole, 151.4 mg of the 3-methylthiophene-2-carboxaldehyde, and 3 drops of piperidine in 2 mL of ethanol was stirred at 90° C. for 3 h. After cooling, the precipitate was filtered, washed with cold ethanol, and dried to yield 157.8 mg (65%) of the title compound as a yellow solid.

16. Synthesis of 3-[(furan-2-yl)methylene]-2-indolinone

3-[(furan-2-yl)methylene]-2-indolinone is synthesized according to Method A.

17. Synthesis of 3-[(Thien-2-yl)methylene]-2-indolinone

3-[(Thien-2-yl)methylene]-2-indolinone is synthesized according to Method A.

18. Synthesis of 3-[2-[3,5-Di-(trifluoromethyl)phenyl]furan-5-yl]methylene]-2-indolinone 3-[2-[3,5-Di-(trifluoromethyl)phenyl]furan-5-yl]methylene]-2-indolinone is synthesized according to Method A.

19. Synthesis of 3-[(3-(2-carboxyethyl)-4-methylpyrrol-5-yl)methylene]-2-indolinone 3-[(3-(2-carboxyethyl)-4-methylpyrrol-5-yl)methylene]-2-indolinone is synthesized according to Method A.

20. Synthesis of 3-[(3,4-Dibromo-5-methylpyrrol-2-yl)methylene]-2-indolinone

3-[(3,4-Dibromo-5-methylpyrrol-2-yl)methylene]-2-indolinone is synthesized according to Method B.

21. Synthesis of 3-[(3,4-Dimethyl-2-formylpyrrole-5-yl)methylene)-2-indolinone

3-[(3,4-Dimethyl-2-formylpyrrole-5-yl)methylene)-2-indolinone is synthesized according to Method A.

22. Synthesis of 3-{[4-(2-metboxycarbonylethyl)-3-methylpyrrol-5-yl]methylene}-2-indolinone 3-{[4-(2-methoxycarbonylethyl)-3-methylpyrrol-5-yl]methylene}-2-indolinone is synthesized according to Method A.

23. Synthesis of 3-[2-Iodofuran-5-yl)methylene]-2-indolinone

3-[2-Iodofuran-5-yl)methylene]-2-indolinone is synthesized according to Method A.

24. Synthesis of 3-[(3-Ethoxycarbonyl-2-methylfuran-5-yl)methylene]-2-indolinone 3-[(3-Ethoxycarbonyl-2-methylfuran-5-yl)methylene]-2-indolinone is synthesized according to Method A.

25. Synthesis of 3-[(3-Bromothiene-2-yl)methylene]-2-indolinone

3-[(3-Bromothiene-2-yl)methylene]-2-indolinone is synthesized according to Method A.

26. Synthesis of 3-[(2-Chlorothiene-5-yl)methylene)-2-indolinone

3-[(2-Chlorothiene-5-yl)methylene)-2-indolinone is synthesized according to Method A.

27. Synthesis of 3-[(2,3-Dimethylfuran-5-yl)methylene]-2-indolinone

3-[(2,3-Dimethylfuran-5-yl)methylene]-2-indolinone is synthesized according to Method A.

28. Synthesis of 3-[(5-Nitrothien-2-yl)methylene]-2-indolinone

3-[(5-Nitrothien-2-yl)methylene]-2-indolinone is synthesized according to Method A.

29. Synthesis of 3-[(2-Carboxythien-5-yl)methylene]-2-indolinone

3-[(2-Carboxythien-5-yl)methylene]-2-indolinone is synthesized according to Method A.

30. Synthesis of 3-[(2-Bromothiene-5-yl)methylene]-2-indolinone

3-[(2-Bromothiene-5-yl)methylene]-2-indolinone is synthesized according to Method A.

31. Synthesis of 3-[(4-Bromothiene-2-yl)methylene]-2-indolinone

3-[(4-Bromothiene-2-yl)methylene]-2-indolinone is synthesized according to Method A.

32. Synthesis of 3-[(2-Sulphonylfuran-5-yl)methylene]-2-indolinone sodium salt

3-[(2-Sulphonylfuran-5-yl)methylene]-2-indolinone sodium salt is synthesized according to Method A.

33. Synthesis of 3-[(Furan-2-yl)methylene]-2-indolinone

3-[(Furan-2-yl)methylene]-2-indolinone is synthesized according to Method A.

34. Synthesis of 3-[(2-Methylfuran-5-yl)methylene]-2-indolinone

3-[(2-Methylfuran-5-yl)methylene]-2-indolinone is synthesized according to Method A.

34. Synthesis of 3-[(2-Ethylfuran-5-yl)methylene]-2-indolinone

3-[(2-Ethylfuran-5-yl)methylene]-2-indolinone is synthesized according to Method A.

36. Synthesis of 3-[(2-Nitrofuran-5-yl)methylene]-2-indolinone

3-[(2-Nitrofuran-5-yl)methylene]-2-indolinone is synthesized according to Method A.

37. Synthesis of 3-[(5-Bromofuran-2-yl)methylene]-2-indolinone

3-[(5-Bromofuran-2-yl)methylene]-2-indolinone is synthesized according to Method A.

38. Synthesis of 3-[(2-Ethylthien-5-yl)methylene]-2-indolinone

3-[(2-Ethylthien-5-yl)methylene]-2-indolinone is synthesized according to Method A.

39. Synthesis of 3-[(4,5-Dimethyl-3-ethylpyrrol-2-yl)methylene]-2-indolinone

3-[(4,5-Dimethyl-3-ethylpyrrol-2-yl)methylene]-2-indolinone is synthesized according to Method A.

40. Synthesis of 3-[(5-Ethoxycarbonyl-4-ethoxycarbonylethyl-3-ethoxycarbonylmethylpyrrol-2-yl)methylene]-2-indolinone 3-[(5-Ethoxycarbonyl-4-ethoxycarbonylethyl-3-ethoxycarbonylmethylpyrrol-2-yl)methylene]-2-indolinone is synthesized according to Method A.

41. Synthesis of 3-[(5-Carboxy-3-ethyl-4-methylpyrrol-2-yl)methylene]-2-indolinone 3-[(5-Carboxy-3-ethyl-4-methylpyrrol-2-yl)methylene]-2-indolinone is synthesized according to Method A.

42. Synthesis of 3-[(3,5-Diiodo-4-methylpyrrol-2-yl)methylene]-2-indolinone

3-[(3,5-Diiodo-4-methylpyrrol-2-yl)methylene]-2-indolinone is synthesized according to Method A.

43. Synthesis of 3-[(5-Chloro-3-methoxycarbonyl-4-methoxycarbonylmethylpyrrol-2-yl)methylene]-2-indolinone 3-[(5-Chloro-3-methoxycarbonyl-4-methoxycarbonylmethylpyrrol-2-yl)methylene]-2-indolinone is synthesized according to Method A.

44. Synthesis of 3-[(3-Acetyl-5-ethoxycarbonyl-4-methylpyrrol)-2-yl)methylene]-2-indolinone 3-[(3-Acetyl-5-ethoxycarbonyl-4-methylpyrrol)-2-yl)methylene]-2-indolinone is synthesized according to Method A.

45. Synthesis of 3-{[1-(3,5-Dichlorophenyl)pyrrol-2-yl]methylene}-2-indolinone

3-{[1-(3,5-Dichlorophenyl)pyrrol-2-yl]methylene}-2-indolinone is synthesized according to Method A.

46. Synthesis of 3-[1-(4-Chlorophenyl)pyrrol-2-yl)methylene]-2-indolinone

3-[1-(4-Chlorophenyl)pyrrol-2-yl)methylene]-2-indolinone is synthesized according to Method A.

47. Synthesis of 3-[(4-Ethoxycarbonyl-3-methyl)pyrrol-2-yl)methylene]-2-indolinone 3-[(4-Ethoxycarbonyl-3-methyl)pyrrol-2-yl)methylene]-2-indolinone is synthesized according to Method A.

48. Synthesis of 3-[(1-Methylpyrrol-2-yl)methylene]-2-indolinone

3-[(1-Methylpyrrol-2-yl)methylene]-2-indolinone is synthesized according to Method A.

49. Synthesis of 3-[(5-Ethoxycarbonyl-3-ethoxycarbonylethyl-4-ethoxylcarbonylmethylpyrrol-2-yl)methylene]-2-indolinone 3-[(5-Ethoxycarbonyl-3-ethoxycarbonylethyl-4-ethoxylcarbonylmethylpyrrol-2-yl)methylene]-2-indolinone is synthesized according to Method A.

50. Synthesis of 3-[(5-Methylimidazol-2-yl)methylene]-2-indolinone

3-[(5-Methylimidazol-2-yl)methylene]-2-indolinone is synthesized according to Method A.

51. Synthesis of 3-[(5-Methylthiazol-2-yl)methylene]-2-indolinone

3-[(5-Methylthiazol-2-yl)methylene]-2-indolinone is synthesized according to Method A.

52. Synthesis of 3-[(3-Methylpyrazol-5-yl)methylene]-2-indolinone

3-[(3-Methylpyrazol-5-yl)methylene]-2-indolinone is synthesized according to Method A.

53. Synthesis of 3-[(Imidazol-4-yl)methylene]-2-indolinone

3-[(Imidazol-4-yl)methylene]-2-indolinone is synthesized according to Method A.

54. Synthesis of 3-[(4-Chloropyrazol-3-yl)methylene]-2-indolinone

3-[(4-Chloropyrazol-3-yl)methylene]-2-indolinone is synthesized according to Method A.

55. Synthesis of 3-[(4-Bromo-1-(4-chlorobenzyl)pyrazol-5-yl)methylene]-2-indolinone 3-[(4-Bromo-1-(4-chlorobenzyl)pyrazol-5-yl)methylene]-2-indolinone is synthesized according to Method A.

56. Synthesis of 3-[(4-Chloro-1-methylpyrazol-3-yl)methylene]-2-indolinone

3-[(4-Chloro-1-methylpyrazol-3-yl)methylene]-2-indolinone is synthesized according to Method A.

57. Synthesis of 3-[(4-Ethyl-3,5-dimethylpyrrol-2-yl)methylene]-2-indolinone 3-[(4-Ethyl-3,5-dimethylpyrrol-2-yl)methylene]-2-indolinone is synthesized according to Method B.

58. Synthesis of 3-[(5-Ethylpyrrol-2-yl)methylene]-2-indolinone

3-[(5-Ethylpyrrol-2-yl)methylene]-2-indolinone is synthesized according to Method B.

59. Synthesis of 3-[3,5-Dimethyl-4-(propen-2-yl)pyrrol-2-yl)methylene]-2-indolinone)

3-[3,5-Dimethyl-4-(propen-2-yl)pyrrol-2-yl)methylene]-2-indolinone is synthesized according to Method B.

60. Synthesis of 5-Chloro-3-[(pyrrol-2-yl)methylene]-2-indolinone

5-Chloro-3-[(pyrrol-2-yl)methylene]-2-indolinone is synthesized according to Method A.

61. Synthesis of 5-Chloro-3-[(3-methylpyrrol-2-yl)methylene]-2-indolinone

5-Chloro-3-[(3-methylpyrrol-2-yl)methylene]-2-indolinone is synthesized according to Method A.

62. Synthesis of 5-Chloro-3-[(3,5-dimethylpyrrol-2-yl)methylene]-2-indolinone 5-Chloro-3-[(3,5-dimethylpyrrol-2-yl)methylene]-2-indolinone is synthesized according to Method A.

63. Synthesis of 3-[(pyrrol-2-yl)methylene]-2-indolinone

3-[(pyrrol-2-yl)methylene]-2-indolinone is available from Maybridge Chemical Co. Ltd.

64. Synthesis of 5-Chloro-3-[(indol-3-yl)methylene]-2-indolinone

5-Chloro-3-[(indol-3-yl)methylene]-2-indolinone is synthesized according to Method A.

65. Synthesis of 5-Chloro-3-[(thien-2-yl)methylene]-2-indolin one

5-Chloro-3-[(thien-2-yl)methylene]-2-indolinone is synthesized according to Method A.

66. Synthesis of 5-Chloro-3-[(3-methylthien-2-yl)methylene]-2-indolinone

5-Chloro-3-[(3-methylthien-2-yl)methylene]-2-indolinone is synthesized according to Method A.

67. Synthesis of 5-Chloro-3-[(5-methylthien-2-yl)methylene]-2-indolinone

5-Chloro-3-[(5-methylthien-2-yl)methylene]-2-indolinone is synthesized according to Method A.

68. Synthesis of 5-Chloro-3-[(5-ethylthien-2-yl)methylene]-2-indolinone

5-Chloro-3-[(5-ethylthien-2-yl)methylene]-2-indolinone is synthesized according to Method A.

69. Synthesis of 5-Chloro-3-[(5-methylmercaptothien-2-yl)methylene]-2-indolinone 5-Chloro-3-[(5-methylmercaptothien-2-yl)methylene]-2-indolinone is synthesized according to Method A.

70. Synthesis of 5-Chloro-3-[(imidazol-2-yl)methylene]-2-indolinone

5-Chloro-3-[(imidazol-2-yl)methylene]-2-indolinone is synthesized according to Method A.

71. Synthesis of 5-Nitro-3-[(pyrrol-2-yl)methylene]-2-indolinone

5-Nitro-3-[(pyrrol-2-yl)methylene]-2-indolinone is synthesized according to Method A.

72. Synthesis of 3-[(3-Methylpyrrol-2-yl)methylene]-5-nitro-2-indolinone

3-[(3-Methylpyrrol-2-yl)methylene]-5-nitro-2-indolinone is synthesized according to Method A.

73. Synthesis of 3-[(3,5-Dimethylpyrrol-2-yl)methylene]-5-nitro-2-indolinone 3-[(3,5-Dimethylpyrrol-2-yl)methylene]-5-nitro-2-indolinone is synthesized according to Method A.

74. Synthesis of 3-[(Indol-3-yl)methylene]-5-nitro-2-indolinone

3-[(Indol-3-yl)methylene]-5-nitro-2-indolinone is synthesized according to Method A.

75. Synthesis of 5-Nitro-3-[(thien-2-yl)methylene]-2-indolinone

5-Nitro-3-[(thien-2-yl)methylene]-2-indolinone is synthesized according to Method A.

76. Synthesis of 3-[(3-Methylthien-2-yl)methylene]-5-nitro-2-indolinone

3-[(3-Methylthien-2-yl)methylene]-5-nitro-2-indolinone is synthesized according to Method A.

77. Synthesis of 3-[(5-Methylthien-2-yl)methylene]-5-nitro-2-indolinone

3-[(5-Methylthien-2-yl)methylene]-5-nitro-2-indolinone is synthesized according to Method A.

78. Synthesis of 3-[(5-Ethylthien-2-yl)methylene]-5-nitro-2-indolinone

3-[(5-Ethylthien-2-yl)methylene]-5-nitro-2-indolinone is synthesized according to Method A.

79. Synthesis of 3-[(5-Methylmercaptothien-2-yl)methylene]-5-nitro-2-indolinone 3-[(5-Methylmercaptothien-2-yl)methylene]-5-nitro-2-indolinone is synthesized according to Method A.

80. Synthesis of 3-[(Imidazol-2-yl)methylene]-5-nitro-2-indolinone

3-[(Imidazol-2-yl)methylene]-5-nitro-2-indolinone is synthesized according to Method A.

81. Synthesis of 3-[(Oxazol-2-yl)methylene]-2-indolinone

3-[(Oxazol-2-yl)methylene]-2-indolinone is synthesized according to Method A.

82. Synthesis of 3-[(Oxazol-4-yl)methylene]-2-indolinone

3-[(Oxazol-4-yl)methylene]-2-indolinone is synthesized according to Method A.

83. Synthesis of 3-[(Oxazol-5-yl)methylene]-2-indolinone

3-[(Oxazol-5-yl)methylene]-2-indolinone is synthesized according to Method A.

84. Synthesis of 3-[(Thiazol-2-yl)methylene]-2-indolinone

3-[(Thiazol-2-yl)methylene]-2-indolinone is synthesized according to Method A.

85. Synthesis of 3-[(Thiazol-4-yl)methylene]-2-indolinone

3-[(Thiazol-4-yl)methylene]-2-indolinone is synthesized according to Method A.

86. Synthesis of 3-[(Thiazol-5-yl)methylene]-2-indolinone

3-[(Thiazol-5-yl)methylene]-2-indolinone is synthesized according to Method A.

87. Synthesis of 3-[(Imidazol-2-yl)methylene]-2-indolinone

3-[(Imidazol-2-yl)methylene]-2-indolinone is synthesized according to Method A.

88. Synthesis of 3-[(Pyrazol-3-yl)methylene]-2-indolinone

3-[(Pyrazol-3-yl)methylene]-2-indolinone is synthesized according to Method A.

89. Synthesis of 3-[(Pyrazol-4-yl)methylene]-2-indolinone

3-[(Pyrazol-4-yl)methylene]-2-indolinone is synthesized according to Method A.

90. Synthesis of 3-[(Isoxazol-3-yl)methylene]-2-indolinone

3-[(Isoxazol-3-yl)methylene]-2-indolinone is synthesized according to Method A.

91. Synthesis of 3-[(Isoxazol-4-yl)methylene]-2-indolinone

3-[(Isoxazol-4-yl)methylene]-2-indolinone is synthesized according to Method A.

92. Synthesis of 3-[(Isoxazol-5-yl)methylene]-2-indolinone

3-[(Isoxazol-5-yl)methylene]-2-indolinone is synthesized according to Method A.

93. Synthesis of 3-[(Isothiazol-3-yl)methylene]-2-indolinone

3-[(Isothiazol-3-yl)methylene]-2-indolinone is synthesized according to Method A.

94. Synthesis of 3-[(Isothiazol-4-yl)methylene]-2-indolinone

3-[(Isothiazol-4-yl)methylene]-2-indolinone is synthesized according to Method A.

95. Synthesis of 3-[(Isothiazol-5-yl)methylene]-2-indolinone

3-[(Isothiazol-5-yl)methylene]-2-indolinone is synthesized according to Method A.

96. Synthesis of 3-[(1,2,3-Triazol-4-yl)methylene]-2-indolinone

3-[(1,2,3-Triazol-4-yl)methylene]-2-indolinone is synthesized according to Method A.

97. Synthesis of 3-[(1,3,4-Thiadiazol-2-yl)methylene]-2-indolinone

3-[(1,3,4-Thiadiazol-2-yl)methylene]-2-indolinone is synthesized according to Method A.

98. Synthesis of 3-[(5-Phenyl-1,2,4-oxadiazol-3-yl)methylene]-2-indolinone

3-[(5-Phenyl-1,2,4-oxadiazol-3-yl)methylene]-2-indolinone is synthesized according to Method A.

99. Synthesis of 3-[(3-Phenyl-1,2,4-oxadiazol-5-yl)methylene]-2-indolinone

3-[(3-Phenyl-1,2,4-oxadiazol-5-yl)methylene]-2-indolinone is synthesized according to Method A.

100. Synthesis of 3-[(3-Phenyl-1,2,5-oxadiazol-4-yl)methylene]-2-indolinone

3-[(3-Phenyl-1,2,5-oxadiazol-4-yl)methylene]-2-indolinone is synthesized according to Method A.

Other synthetic techniques, such as those described in International patent publication WO 96/22976, published Aug. 1, 1996 may also be used or modified by those skilled in the art to make the compounds of the present invention (hereby incorporated herein by reference in its entirety including any drawings, figures, or tables).

Example 2

Demonstration of Inhibition of Vascular Endothelial Growth Factor-Stimulated Cell Proliferation The effect of several indolinone compounds (Compound II, Compound III, and Compound IV) on VEGF-stimulated cell proliferation of human umbilical vein endothelial cells (HUVEC) is described. The indolinone compounds prevent the phosphorylation of substrate molecules by the activated receptor tyrosine kinase and thereby block signal transduction and the resulting cell proliferation.

The three compounds evaluated inhibited VEGF-stimulation of HUVECs with differing effectiveness and specificity. In this example, Compound III was more potent than Compound II, while Compound IV apparently inhibited VEGF-stimulated proliferation of HUVEC through nonspecific antiproliferative mechanisms, similar to those observed with doxorubicin, a reference compound.

The cellular mechanism of action of Compound II and Compound III can be explained by inhibition of the receptor tyrosine kinases and thereby signal transduction to the cell nucleus which is necessary for the start of cell proliferation. However, the inventors do not wish to be restricted to this explanation.

Materials and Methods:

The cells used were HUV-EC-C (umbilical cord, human) obtained from the ATCC. The cells were cultivated in MEM (Sigma, M5650)+10% FCS (Gibco Brl)+bullet kit and passaged once/week. Only early passages (up to passage 10) were used. The cells were isolated from cell culture flasks by incubation with trypsin/EDTA.

The test compounds were dissolved at 40 mM in DMSO and stored at 4° C. The reference compound doxorubicin was dissolved at 2 mM in A. dest.

The control groups were cells without VEGF and without substances. The test groups were the corresponding groups with additions of serial dilutions of test substances.

Experimental Conditions in vitro: (1) TCA (10%): 10 g TCA was dissolved in 90 g A. dest.; (2) Acetic acid (1%, Merck): 1 mL acetic acid was dissolved in 99 mL of A. dest.; (3) SRB solution (0.4%, Sigma): 2 g sulforhodamin B was dissolved in 500 mL acetic acid (1%); (4) TRIS buffer (10 mM): 1.211 g/L TRIS was dissolved in A. dest. and titrated to pH 10.5 with NaOH (1 M); (5) VEGF stock solution (10 µg/mL): 10 µg VEGF were dissolved in 1000 µL A. dest. Further dilution was done directly in MEM+1% FCS (2241 µL medium+9 µL VEGF stock solution).

Test procedure: $5 \times 10^3$ cells/well in 100 µL MEM+1% FCS were seeded in a 96-well microliter plate (37° C.; 5% $CO_2$ 95% relative humidity). After overnight incubation, the test compounds in 50 µL MEM were added to the wells. For each dilution, 8 wells were performed. 5 min later, 50 µL VEGF (0.04 µg/mL) was added to half of the wells; 50 µL medium was added to the other half of the wells. Incubation proceeded for 3 days. The medium was removed and 100 µL TCA (10%) was added and incubated for 1 h at 4° C. Wells were rinsed three times with 200 µL A. dest. Sulforhodamin B (SRB) solution (0.4% in 1% acetic acid) was added for 1 h at RT (100 µl/well). Wells were rinsed three times with 200 µL acetic acid 1%. The protein-bound dye was solubilized in 200 µL/well TRIS ph 10.5 with gentle shaking.

Concentrations of the compound in the in vitro system: serial dilutions were done in medium (MEM+1% FCS). For the highest concentration, 576 µL medium+24 µL from 40 mM substance stock solution were combined. For the next dilution step, 120 µL from the preceding dilution was added to 480 µL medium. Further serial dilution was done similarly, each time using 120 µL from the preceding dilution step.

For the highest Doxorubicin concentration, 480 µL medium+120 µL from the 2 mM stock solution were combined. For each subsequent dilution step, 120 µL from the preceding dilution was added to 480 µL medium.

In the micro titer plates, the serial dilution series is finally diluted fourfold: test compounds (0.00512–0.0256–0.128–0.64–3.2–16–80–400 µM); doxorubicin (0.000256–0.00128–0.0064–0.032–0.16–0.8–4–20–100 µM).

Observations and Measurements:

The extinction value was measured for each well using an Immuno Reader NJ 2000 AT 570 nm. For Compound IV and doxorubicin, the extinction value in the 300 µM group unexpectedly increased compared to the 80 µM group. Usually higher substance concentrations give rise to higher cell toxicity and therefor to lower extinction values. This phenomenon is due to the color of residual Compound III or doxorubicin inside the well and not to protein-bound SRB.

Evaluation of Data:

For each dilution and control, the mean extinction value of the 4 wells and the standard deviation was calculated (Microsoft Excel 5.0).

The $IC_{50}$ was calculated with the equation "IC50-4 parameter logistic" (start at 0, defined end) out of the software program GraFit 3.0 (Erithacus Software Ltd., Staines, UK).

Inhibition of VEGF-stimulation is calculated according to the following formula, $$\% \text{ inhibition} = \left(100 - \left[\frac{Ex\ SU + PDGF - Ex\ SU - PDGF}{Ex\ control + PDGF - Ex\ control - PDGF} \times 100\right]\right)\%$$

when PDGF is replaced by VEGF:

Ex=mean extinction of the respective group

Results:

To determine the appropriate concentration range for the test on inhibition of VEGF-stimulation for each compound a simple $IC_{50}$ estimation (in the absence of additional VEGF) was done. 400 µM was the highest concentration (for the least toxic substance) tolerated by the cells. Therefore, this was the highest concentration tested in combination with VEGF.

The three compounds inhibited VEGF-stimulation of HUVECs with different potency and specificity (Table 1). The order was Compound III>Compound II>Compound IV. At 0.64 µM, the inhibition was nearly complete with Compound III. Compound II gave a similar picture at a 5-fold higher concentration. The effects of Compound IV, in this example, seem to be more nonspecific, because inhibition occurred at concentrations at which inhibition of the unstimulated control also occurred.

A comparison of the inhibitory $IC_{50}$ of VEGF-stimulated cells with the inhibitory $IC_{50}$ of unstimulated cells (Table 1) shows a clear difference in inhibition when Compound II or Compound III is tested ($IC_{50}$ for inhibition of VEGF-stimulated <$IC_{50}$ for inhibition of unstimulated). However, tests with Compound IV show no difference, or even an inverse difference in inhibition ($IC_{50}$ for inhibition of VEGF-stimulated >IC50 for inhibition of unstimulated). Doxorubicin (cytotoxic control) also showed a similar inhibition pattern on stimulated and unstimulated cells.

Example 3

Demonstration of Inhibition of Platelet-Derived Growth Factor-Stimulated Cell Proliferation The effect of the indolinone compounds of the invention (Compound II, Compound III, and Compound IV) on PDGF-stimulated cell proliferation of rat smooth muscle cells was studied using A10 cells (American Type Culture Collection. A10 cells are embryonic thoracic aorta smooth muscle cells from a DB1X rat. The three compounds show different levels of inhibition of PDGF-stimulation of A10 cells. This is particularly evident when the compounds are preincubated with the cells prior to PDGF addition. Doxorubicin was used as a reference compound.

Compound II, Compound III, and Compound IV are able to inhibit PDGF-stimulated proliferation of (rat) aortic smooth muscle cells. In this example, Compound IV was more potent than Compound II, especially in the preincubation experiments, while Compound III apparently inhibited cell proliferation through a nonspecific mechanism.

The cellular mechanism of action of Compound II and Compound IV can be explained by the inhibition of receptor tyrosine kinases and thereby signal transduction to the cell nucleus, which is a requisite for cell proliferation. However, the inventors should not be held to one possible explanation of the data. In this example, the proliferation data suggest that Compound IV should be the most potent inhibitor of PDGF receptor tyrosine kinase.

Materials and Methods:

A10 cells (embryonic thoracic aorta smooth muscle cells, DB1X rat) were obtained from the ATCC. The cells were cultivated in MEM (Sigma, M5650)+10% FCS (Gibco BRL) and were passaged once/week. The cells were isolated from cell culture flasks by incubation with trypsin/EDTA.

Test Compounds (Compound II, Compound III, and Compound IV) and the reference compound, doxorubicin, were prepared and stored as described in Example I. The same experimental controls are included as in Example I.

Experimental conditions in vitro are as described in Example I, except that PDGF was substituted for VEGF. PDGF stock solution (100 µg/mL; Pepro Tech): 10 µg PDGF were dissolved in 100 µL A. dest. Further dilution was done directly in MEM+5% FCS (2241 µL medium+9 µL PDGF stock solution).

Test procedures were as in Example I except that after the test compounds were added to the wells, 50 µL PDGF, not VEGF, (0.4 µg/mL) was added to half of the wells and 50 µL medium was added to the other half, 5 min or 24 h later. The rest of the experimental protocol was the same as in Example I.

Concentrations of the compound in the in vitro system are as described previously in Example I.

Observations and Measurements:

Similarly to Example I, the extinction value was measured for each well using an Immuno Reader NJ 2000 at 570 nm. For Compound III, the extinction value in the 400 µM group unexpectedly increased compared to the 80 µM group. Usually higher compound concentrations give rise to higher cell toxicity and therefor to lower extinction values. This phenomenon is due to the color of residual Compound III inside the well and not to protein-bound SRB.

Evaluation of Data:

Data were evaluated as for Example I, except that PDGF is used instead of VEGF in the formula.

Results:

To determine the appropriate concentration range for the test on inhibition of PDGF-stimulation for each compound an initial $IC_{50}$ estimation (in the absence of additional PDGF) was done (Tables 2 and 3). 400 µM was the highest concentration (for the least toxic compound) which was tolerated by the cells. Therefore this was the maximal concentration tested in combination with PDGF.

The three compounds inhibit PDGF-stimulation of A10 rat aortic smooth muscle cells with different potencies and specificities. This is most apparent when the compounds are preincubated with the cells for 24 h before PDGF addition (Tables 4,5). The potency of the substances is lower when the substances are added immediately before PDGF addition (especially for Compound IV; Tables 4,5).

In this example, the order of potency is Compound IV>Compound II>Compound III. At 3.2 µM, the inhibition is nearly complete with Compound IV, while Compound II inhibits at 5-fold higher concentrations. The effects of Compound III seem to be more nonspecific, because inhibition of the PDGF-stimulated cells only occurs at concentrations at which the unstimulated cells are also inhibited.

The differences among the activities of the compounds are clearly seen when the inhibitory $IC_{50}$ of PDGF-stimulated cells (Tables 4,5) is compared to the inhibitory $IC_{50}$ of unstimulated cells (Tables 2,3). In this example, there is a clear difference between the stimulated and unstimulated $IC_{50}$ for Compound II and Compound IV, whereas for Compound III there is minimal to no difference. The reference compound, Doxorubicin, showed a comparable inhibition profile on stimulated and unstimulated cells, similar to Compound III (compare the $IC_{50}$ for inhibition of PDGF-stimulated in Table 5 with the $IC_{50}$ for inhibition of unstimulated cells in Table 3).

Example 4

Demonstration of the Effects of Compounds in an Adjuvant Arthritis Model in Rats This study demonstrated the effect of several of the indolinone compounds of the invention (Compound II, Compound III, and Compound IV) in an adjuvant arthritis model in rats. The adjuvant arthritis model is only one example of an animal model that can be used to test the compounds of the invention. For a review of the three most common animal models, see Oliver & Brahn (1996) J. Rheumatol. 23:56–60. The experiments were performed with male Wistar-Lewis rats obtained from Mollegaard Breeding Centre Ltd. The test compounds were given i.p. daily in two recommended doses for 18 days.

All three compounds showed inhibition of paw swelling, and of development of general disease symptoms. Compound III was shown to be the most effective substance, but showed an inverse dose-response at 16 mg/kg. Compound IV showed a clear dose-response and was nearly as potent at 16 mg/kg as Compound III was at 8 mg/kg.

The pharmacodynamic effects of the indolinone compounds can be explained by their inhibition of receptor tyrosine kinases and resulting signal transduction to the cell nucleus which is requisite for cell proliferation. Prevention of cell proliferation inhibits neovascularization and resultant disease progression. However, the inventors do not wish to be restricted to one explanation of the data.

Test System:

The animals were divided into Control and Test groups. The Control group contained three sub-groups: healthy animals, diseased animals with arthritis, and diseased animals with arthritis treated with vehicle. The Test group contained diseased animals with arthritis treated with test compounds in vehicle. Disease was induced by injecting 0.1 mL Freud's adjuvant (=6 mg mycobacterium smegmatis suspension, per mL in heavy white paraffin oil Merck/Darmstadt) into the base of the tail.

The vehicle included PEG400 35%, CREMOPHOR EL 25%, Benzyl alcohol 2%, Ethanol (anhydrous) 11.4%, and sterile water approx. 30%. The specific formulations for the test substances are given in the Table below.

TABLE

Formulation Excipients for Test Compounds

| Excipients | Compounds II & III (g) | Compound IV (g) |
| --- | --- | --- |
| PEG-400 | 44.80 | 96.00 |
| CREMOPHOR EL | 32.00 | 68.57 |
| Benzyl alcohol | 2.56 | 5.46 |
| Ethanol (anhydrous) | 14.60 | 31.24 |
| Qs with water to (mL) | 128.00 | 274.20 |
| mg drug/mL solution | 5.00 | 2.33 |

Wistar-Lewis rats (Möllegaard, Breeding Centre Ltd., EJBY, DK 4623 LI, Skensved, PO Box 28, DK) were administered 5 mL/kg of Compound II and Compound III, and 10 mL/kg of Compound IV, i.p., adjusted with saline to the respective dose (8 mg/kg and 16 mg/kg). Rats were treated daily for days 1 thru 18. Rats were maintained on a normal daylight schedule, given standardized food ALTROMIN® (Altrogge, Lage), and free access to water.

Observations and Measurements:

The arthritis index is calculated according to the following scheme:

| 1. Ears: | 0 points = | absence of nodulation in the cartilage and no adjuvant-induced reddening |
|---|---|---|
| | 1 point = | presence of nudulation in the cartilage and adjuvant-induced reddening |
| 2. Nose: | 0 points = | no swelling process in the connective tissue |
| | 1 point = | severe swelling process in the connective tissue (so-called saddle-nose) |
| 3. Tail: | 0 points = | absence of nodulation |
| | 1 point = | presence of nodulation |
| 4. Front paws: | 0 points = | no inflammatory reactions (= swelling) |
| | ½ point = (per paw) | inflammation of at least one paw joint |
| 5. Hind paws: | 0 points = | no inflammatory reactions (= swelling) |
| | 1 point = | slight inflammation |
| | 2 points = | moderately severe inflammatory reaction |
| | 3 points = | severe inflammation |
| 6. Ballanitis: | = 1 point | |

The index of all animals in a group is summarized and normalized to a group size of 6 animals if necessary. Paw volume is measured plethysmographically.

Evaluation of Data:

Mean values, as well as standard deviation (SD) and standard error of the mean (SEM), were calculated from the tables of individual values in Microsoft Excel 5.0.

Results:

All three indolinone compounds inhibited the increase in paw volume (FIG. 1–3) and a summary of disease symptoms, expressed as a disease index is set forth in Tables 6 and 7.

At the low dose (8 mg/kg), the order of potency was Compound III>Compound IV>Compound II. The inhibition of disease was nearly complete with Compound III. Compound IV was slightly less active. The activity of Compound II seems to be only marginal.

At the higher dose (16 mg/kg), the order of potency was Compound IV>Compound III>Compound II. The inhibition of disease was nearly complete with Compound IV. The reduction of disease symptoms with Compound III was not as marked as with the lower dose. The activity of Compound II at the higher dose was significant, but still not as pronounced as with Compound III or Compound IV at the lower dose.

The course of the body weight curves (FIG. 4), indicates the best tolerability for Compound III and Compound IV (body weight above diseased control+vehicle). For these compounds, the maximal tolerable dose seems to be higher than 16 mg/kg. But at least in the case of Compound III, the increase in the dose from 8 to 16 mg/kg did not improve the pharmacodynamic effect.

Example 5

FGF HUV-EC-C Assay

A specific ELISA method is provided below, however ELISA methods are well-known in the art and other methods and permutations of this method can be envisioned that would also serve to provide the information of interest.

Day 1

1. Wash and trypsinize HUV-EC-C cells (human umbilical vein endothelial cells, (American Type Culture Collection; catalogue no. 1730 CRL). Wash with Dulbecco's phosphate-buffered saline (D-PBS; obtained from Gibco BRL, catalogue no. 14190-029) 2 times at about 1 mL/10 $CM^2$ of tissue culture flask. Trypsinize with 0.05% trypsin-EDTA in non-enzymatic cell dissociation solution (Sigma Chemical Company; catalogue no. C-1544). The 0.05% trypsin was made by diluting 0.25% trypsin/1 mM EDTA (Gibco; catalogue no. 25200-049) in the cell dissociation solution. Trypsinize with about 1 mL/25–30 $cm^2$ Of tissue culture flask for about 5 minutes at 37° C. After cells have detached from the flask, add an equal volume of assay medium (F12K medium (Gibco BRL; catalogue no. 21127-014) plus 0.5% heat inactivated FBS and 2 mM glutamine) and transfer to a 50 mL sterile centrifuge tube (Fisher Scientific; catalogue no. 05-539-6).

2. Wash the cells with about 35 mL assay medium in the 50 mL sterile centrifuge tube by adding the assay medium, centrifuge for 10 minutes at approximately 250×g at room temperature, aspirate the supernatant, and resuspend with 35 mL D-PBS. Repeat the wash two more times with D-PBS, resuspend the cells in about 1 mL assay medium/ 15 $cm^2$ of tissue culture flask. Count the cells with a Coulter Counter®v Coulter Electronics, Inc.) and add assay medium to the cells to obtain a concentration of 0.8–1.0×$10^5$ cells/mL.

3. Add cells to 96-well flat-bottom plates at 100 µL/well or 0.8–1.0×$10^4$ cells/well; incubate ~24 h at 37° C., 5% $CO_2$.

Day 2

1. Make up two-fold drug titrations in separate 96-well plates, generally 50 µM on down to 0 µM in assay medium. Titrations are made by adding 90 µL/well of drug at 200 µM (if possible; 4× the final well concentration) to the top well of a particular plate column. Since the stock drug concentration is usually 20 mM in DMSO, the 200 µM drug concentration contains 2% DMSO.

Therefore, diluent made up to 2% DMSO in assay medium is used as diluent for the drug titrations in order to dilute the drug but keep the DMSO concentration constant. Add this diluent to the remaining wells in the column at 60 µL/well. Take 60 µL from the 120 µL of 200 µM drug dilution in the top well of the column and mix with the 60 µL in the second well of the column. Take 60 µL from this well and mix with the 60 µL in the third well of the column, and so on until two-fold titrations are completed. When the next-to-the-last well is mixed, take 60 µL of the 120 µL in this well and discard it. Leave the last well with 60 µL of DMSO/media diluent as a non-drug-containing control. Make 9 columns of titrated drug, enough for triplicate wells each for 1) VEGF (obtained from Pepro Tech Inc., catalogue no. 100-200, 2) endothelial cell growth factor (ECGF) (also known as acidic fibroblast growth factor, or aFGF) (obtained from Boehringer Mannheim Biochemica, catalogue no. 1439 600); or, 3) human PDGF B/B (1276-956, Boehringer Mannheim, Germany) and assay media control. ECGF comes as a preparation with sodium heparin.

2. Transfer 50 µL/well of the drug dilutions to the 96-well assay plates containing the 0.8–1.0×$10^4$ cells/100 µl/well of the HUV-EC-C cells from day 0 and incubate ~2 h at 37° C., 5% $CO_2$.

3. In triplicate, add VEGF to a final concentration of 5 ng/mL, aFGF to 0.5 ng/mL, or media control to each drug condition. Add ¼ the total assay volume, as with the compounds, thus the growth factor concentrations are 4× the desired final concentration. Use the assay media to make the concentrations of growth factors. Incubate approximately 24 hours at 37° C., 5% $CO_2$. Each well will have 50 µL drug dilution, 50 µL growth factor or media, and 100 µL cells, =200 µL/well total. Thus the 4× concentrations of drugs and growth factors become 1× once everything has been added to the wells.

Day 3
1. Add BrdU (20 μL/well; 10 μM final concentration) and incubate ~24 h at 37 C, 5% $CO_2$. BrdU is made up in serum free F12K medium or F12K medium with 0.5% FBS.

Day 4
1. Perform BrdU ELISA at room temperature as follows:
   a. Flick off medium from the assay plates and pat dry on paper towels.
   b. Add 70 μL/well Fix/Denat (from Boehringer Mannheim) for 30 min.
   c. Flick and pat as in "a".
   d. Add 100 μL/well 5% milk in PBS for 30 min.
   e. Flick and pat as in "a".
   f. Add 80 μL 1:1000 (diluted in PBS+0.1& BSA) anti-BrdU (PharMingen) for 1 hour. Lot to lot variability may require slightly different dilutions as indicated by the manufacturer.
   g. Wash plates 3× in PBS.
   h. Add 80 μL/well goat anti-mouse horse-radish peroxidase (Southern Biotechnology) for 1 hour diluted 1:1000 in PBS+0.1% BSA. Tap plates gently to disperse liquid evenly in well. Lot to lot variability may require slightly different dilutions as indicated by the manufacturer.
   i. Wash 3× in PBS.
   j. Add 100 μL/well ABTS substrate solution for 15–30 min. Before use, add 2 μL $H_2O_2$ for every 10 mL ABTS to be used. Tap plates gently to disperse liquid evenly in every well.
   k. Read on the Dynatech MR5000 plate reader using Biocaalc software and at 410 nm wavelength with 490 nm wavelength as reference.

Results

Compound II showed greater inhibition of FGF-stimulation of cell proliferation than Compound II (8.0 μM versus 16.2 μM, respectively), and both were more potent than Compound IV (>50 μM).

CONCLUSION

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. A method of identifying one or more indolinone compounds of Formula I

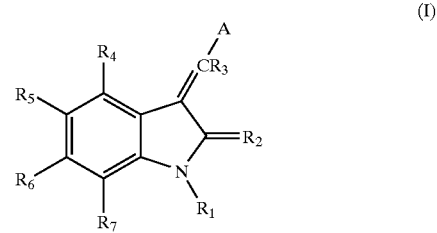

that inhibit growth factor-stimulated cell proliferation comprising the following steps:
   (a) contacting cells with one or more indolinone compounds;
   (b) contacting said cells with one or more growth factors selected from the group consisting of VEGF, PDGF, and FGF;
   (c) monitoring an inhibitory effect on growth factor stimulated cell proliferation; and
   (d) identifying indolinone compounds of formula I that inhibit growth factor-stimulated cell proliferation,
   wherein,
   $R_1$ is H or alkyl;
   $R_2$ is O or S;
   $R_3$ is H;
   $R_4$, $R_5$, $R_6$, and $R_7$ are each independently selected from the group consisting of hydrogen alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR';

A is selected from the group consisting of a 4,5,6,7-tetrahydroindole, thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, wherein said group is optionally substituted with one or more substituents selected from the group consisting of alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR';

n is 0–3;

R is selected from the group consisting of H, alkyl, and aryl; and

R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO₂, and (CH₂)ₙCO₂R.

2. The method of claim 1, wherein said cells are endothelial cells and are contacted with VEGF in step (b).

3. The method of claim 1, wherein said cells are smooth muscle cells and are contacted with PDGF in step (b).

4. The method of claim 1, wherein said cells are endothelial cells and are contacted with FGF in step (b).

5. A method of identifying one or more indolinone compounds of Formula I

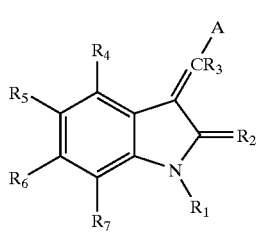

(I)

that are active in an adjuvant arthritis model in rats comprising the following steps:

(a) administering said one or more indolinone compounds to said rats;

(b) monitoring in said rats one or more effects selected from the group consisting of ear nodulation, tail nodulation, nose swelling, paw swelling and ballanitis; and (c) identifying indolinone compounds of formula I that are active in an adjuvant arthritis model in rats.

wherein,

R₁ is H or alkyl;

R₂ is O or S;

R₃ is H;

R₄, R₅, R₆, and R₇ are each independently selected from the group consisting of hydrogen alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR';

A is selected from the group consisting of a 4,5,6,7-tetrahydroindole, thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, wherein said group is optionally substituted with one or more substituents selected from the group consisting of alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR';

n is 0–3;

R is selected from the group consisting of H, alkyl, and aryl; and

R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO₂, and (CH₂)ₙCO₂R.

6. The method of claim 5, wherein said one or more compounds are administered at a concentration in the range of from about 1 to about 1000 mg/m²/day.

7. A method of inhibiting VEGF, FGF, or PDGF stimulated cell proliferation in vein endothelial cells or smooth muscle cells comprising administering to a patient in need of such treatment a composition comprising a therapeutically effective amount of one or more compounds of formula I which inhibit VEGF, FGF, or PDGF stimulated cell proliferation in vein endothelial cells or smooth muscle cells, wherein said composition optionally includes one more pharmaceutically acceptable excipients in at least one of parenteral, oral, or topical formulation:

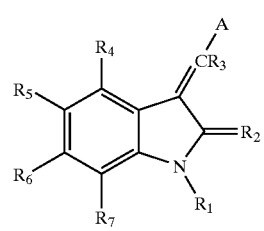

(I)

wherein,

R₁ is H or alkyl;

R₂ is O or S;

R₃ is H;

R₄, R₅, R₆, and R₇ are each independently selected from the group consisting of hydrogen alkyl, alkoxy, aryl, aryloxy, alkaryl, alkaryloxy, halogen, trihalomethyl, S(O)R, SO₂NRR', SO₃R, SR, NO₂, NRR', OH, CN, C(O)R, OC(O)R, NHC(O)R, (CH₂)ₙCO₂R, CONRR', and (CH₂)ₙONRR';

A is selected from the group consisting of a 4,5,6,7-tetrahydroindole, thiophene, pyrrole, pyrazole, 1,2,3-triazole, 1,2,4-triazole, oxazole, isoxazole, thiazole, isothiazole, 2-sulfonylfuran, 4-alkylfuran, 1,2,3- oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, where said group is optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and

R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R.

8. A method of treating arthritis comprising administering to a patient in need of such treatment a pharmaceutically acceptable composition comprising a therapeutically effective amount of one or more compounds of formula I which treat arthritis,

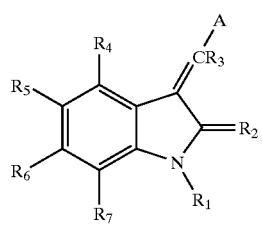

(I)

wherein,

R$_1$ is H or alkyl;

R$_2$ is O or S;

R$_3$ is H;

R$_4$, R$_5$, R$_6$, and R$_7$ are each independently selected from the group consisting of hydrogen alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

A is selected from the group consisting of a 4,5,6,7-tetrahydroindole, thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, where said group is optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and

R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R.

9. A method of inhibiting VEGF, FGF, or PDGF stimulated cell proliferation in vein endothelial cells or smooth muscle cells in vitro, comprising:

a) contacting said cells with one more compounds of formula I which inhibit VEGF, FGF, or PDGF stimulated cell proliferation in vein endothelial cells or smooth muscle cells in vitro, wherein said composition optionally includes one more pharmaceutically acceptable excipients in at least one of parenteral, oral, or topical formulation:

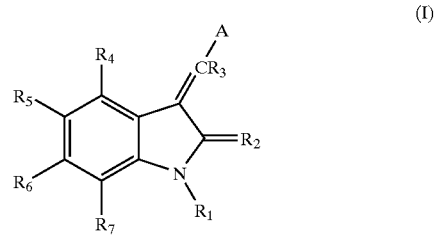

(I)

wherein,

R$_1$ is H or alkyl;

R$_2$ is O or S;

R$_3$ is H;

R$_4$, R$_5$, R$_6$, and R$_7$ are each independently selected from the group consisting of hydrogen alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

A is selected from the group consisting of a 4,5,6,7-tetrahydroindole, thiophene, pyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4,-oxatriazole, 1,2,3,5-oxatriazole, 1,2,3-thiadiazole, 1,2,4-thiadiazole, 1,2,5-thiadiazole, 1,3,4-thiadiazole, 1,2,3,4-thiatriazole, 1,2,3,5-thiatriazole, and tetrazole, where said group is optionally substituted with one or more substituents selected from the group consisting of alkyl, alkoxy, aryl, aryloxy, alkaryl, alkaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, CONRR', and (CH$_2$)$_n$ONRR';

n is 0–3;

R is selected from the group consisting of H, alkyl, and aryl; and

R' is selected from the group consisting of H, alkyl, and aryl, where the alkyl is optionally substituted with a six-membered heteroaliphatic ring, and where the six-membered ring is optionally substituted at one or more positions with substituents selected from the group consisting of alkyl, alkoxy, halogen, trihalomethyl, NO$_2$, and (CH$_2$)$_n$CO$_2$R;

b) measuring the activity of VEGF, FGF, or PDGF; and c) comparing said activity of VEGF, FGF, or PDGF to cells that have not been contacted with one more compounds of formula I.

* * * * *